(12) United States Patent
Husain et al.

(10) Patent No.: US 10,815,519 B2
(45) Date of Patent: Oct. 27, 2020

(54) IMMUNOHISTOCHEMISTRY VIA HYBRIDIZATION CHAIN REACTION

(71) Applicant: California Institute of Technology, Pasadena, CA (US)

(72) Inventors: Naeem S Husain, Los Angeles, CA (US); Harry Ming Tak Choi, Arcadia, CA (US); Long Cai, Pasadena, CA (US); Niles A Pierce, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/689,786

(22) Filed: Aug. 29, 2017

(65) Prior Publication Data

US 2018/0066303 A1    Mar. 8, 2018

Related U.S. Application Data

(60) Provisional application No. 62/381,474, filed on Aug. 30, 2016.

(51) Int. Cl.
| | |
|---|---|
| *C12Q 1/6804* | (2018.01) |
| *C12Q 1/682* | (2018.01) |
| *G01N 33/543* | (2006.01) |
| *C12Q 1/6825* | (2018.01) |
| *G01N 33/536* | (2006.01) |

(52) U.S. Cl.
CPC .......... *C12Q 1/6804* (2013.01); *C12Q 1/682* (2013.01); *C12Q 1/6825* (2013.01); *G01N 33/536* (2013.01); *G01N 33/543* (2013.01); *G01N 33/54306* (2013.01); *G01N 2458/10* (2013.01)

(58) Field of Classification Search
CPC .... C12Q 1/6804; C12Q 1/682; C12Q 1/6825; G01N 33/54306; G01N 33/536; G01N 33/543; G01N 2458/10
See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,270,163 A | 12/1993 | Gold et al. |
| 5,312,728 A | 5/1994 | Lizardi et al. |

(Continued)

FOREIGN PATENT DOCUMENTS

| | | |
|---|---|---|
| EP | 0 273 085 | 7/1988 |
| EP | 1 479 766 | 11/2004 |

(Continued)

OTHER PUBLICATIONS

Appendex Feb. 12, 2020. Prepared by the Examiner on Feb. 12, 2020. (Year: 2020).*

(Continued)

*Primary Examiner* — Joseph G. Dauner
(74) *Attorney, Agent, or Firm* — Knobbe, Martens, Olson & Bear, LLP

(57) ABSTRACT

The present disclosure relates to methods involving HCR reactions that involve using trigger oligos to activate probes that initiate HCR.

19 Claims, 31 Drawing Sheets

(56) References Cited

U.S. PATENT DOCUMENTS

| | | | |
|---|---|---|---|
| 5,424,413 A | 6/1995 | Hogan et al. | |
| 5,459,127 A | 10/1995 | Felgner et al. | |
| 5,563,256 A | 10/1996 | Chakraborty et al. | |
| 5,579,793 A | 12/1996 | Gajewski et al. | |
| 5,643,741 A | 7/1997 | Tsukamoto et al. | |
| 5,677,136 A | 10/1997 | Simmons et al. | |
| 5,691,145 A | 11/1997 | Pitner et al. | |
| 5,716,827 A | 2/1998 | Tsukamoto et al. | |
| 5,750,397 A | 5/1998 | Tsukamoto et al. | |
| 5,928,913 A | 7/1999 | Efstathiou et al. | |
| 5,989,823 A | 11/1999 | Jayasena et al. | |
| 6,128,587 A | 10/2000 | Sjolander | |
| 6,130,047 A | 10/2000 | Nadeau et al. | |
| 6,242,246 B1 | 6/2001 | Gold et al. | |
| 6,255,469 B1 | 7/2001 | Seeman et al. | |
| 6,261,783 B1 | 7/2001 | Jayasena et al. | |
| 6,264,825 B1 | 7/2001 | Blackburn et al. | |
| 6,361,944 B1 | 3/2002 | Mirkin et al. | |
| 6,361,945 B1 | 3/2002 | Becker et al. | |
| 6,485,965 B1 | 11/2002 | Klatzmann et al. | |
| 6,506,559 B1 | 1/2003 | Fire et al. | |
| 6,555,367 B1 | 4/2003 | Spence et al. | |
| 6,696,285 B1 | 2/2004 | Mills, Jr. | |
| 6,899,871 B2 | 5/2005 | Kasahara et al. | |
| 7,033,834 B2 | 4/2006 | Valerio et al. | |
| 7,632,641 B2 | 12/2009 | Dirks et al. | |
| 7,727,721 B2 | 6/2010 | Pierce et al. | |
| 7,960,357 B2 | 6/2011 | Dirks et al. | |
| 8,105,778 B2 | 1/2012 | Dirks et al. | |
| 8,124,751 B2 | 2/2012 | Pierce et al. | |
| 8,241,854 B2 | 8/2012 | Yin et al. | |
| 8,318,921 B2 | 11/2012 | Pierce et al. | |
| 8,478,543 B2 | 7/2013 | Pierce et al. | |
| 8,497,364 B2 | 7/2013 | Pierce et al. | |
| 8,507,204 B2 | 8/2013 | Pierce et al. | |
| 8,658,780 B2 | 2/2014 | Pierce et al. | |
| 8,877,438 B2 | 11/2014 | Yin | |
| 8,962,241 B2 | 2/2015 | Yin et al. | |
| 8,962,582 B2 | 2/2015 | Dirks et al. | |
| 9,217,151 B2 | 12/2015 | Yin et al. | |
| 9,353,404 B2 | 5/2016 | Fletcher | |
| 9,834,439 B2 | 12/2017 | Yin et al. | |
| 9,856,472 B2 | 1/2018 | Pierce et al. | |
| 2001/0014445 A1 | 8/2001 | Urnovitz | |
| 2002/0051769 A1 | 5/2002 | Zhang | |
| 2002/0172950 A1 | 11/2002 | Kenny et al. | |
| 2003/0092162 A1 | 5/2003 | Shankara et al. | |
| 2003/0129611 A1 | 7/2003 | Bao et al. | |
| 2004/0009510 A1 | 1/2004 | Seiwert et al. | |
| 2004/0043386 A1 | 3/2004 | Pray et al. | |
| 2004/0126773 A1 | 7/2004 | Beske et al. | |
| 2004/0223953 A1 | 11/2004 | Kung et al. | |
| 2005/0089864 A1 | 4/2005 | Li et al. | |
| 2005/0112614 A1 | 5/2005 | Cook | |
| 2005/0233332 A1 | 10/2005 | Collis | |
| 2005/0239061 A1 | 10/2005 | Marshall et al. | |
| 2005/0260635 A1 | 11/2005 | Dirks et al. | |
| 2006/0035375 A1 | 2/2006 | Head et al. | |
| 2006/0088864 A1 | 4/2006 | Smolke et al. | |
| 2006/0228733 A1 | 10/2006 | Pierce et al. | |
| 2006/0234261 A1 | 10/2006 | Pierce et al. | |
| 2007/0072215 A1 | 3/2007 | Seelig | |
| 2007/0087334 A1 | 4/2007 | Dirks et al. | |
| 2007/0117109 A1 | 5/2007 | Rothemund | |
| 2008/0183958 A1 | 7/2008 | Cheriton | |
| 2008/0214488 A1 | 9/2008 | Pierce et al. | |
| 2009/0011956 A1 | 1/2009 | Yin et al. | |
| 2009/0123914 A1 | 5/2009 | Erikson et al. | |
| 2009/0197271 A1 | 8/2009 | Kotlikoff et al. | |
| 2009/0227774 A1 | 9/2009 | Turberfield et al. | |
| 2009/0247615 A1 | 10/2009 | Pierce et al. | |
| 2009/0311799 A1 | 12/2009 | Sotzing et al. | |
| 2010/0021901 A1 | 1/2010 | Yin et al. | |
| 2010/0021904 A1 | 1/2010 | Pierce et al. | |
| 2010/0035233 A1 | 2/2010 | Yin et al. | |
| 2010/0047926 A1 | 2/2010 | Dirks et al. | |
| 2011/0059064 A1 | 3/2011 | Possani-Potsay et al. | |
| 2011/0104676 A1 | 5/2011 | Pierce et al. | |
| 2011/0287557 A1 | 11/2011 | Zhang et al. | |
| 2011/0288148 A1 | 11/2011 | Pierce et al. | |
| 2011/0288832 A1 | 11/2011 | Pierce et al. | |
| 2011/0313030 A1 | 12/2011 | Dirks et al. | |
| 2012/0021410 A1 | 1/2012 | Peng et al. | |
| 2012/0022243 A1 | 1/2012 | Peng et al. | |
| 2012/0022244 A1 | 1/2012 | Peng | |
| 2012/0190835 A1 | 7/2012 | Pierce et al. | |
| 2012/0251583 A1 | 10/2012 | Rothemund | |
| 2014/0107983 A1 | 4/2014 | Wolfe et al. | |
| 2015/0004615 A1 | 1/2015 | Pierce et al. | |
| 2015/0154347 A1 | 6/2015 | Wolfe et al. | |
| 2017/0022499 A1 | 1/2017 | Lu et al. | |
| 2018/0010166 A1 | 1/2018 | Pierce et al. | |
| 2018/0362944 A1 | 12/2018 | Hanewich-Hollathz et al. | |

FOREIGN PATENT DOCUMENTS

| | | | |
|---|---|---|---|
| EP | 1 634 890 | 3/2006 | |
| EP | 215 577 0 | 5/2008 | |
| EP | 2 055 781 | 5/2009 | |
| EP | 1 730 161 | 9/2010 | |
| EP | 1 931 806 | 10/2011 | |
| WO | WO 92/03464 | 3/1992 | |
| WO | WO 94/01550 | 1/1994 | |
| WO | WO 99/31276 | 6/1999 | |
| WO | WO 01/40516 | 6/2001 | |
| WO | WO 2005/098049 | 10/2005 | |
| WO | WO 2006/002167 | 1/2006 | |
| WO | WO 2006/048025 | 5/2006 | |
| WO | WO 2007/008276 | 1/2007 | |
| WO | WO 2007/044727 | 4/2007 | |
| WO | WO 2007/141809 | 12/2007 | |
| WO | WO 2007/148337 | 12/2007 | |
| WO | WO 2008/106658 | 2/2008 | |
| WO | WO 2008/144562 | 5/2008 | |
| WO | WO 2011/126996 | 4/2011 | |
| WO | WO 2014/074648 A2 | 5/2014 | |
| WO | WO 2015/118029 A1 | 8/2015 | |
| WO | WO-2015118029 A1 * | 8/2015 | ........... C12Q 1/6841 |
| WO | WO 2015/168404 A1 | 11/2015 | |
| WO | WO 2016/011089 A1 | 1/2016 | |
| WO | WO 2017/223449 A1 | 12/2017 | |
| WO | WO 2018/009463 A3 | 1/2018 | |
| WO | WO 2018/044939 | 3/2018 | |
| WO | WO 2018/231730 A2 | 12/2018 | |

OTHER PUBLICATIONS

Aagaard et al., "RNAi Therapeutics: Principles, Prospects and Challenges." *Advanced Drug Delivery Reviews* 59 (2007): 75-86.

Abudayyeh,.O et al. C2c2 is a single-component programmable RNA-guided RNA-targeting CRISPR effector', Science, (2016).

Acloque, H. et al., "In situ hybridization analysis of chick embryos in whole-mount and tissue sections," Methods in Cell Biology, vol. 87, pp. 169-185, 2008.

Allan et al., "A Concise Total Synthesis of (−)-Quinocarcin via Aryne Annulation." *Journal of American Chemical Society* 130 (2008) 17270-17271.

Amarzguioui et al., "Rational design and in vitro and in vitro delivery of Dicer substrate siRNA,", Nature Protocols, vol. 1, No. 2, pp. 508-517, 2006.

An, C. I.; Trinh, V. B.; Yokobayashi, Y. "Artificial control of gene expression in mammalian cells by modulating RNA interference through aptamer-small molecule interaction" RNA 2006, 12, 710-716.

Andronescu et al., "A New Algorithm for RNA Secondary Structure Design", J. Mol. Biol., vol. 336, pp. 607-624, 2004.

Asbury, C.L., "Kinesin: world's tiniest biped", Current Opinion in Cell Biology, vol. 17, pp. 89-97, 2005.

Barish, R.D.; Schulman, R.; Rothemund, P.W.K.; Winfree, E., "An Information-Bearing seed for nucleating algorithmic self assembly." Proceedings of the National Academy of Sciences 2009, 106, 6054.

(56) References Cited

OTHER PUBLICATIONS

Barrangou, R, et al., 2007. 'CRISPR Provides Acquired Resistance Against Viruses in Prokaryotes', Science, 315, pp. 1709-1712, (2007).
Barroso-Chinea, P. et al., "Detection of two different mRNAs in a single section by dual in situ hybridization: A comparison between colorimetric and fluorescent detection," Journal of Neuroscience Methods, vol. 162, Issues 1-2, pp. 119-128, May 15, 2007.
Bates M.; Huang, B.; Dempsey, G.T.; and Zhuang, X. "Multicolor super-resolution imaging with photo-switchable flurorescent probes." Science, 317: 1749-1759, 2007.
Bath et al., "DNA nanomachines", Nature Nanotechnology, vol. 2, pp. 275-284, May 2007.
Beisel, C. L.; Bayer, T. S.; Hoff, K. G.; Smolke, C. D. "Model-guided design of ligand-regulated RNAi for programmable control of gene expression" Mol. Syst. Biol. 2008, 4, 224.
Beisel, C. L.; Chen, Y. Y.; Culler, S. J.; Hoff, K. G.; Smolke, C. D. "Design of small molecule-responsive microRNAs based on structural requirements for Drosha processing" Nucleic Acids Res. 2011, 39, 2981-2994.
Butterfoss et al., Computer-Based Design of Novel Protein Structures, Annu. Rev. Biophys. Biomol. Struct., vol. 35, pp. 49-65, 2006.
Behenna et al., "The Enantioselective Tsuji Allylation." *Journal of American Chemical Society* 126.46 (2004): 15044-15045.
Bhatia et al., Icosahedral DNA Nanocapsules by Modular Assembly, Angew. Chem. Int. Ed., vol. 48, pp. 4134-4137, 2009.
Bloomfield et al., "Nucleic Acids: Structures, Properties, and Functions." *University Science Books*(2000).
Bois et al., "Topological constraints in nucleic acid hybridization kinetics", Nucleic Acids Research, vol. 33, No. 13, pp. 4090-4095, 2005.
Bolt et al., Differential Reactivities of the mono- and di-epoxide of 1,3-butadiene. *Toxicology* 113(1996): 294-296.
Bonnet et al. Thermodynamic basis of the enhanced specificity of structured DNA probes, Proc. Natl. Acad. Sci. USA vol. 96 (May 1999), pp. 6171-6176.
Bouchard, H, et al., Antibody-drug conjugates: A new wave of cancer drugs. Bioorganic & Medicinal Chemistry Letters, vol. 24, No. 23, pp. 5357-5367, (2014).
Brummelkamp, T. R.; Bernards, R.; Agami, R. "A system for stable expression of short interfering RNAs in mammalian cells" Science 2002, 296, 550-553.
Bumcrot et al., "RNAi Therapeutics: A Potential New Class of Pharmaceutical Drugs." *Nature Chemical Biology* 2.12 (Dec. 2006): 711-719.
Bushnell et al., "ProbeDesigner: for the design of probesets for branched DNA (bDNA) signal amplification assays," Bioinformatics, 15(5), pp. 348-355, 1999.
Caltech News Release, "Caltech Scientists Create New Process to Program", Sep. 6, 2010.
Caplen, "RNAi as a gene therapy approach", Expert Opin. Biol. Ther., vol. 3, No. 4, pp. 575-586, 2003.
Capodieci, P. et al., "Gene expression profiling in single cells within tissue," Nat Methods, vol. 2, No. 9, pp. 663-665, Sep. 2005.
Castanotto et al., "The Promises and Pitfalls of RNA-Interface-Based Therapeutics." *Nature* 457 (Jan. 22, 2009):426-433.
Cerutti et al., "On the Origin and Functions of RNA-Mediated Silencing: From Protists to Man." *Current Genetics* 50 (2006) 81-99.
Chan, PM et al., "Method for multiplex cellular detection of mRNAs using quantum dot fluorescent in situ hybridization," Nucleic Acids Research, vol. 33, Issue 18, pp. e161, Jan. 1, 2005.
Check, "RNA to the rescue?", Nature, vol. 425, pp. 10-12, Sep. 4, 2003.
Chen, B et al. 'Dynamic Imaging of Genomic Loci in Living Human Cells by an Optimized CRISPR/Cas System', Cell, 155: 1479-91, (2013).
Chen, H.L.; Cheng, Q.; Goel, A.; Huang, M.D.' Espanes, P.M.d. "Invadable self-assembly: Combining robustness with efficiency." In Proceedings of the 15$^{th}$ annual ACM-SIAM Symposium on Discrete Algorithms (SODA); 2004.
Chen Y.; Liu, H.P.; Ye, T.; Kim, J.; Mao, C.D. "DNA-Directed Assembly of Single-Wall Carbon Nanotubes." J.Am. Chem. Soc. 2007,129.
Chen, Y et al. Profiling of Multiple Glycans on Whole Living Cell Suraces, Analytical Chemistry, vol. 85, No. 22, pp. 11153-11158, (2013).
Choi et al., Nature Biotechnology 28(11): 1208-1214, 2010.
Choi, H, et al. Programmable in Situ Amplification for Multiplexed Imaging of mRNA Expression, Nature Biotechnology, vol. 28, No. 11, pp. 1206-1212, (2010).
Choi, H. et al., Next-generation in situ hybridization chain reaction: higher gain, lower cost, greater durability, vol. 8, No. 5, pp. 4284-4294 (2014).
Clay, H. et al., "Multiplex fluorescent in situ hybridization in zebrafish embryos using tyramide signal amplification," Zebrafish, vol. 2, No. 2, pp. 105-111, Aug. 2005.
Coburn et al., "siRNAs: a new wave of RNA-based therapeutics", Journal of Antimicrobial Chemotherapy, vol. 51, pp. 753-756, 2003.
Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.
Coleman et al., "Template-Directed Corss-Linking of Oligonucleotides: Site-Specific Covalent Modification of dG-N7 Within Duplex DNA." J. Org. Chem. 60 (1995): 6252-6253.
Collins et al., "A branched DNA signal amplification assay for quantification of nucleic acid targets below 100 molecules/ml," Nucleic Acids Res, 25(15), pp. 2979-2984, 1997.
Coppelli et al., "Oligonucleotides as Anticancer Agents: From the Benchside to the Clinic and Beyond", Current Pharmaceutical Design, vol. 11, pp. 2825-2840, 2005.
Communication Article 94(3) EPC from Application No. 08755764. 1, dated Nov. 7, 2012.
Cong, L. et al. 'Multiplex Genome Engineering Using CRISPR/Cas Systems', Science, 339: 819-23, (2013).
Cox, K.H. et al., "Detection of mRNAs in sea urchin embryos by in situ hybridization using asymmetric RNA probes," Developmental Biology, vol. 101, Issue 2, pp. 485-502, Feb. 1984.
Cullen et al., "Genome-wide Screening for Gene Function Using RNAi in Mammalian Cells." *Immunology and Cell Biology* 83 (2005) 217-223.
Czauderna et al., "Structural Variations and Stabilising Modifications of Synthetic siRNAs in Mammalian Cells." *Nucleic Acids Research* 31.11 (2003): 2705-2716.
Dabby NL, Chen HL, Schaeffer JM, Winfree E. "The kinetics of toehold-mediated four-way branch migration." California Institute of Technology Thesis, Chapter 5 (2013), pp. 75-105.
Darnell, D.K. et al., "GEISHA: an in situ hybridization gene expression resource for the chicken embryo," Cytogenetic and Genome Research, vol. 117, No. 1-4, pp. 30-35, Jul. 2007.
De Matos, et al., Heparanase expression in lung carcinoid tumors by immunohistochemistry. Ejc Supplements , vol. 3, No. 2, pp. 342 (2005).
Definition for "substantial" from Merriam-Webster Online Dictionary. Downloaded from merriam-webster.com; downloaded on Mar. 5, 2008.
DiCarlo, J et al.. 'RNA-guided gene drives can efficiently bias inheritance in wild yeast', bioRxiv, (2015).
Dias et al., "Antisense Oligonucleotides: Basic Concepts and Mechanisms." *Molecular Cancer Therapeutics* 1 (Mar. 2002) 347-355.
Dietz et al., "Folding DNA into Twisted and Curved Nanoscale Shapes." Science 2009, 325, 725-730.
Dirks et al., "An Algorithm for Computing Nucleic Acid Base-Pairing Probabilities Including Pseudoknots." *Journal of Computational Chemistry* 25.10 (2004): 1295-1304.
Dirks et al., "A Partition Function Algorithm for Nucleic Acid Secondary Structure Including Pseudoknots." *Journal of Computational Chemistry* 24.13 (2003) 1664-1677.
Dirks et al., "Paradigms for computational nucleic acid design," Nucleic Acids Research, vol. 32, No. 4, pp. 1392-1403, Oxford University Press, 2004.

(56) References Cited

OTHER PUBLICATIONS

Dirks et al., Retraction for "Selective cell death mediated by small conditional RNAs" (which appeared in issue 39, Sep. 28, 2010 of Proc Natl Acad Sci USA), Proc Natl Acad Sci USA, Jan. 2, 2013 vol. 110, No. 1, p. 384.
Dirks et al., "Thermodynamic Analysis of Interacting Nucleic Acid Strands." *SIAM Review* 49.1 (2007): 65-88.
Dirks et al., "Triggered amplification by hybridization chain reaction," PNAS, vol. 101, No. 43, pp. 15275-15278, Oct. 26, 2004.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.
Du QA, Thonberg H, Wang J, Wahlestedt C, Liang ZC (2005) A systematic analysis of the silencing effects of an active siRNA at all single-nucleotide mismatched target sites. Nucleic Acids Res 33:1671-1677.
Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.
Dunn JJ, Studier FW (1983) Complete nucleotide-sequence of bacteriophage-TY DNA and the locations of T7 genetic elements. J Mol Biol 166:477-535.
Eckstein, F. "Phosphrothioate oligodeooxynucleotides: what is their origin and what is unique about them?" Antisense Nucleic Acid Drug Dev., 10:117-121, 2000.
Eddy, S.R. "Non-coding RNA genes and the modern RNA world." Nature Reviews, 2: 919-929, 2001.
Elbashir et al., "Functional anatomy of siRNAs for mediating efficient RNAi in *Drosophila melanogaster* embryo lysate", The EMBO Journal, vol. 20, No. 23, pp. 6877-6888, 2001.
Elghanian et al.,"Selective colorimetric detection of polynucleotides based on the distance-dependent optical properties of gold nanoparticles," Science, 277(5329), pp. 1078-1081, 1997.
Ellington et al., "In vitro selection of RNA molecules that bind specific ligands," Nature 346, pp. 818-822, 1990.
Elmén et al., "Locked Nucleic Acid (LNA) Mediated Improvements in siRNA Stability and Functionality." *Nucleic Acids Research* 33.1 (2005): 439-447.
Enquist et al.., "The Total Synthesis of ( − )- Cyanthiwigin F by Means of Double Catalytic Enantioselective Alkylation." *Nature* 453.7199 (Jun. 26, 2008) 1228-1231.
Extended European Search Report dated Apr. 22, 2010 in European Patent Application No. 06836249.0.
Extended European Search Report from Application No. 08755764. 1, dated Nov. 7, 2011.
Evanko, "Hybridization chain reaction", Nature Methods, vol. 1, No. 3, pp. 186-187, Dec. 2004.
Feldkamp et al., "Rational Design of DNA Nanoarchitectures", Angew. Chem. Int. Ed., vol. 45, pp. 1856-1876, 2006.
Felgner, et al., "Nomenclature for Synthetic Gene Delivery Systems", Human Gene Therapy, vol. 8, pp. 511-512, Mar. 20, 1997.
Femino et al., "Visualization of Single Molecules of mRNA in Situ." *Methods of Enzymology* 361 (2003): 245-304.
Femino, A. et al., "Visualization of single RNA transcripts in situ," Science, vol. 280, Issue 5363, pp. 585-590, Apr. 24, 1998.
Ferkol et al., "Gene Transfer into the Airway Epithelium of Animals by Targeting the Polymeric Immunoglobulin Receptor", J. Clin. Invest., vol. 95, pp. 493-502, Feb. 1995.
Ferkol et al., "Regulation of the phosphoenolpyruvate carboxykinase/ human factor IX gene introduced into the lives of adult rats by receptor-mediated gene transfer", The FASEB Journal, vol. 7, pp. 1081-1091, Aug. 1993.
Ferreira et al., "The Palladium-Catalyzed Oxidative Kinetic Resolution of Secondary Alcohols with Molecular Oxygen." *Journal of American Chemical Society* 123.31 (2001): 7725-7726.
Final Office Action dated Jun. 28, 2013 for U.S. Appl. No. 13/186,228.
Final Office Action dated Jul. 15, 2011 for U.S. Appl. No. 12/040,735.
Final Office Action dated Jul. 25, 2011 for U.S. Appl. No. 12/395,489.
Final Office Action dated Oct. 15, 2010 for U.S. Appl. No. 12/152,893.
Final Office Action dated Sep. 17, 2010 for U.S. Appl. No. 12/467,755.
Final Office Action dated Sep. 20, 2010 for U.S. Appl. No. 12/454,799.
Final Office Action dated May 27, 2010 for U.S. Appl. No. 11/544,306.
Final Office Action dated Mar. 7, 2013 for U.S. Appl. No. 13/016,811.
Final Office Action dated Jan. 22, 2014 for U.S. Appl. No. 13/186,331.
Final Office Action dated Jun. 25, 2014 for U.S. Appl. No. 13/186,315.
Final Office Action dated Jul. 2, 2014 for U.S. Appl. No. 13/154,989.
Final Office Action dated Aug. 1, 2014 for U.S. Appl. No. 12/454,799.
Final Office Action dated Aug. 29, 2014 for U.S. Appl. No. 12/467,755.
Final Office Action dated Oct. 29, 2014 for U.S. Appl. No. 13/186,228.
Final Office Action dated May 8, 2015 for U.S. Appl. No. 12/467,755.
Final Office Action dated Feb. 4, 2016 for U.S. Appl. No. 12/467,755.
Final Office Action dated Nov. 25, 2015 for U.S. Appl. No. 12/454,799.
Final Office Action dated Dec. 10, 2012 for U.S. Appl. No. 13/363,022.
Final Office Action dated Feb. 7, 2017 for U.S. Appl. No. 14/320,479.
Fire et al., "Potent and specific genetic interference by double-stranded RNA in Caenorhabditis elegans", Nature, vol. 391, pp. 806-811, Feb. 19, 1998.
Flamm et al., "RNA folding at elementary step resolution," RNA, vol. 6, pp. 325-338, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, pp. 223-230, 2004.
Fu et al., "DNA Double-Crossover Molecules", Biochemistry, vol. 32, pp. 3211-3220, 1993.
Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.
Garg et al., "Development of an Enantiodivergent Strategy for the Total Synthesis of (+)- and (−)-Dragmacidin F from a Single Enantiomer of Quinic Acid." *Journal of American Chemical Society* 127 (2005) 5970-5978.
Garg et al., "A Ligand-free Solid-supported System for Sonogashira Couplings: Applications in Nucleoside Chemistry." *Chem. Commun.* (2005) 4551-4553.
Gasparro et al., Site-specific targeting of psoralen photadducts with a triple helix-forming oligonuicleotide: characterization of psoralen monoadduct and crosslink formation. Nucleic Acids Research 22 (1994), pp. 2845-2852.
Gilbert, L. et al. 'CRISPR-Mediated Modular RNA-Guided Regulation of Transcription in Eukaryotes', Cell, 154: 442-51, (2013).
Gilman et al., "The Biological Actions and Therapeutic Applications of the B-Chloroethyl Amines and Sulfides." *Science* 103.2675 (Apr. 5, 1946): 409-415.
Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Ha et al., Regulation of microRNA biogenesis, Nature Reviews Molecular Cell Biology 15, 509-524. Jul. 16, 2014.
Hansma et al., "DNA Binding to Mica Correlates with Cationic Radius: Assay by Atomic Force Microscopy", Biophysical Journal, vol. 70, pp. 1933-1939, Apr. 1996.
Harland, R.M., "In situ hybridization : an improved whole-mount method for Xenopus embryos," Methods Cell Biol., vol. 36, pp. 685-695, 1991.
Hashimoto et al., "Recent Progress in Diazirine-Based Photoaffinity Labeling." *Eur. J. Org. Chem.* (2008): 2513-2523.

(56) References Cited

OTHER PUBLICATIONS

Haugland RP. The Handbook: A Guide to Fluorescent Probes and Labeling Technologies. 10th Ed. Molecular Probes/Invitrogen; 2005.
He et al., Hierarchical self-assembly of DNA into symmetric supramolecular polyhedral, Nature, vol. 452, pp. 198-202, 2008.
Hearst et al., "Psoralen Photochemistry." *Ann.Rev. Biophys.Bioeng.* 10 (1981): 69-86.
Heidel, J.D., "Targeted, systematic non-viral delivery of small interfering RNA in vivo", Doctoral thesis, California Institute of Technology, pp. 1-128, 2005.
Hell, S.W. "Far-field optical nanoscopy." Science, 316: 1153-1158, 2007.
Herath et al., "Synthesis of Acrimarins from 1,3,5-Trioxygenated-9-acridone Derivatives." *Journal of Heterocyclic Chem.* 41 (2004): 23-28.
Higuchi et al. Selective regulation of mutant K-ras mRNA expression by photo-cross-linking antisense oligonucleotide. Nucleic Acids Symposium Series (2007) vol. 51 (1) pp. 443-444.
Hochrein et al., "Conditional Dicer Substrate Formation via Shape and Sequence Transduction with Small Conditional RNAs," *J. Am. Chem. Soc.* 2013, 135, 17322-17330.
Hofacker et al., "Fast folding and comparison of RNA secondary structures," Monatshefte für Chemie, vol. 125, pp. 167-188, 1994.
Hokaiwado et al., "RNAi-based drug discovery and its application to therapeutics", IDrugs, vol. 11, No. 4, pp. 274-278, 2008.
Horvath, P et al.. 'CRISPR/Cas, the Immune System of Bacteria and Archaea', Science, 327: 167-70, (2010).
Hughes et al., "Double Labeling wit Fluorescence In Situ Hybridization in *Drosophila* Whole-Mount Embryos," BioTechniques, 24(4), pp. 530-532, 1998.
Huizenga et al., "A DNA Aptamer That Binds Adenosine and ATP." Biochemistry 34, pp. 656-665, 1995.
Huss, D. et al., Combinatorial analysis of mRNA expression patterns in mouse embryos using hybridization chain reaction. Cold Spring Harbor Protocols, pp. 259-269 (2015).
Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." *Cancer Research* 65.19 (Oct. 1, 2005): 8984-8992.
International Search Report and Written Opinion from PCT/US2005/009471, dated Mar. 8, 2006.
International Search Report and Written Opinion from PCT/US2008/055559, dated Sep. 3, 2008.
International Search Report and Written Opinion of the International Searching Authority for PCT/US11/31127, dated Oct. 31, 2011.
International Search Report and Written Opinion dated Nov. 6, 2017 in International Application No. PCT/US2017/49198.
International Search Report and Written Opinion dated Feb. 5, 2018 in International Application No. PCT/US2017/040485.
Interview Summary dated Jun. 21, 2017 in U.S. Appl. No. 14/320,479.
Interview Summary dated Mar. 29, 2017 in U.S. Appl. No. 14/033,081.
Ikbal, J. et al., The hybridization chain reaction in the development of ultrasensitive nucleic acid assays, Trac-Trends in Analytical Chemistry, vol. 64, pp. 86-99, (2015).
Iqbal et al., "A review of molecular recognition technologies for detection of biological threat agents", Biosensors & Bioelectronics, vol. 15, pp. 549-578, 2000.
Iqbal, J. et al., "The hybridization chain reaction in the development of ultrasensitive nucleic acid assays," TrAC Trends in Analytical Chemistry, vol. 64, pp. 86-99, Jan. 2015.
Jagus et al., "PKR, apoptosis and cancer", The International Journal of Biochemistry & Cell Biology, vol. 31, pp. 123-138, 1999.
Jayasena, "Aptamers: An Emerging Class of Molecules That Rival Antiodies in Diagnostics", Clinical Chemistry, vol. 45, No. 9, pp. 1628-1650, 1999.
Jhaveri et al., "In vitro selection of signaling aptamers", Nature Biotechnology, vol. 18, pp. 1293-1297, Dec. 2000.
Jinek M, Doudna JA (2009) A three-dimensional view of the molecular machinery of RNA interference. Nature 457:405-412.
Jinek,M et al.. 'A Programmable Dual-RNA-Guided DNA Endonuclease in Adaptive Bacterial Immunity', Science, 337: 816-21, (2012).
Johnston et al., "Psoralen-DNA Photoreaction: Controlled Production of Mono- and Diadducts with Nanosecond Ultraviolet Laser Pulses," Science, New Series, vol. 197, No. 4306, pp. 906-908, Aug. 26, 1977.
Jonoska et al., DNA cages with icosahedral symmetry bionanotechnology, Algorithmic Bioprocesses', 2008.
Judge et al., "Design of Noninflammatory Synthetic siRNA Mediating Potent Gene Silencing in Vivo." *Molecular Therapy* 13.3 (Mar. 2006): 494-505.
Judge et al., "Overcoming the Innate Immune Response to Small Interfering RNA", Human Gene Therapy, vol. 19, pp. 111-124, Feb. 2008.
Julian et al., "Biomimetic Approaches to Gas Phase Peptide Chemistry: Combining Selective Binding Motifs with Reactive Carbene Precursors to Form Molecular Mousetraps." *International Journal of Mass Spectrometry* 228 (2003): 851-864.
Julian et al., "Molecular Mousetraps: Gas-Phase Studies of the Covalent Coupling of Noncovalent Complexes Initiated by Reactive Carbenes Formed by Controlled Activation of Diazo Precursors." *Agnew. Chem.Int. Ed.* 42.9 (2003) 1012-1015.
Jung, C. et al., Diagnostic applications of nucleic acid circuits, Accounts of Chemical Research, vol. 47, No. 6, pp. 1825-183, (2014).
Kadnikov et al., "Synthesis of Coumarins via Palladium-Catalyzed Carbonylative Annulation of Internal Alkynes by o-Iodophenols." *Organic Letters* 2.23 (2000): 3643-3646.
Ke et al. "Scaffolded DNA Origami of a DNA Tetrahedron Molecular Container," Nanoletters, 2009. 9(6): 2445-2447.
Kerstens, H.M. et al., "A novel in situ hybridization signal amplification method based on the deposition of biotinylated tyramine," The Journal of Histochemistry and Cytochemistry, vol. 43, No. 4, pp. 347-352, 1995.
Killops, K.L. Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.
Kim J. et al., "Construction of an in vitro bistable circuit from synthetic transcriptional switches." Mol Syst Biol, vol. 2, pp. 68, 2006.
Kim et al., "Synthetic dsRNA Dicer substrates enhance RNAi potency and efficacy", Nature Biotechnology, vol. 23, No. 2, pp. 222-226, Feb. 2005.
Kim et al., "Strategies for Silencing Human Disease Using RNA Interference." *Nature Review Genetics* 8 (Mar. 2007) 173-184.
Kislauskis et al. "Isoform-specific 3ά -untranslated Sequences Sort α-cardiac and β-cytoplasmic Actin Mesenger RNAs to Different ytoplasmic Compartments," The Journal of Cell Biology, 123(1), pp. 165-172, 1993.
Knorre et al., "Photoaffinity Labeling as an Approach to Study Supramolecular Nucleoprotein Complexes." *FEBS Letters* 433 (1998): 9-14.
Kobertz et al., "An Efficient Synthesis of a Furan-Side Furocoumarin Thymidine Monoadduct." *J. Org. Chem.* 62.8 (1997) 2630-2632.
Kobertz et al., "Solid-Phase Synthesis of Oligonucleotides Containing a Site-Specific Psoralen Derivative." *Journal of American Chemical Society* 119 (1997): 5960-5961.
Kobertz et al., "Total Synthesis of a Cis-Syn 2-Carbomethoxypsoralen Furan-Side Thymidine Monoadduct." *Journal of American Chemical Society* 118 (1996): 7101-7107.
Kosman, et al., "Multiplex Detection of RNA Expression in *Drosophila* Embryos," Science, 305, p. 846, 2004.
Kumar D, An CI, Yokobayashi Y (2009) Conditional RNA interference mediated by allosteric ribozyme. J Am Chem Soc 131:13906-13907.
Kumar D, Kim SH, Yokobayashi Y (2011) Combinatorially inducible RNA interference triggered by chemically modified oligonucleotides. J Am Chem Soc 133:2783-2788.
Kurreck, J. Angew. "RNA interference: from basic research to therapeutic applications" Chem., Int. Ed. 2009, 48, 1378-1398.
Kuzuya et al., "Six-Helix and Eight-Helix DNA Nanotubes Assembled from Half-Tubes", Nano Lett., vol. 7, No. 6, pp. 1757-1763, 2007.

(56) References Cited

OTHER PUBLICATIONS

Lacenere et al., "Effects of a Modified Dye-Labeled Nucleotide Spacer Arm on Incorporation by Thermophilic DNA Polymerases." *Nucleosides, Nucleotides, and Nucleic Acids* 25 (2006) 9-15.

Ladiges, et al., "Tissue specific expression of PKR protein kinase in aging B6D2F1 mice," Mechanisms of Ageing and Development, vol. 114, pp. 123-132, (2000).

Larsson, C. et al., "In situ detection and genotyping of individual mRNA molecules," Nature Methods, vol. 7, pp. 395-397, May 1, 2010.

Larsson, C. et al., "In situ genotyping individual DNA molecules by target-primed rolling-circle amplification of padlock probes," Nature Methods, vol. 1, No. 3, pp. 227-232, Dec. 2004.

Lawley et al., "DNA Adducts from Chemotherapeutic Agents." *Mutation Research—Fundamental and Molecular mechanisms of Mutagenesis* 355 (1996): 13-40.

Lawrence et al., "Highly Localized Tracks of Specific Transcripts within Interphase Nuclei Visualized by In Situ Hybridication," Cell, 57, pp. 493-502, 1989.

Layzer et al., "In Vivo Activity of Nuclease-Resistant siRNAs." *RNA* 10 (2004): 766-771.

Le et al., "DNA-Templated Self-Assembly of Metallic Nanocomponent Arrays on a Surface", Nano Lett., vol. 4, No. 12, pp. 2343-2347, 2004.

Lee, J.F. Hesselberth, J.R.; Meyers, L.A.; and Ellington, A.D. "Aptamer database." Nucleic Acids Research, 32: D95-100, 2004.

Lee S. K.; Kumar, P. "Conditional RNAi: towards a silent gene therapy" Adv. Drug Delivery Rev. 2009, 61, 650-664.

Lee et al., "A self-replicating peptide", Nature, vol. 382, pp. 525-528, Aug. 8, 1996.

Levsky et al., "Single-Cell Gene Expression Profiling," Science 297, pp. 836-840, 2002.

Levy et al., "Exponential growth by cross-catalytic cleavage of deoxyribozymogens", PNAS, vol. 100, No. 11, pp. 6416-6421, May 27, 2003.

Li et al., A new class of homogenous nucleic acid probes based on specific displacement hybridization, Nucleic Acids Research, vol. 30, No. 2e5 (2002), pp. 1-9.

Li, H.; LaBean, T.H.; Kenan, D.J. "Single-chain antibodies against DNA aptamers for use as adapter molecules on DNA tile arrays in nanoscale materials organization." Organic and Biomolecular Chemistry 2006, 3420-3426. 2006.

Li Z, Trimble, M.J.; Brun, Y.V.; Jensen, G.J. "The structure of FtsZ filaments in vivo suggests a force-generating role in cell division. "EMBO J.,26, pp. 4694-4708. 2007.

Lima W.F., Wu H.J., Nichols J.G., Sun H., Murray H.M., Crooke S.T. "Binding and cleavage specificities of human Argonaute2" J Biol Chem 284:26017-26028 (2009).

Lin et al., "DNA Tile Based Self-Assembly: Building Complex Nanoarchitectures", ChemPhysChem, vol. 7, pp. 1641-1647, 2006.

Lin, F. et al., Standardization of Diagnostic Immunohistochemistry Literature Review and Geisinger Experience, Archives of Pathology & Laboratory Medicine, vol. 138.

Liu et al., "A colorimetric lead biosensor using DNAzyme-directed assembly of gold nanoparticles," J. Am. Chem. Soc., 125(22), pp. 6642-6643, 2003.

Liu et al., "Approaching the Limit: Can One DNA Oligonucleotide Assemble into Large Nanostructures?", Angew. Chem. Int. Ed., vol. 45, pp. 1942-1945, 2006.

Liu et al., "DNA nanotubes self-assembled from triple-crossover tiles as templates for conductive nanowires", PNAS, vol. 101, No. 3, pp. 717-722, Jan. 20, 2004.

Linuma et al., Polyhedra Self-Assembled from DNA Tripods and Characterized with 3D DNA-PAINT, Science, vol. 344, No. 6179, pp. 65-69, 2014.

Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.

Mahato et al., "Modulation of gene expression by antisense and antigene oligodeoxynucleotides and small interfering RNA", Expert Opin. Drug Deliv., vol. 2, No. 1, pp. 3-28. 2005.

Mali, P et al . . . 'RNA-Guided Human Genome Engineering via Cas9', Science, 339: 823-26., (2013).

Manche et al., "Interactions between Double-Stranded RNA Regulators and the Protein Kinase DAI", Molecular and Cellular Biology, vol. 12, No. 11, pp. 5238-5248, Nov. 1992.

Manoharan et al., "RNA Interference and Chemically Modified Small Interfering RNAs." *Current Opinion in Chemical Biology* 8 (2004): 570-579.

Masu, H.; Narita, A.; Tokunaga, T.; Ohashi, M.; Aoyama, Y.; Sando, S. Angew. "An activatable siRNA probe: trigger-RNA-dependent activation of RNAi" function" Chem., Int. Ed. 2009, 48, 9481-9483.

Mathews, David H., et al. "22 predicting rna secondary structure." Cold Spring Harbor Monograph Archive 43 (2006): 631-657.

Mathieu et al., "Six-Helix Bundles Designed from DNA", Nano Lett., vol. 5, No. 4, pp. 661-665, 2005.

Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.

McIntyre, G. J.; Yu, Y. H.; Lomas, M.; Fanning, G. C. "The effects of stem length and core placement on shRNA activity" BMC Mol. Biol. 2011, 12, 34.

McLennan, R. et al., Neural crest migration is driven by a few trailblazer cells with a unique molecular signature narrowly confined to the invasive front, Development, vol. 142, No. 11, pp. 2014-2025, (2015).

Meinhardt et al., "Wavelength-dependent Penetration Depths of Ultraviolet Radiation in Human Skin." Journal of Biomedical Optics 13.4 (Jul./Aug. 2008) 044030-1-044030-5.

Mitchell et al., "Self-Assembly of Chiral DNA Nanotubes", J. Am. Chem. Soc., vol. 126, pp. 16342-16343, 2004.

Mittelstadt, et al., "Interaction of human tRNA-dihydrouridine synthase-2 with interferon-induced protein kinase PKR," Nucleic Acids Research, vol. 36, No. 3, pp. 998-1008, (2008).

Mohr et al., "Catalytic Enantioselective Decarboxylative Protonation." *Journal of American Chemical Society* 128.35 (2006): 11348-11349.

Mohr et al., "Natural Products as Inspiration for the Development of Asymmetric Catalysis." *Nature* 455 (Sep. 18, 2008) 323-332.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292,American Chemical Society, 2002.

Naked Scientists (The): Science Radio & Science Podcasts. "RNA-away cancer cells", Sep. 12, 2010. http://www.thenakedscientists.com/HTML/content/news/news/2051/.

National Science Foundation, "These Cells Will Self-Destruct in Five . . . Four . . . ", Press Release 10-160, p. 1-3.

Nieto, M. et al., "In situ hybridization analysis of chick embryos in whole mount and tissue sections," Methods in Cell Biology, vol. 51, pp. 219-235, 1996.

Nikolakakis, K et al., Use of Hybridization Chain Reaction-Fluorescent In Situ Hybridization to Track Gene Expression by Both Partners during Initiation of Symbiosis, Applied and Environmental Microbiology, vol. 81, No. 14, pp. 4728-4735, (2015).

Noll et al., "Formation and Repair of Interstrand Cross-Links in DNA." *Chemical Reviews* 106.2 (2006) 277-301.

Noll et al., "Preparation of Interstrand Cross-Linked DNA Oligonucleotide Duplexes." *Frontiers in Bioscience* 9 (Jan. 1, 2004): 421-437.

Notice of Allowance dated Feb. 20, 2013 for U.S. Appl. No. 12/395,489.

Notice of Allowance dated Apr. 4, 2013 for U.S. Appl. No. 13/363,022.

Notice of Allowance dated May 24, 2013 for U.S. Appl. No. 13/016,811.

Notice of Allowance dated Oct. 8, 2014 for U.S. Appl. No. 13/186,315.

Notice of Allowance dated Oct. 9, 2014 for U.S. Appl. No. 13/154,989.

Notice of Allowance dated Jul. 1, 2014 for U.S. Appl. No. 13/183,331.

(56) References Cited

OTHER PUBLICATIONS

Notice of Allowance dated Jun. 26, 2015 for U.S. Appl. No. 12/152,893.
Notice of Allowance dated Jan. 15, 2013 for U.S. Appl. No. 13/363,022.
Notice of Allowance dated Oct. 23, 2013 for U.S. Appl. No. 13/016,811.
Notice of Allowance dated Nov. 8, 2016 for U.S. Appl. No. 13/186,228.
Notice of Allowance dated Feb. 5, 2013 for U.S. Appl. No. 13/079,747.
Notice of Allowance dated Apr. 25, 2017 in U.S. Appl. No. 14/320,479.
Notice of Allowance dated Apr. 5, 2017 for U.S. Appl. No. 13/186,228.
Notice of Allowance dated Jul. 31, 2017 for U.S. Appl. No. 13/186,228.
Notice of Allowance dated Aug. 24, 2017 in U.S. Appl. No. 14/320,479.
Notice to File Corrected Application Papers dated May 22, 2017 in U.S. Appl. No. 14/320,479.
Notice Regarding IDS dated May 25, 2017 in U.S. Appl. No. 14/320,479.
Nutiu et al., "Structure-switching signaling aptamers," J. Am. Chem. Soc., vol. 125, pp. 4771-4778, American Chemical Society, 2003.
Office Action dated Apr. 1, 2010 for U.S. Appl. No. 12/467,755.
Office Action dated Apr. 2, 2014 for U.S. Appl. No. 12/467,755.
Office Action dated Apr. 16, 2010 in U.S. Appl. No. 12/454,799.
Office Action dated Nov. 9, 2010 for U.S. Appl. No. 12/040,735.
Office Action dated Oct. 14, 2011 for U.S. Appl. No. 12/454,743.
Office Action dated Dec. 16, 2010 for U.S. Appl. No. 12/395,489.
Office Action dated Feb. 4, 2010 for U.S. Appl. No. 12/152,893.
Office Action dated Jan. 24, 2013 for U.S. Appl. No. 13/186,228.
Office Action dated Mar. 10, 2011 for U.S. Appl. No. 12/454,743.
Office Action dated Mar. 17, 2011 for U.S. Appl. No. 12/611,875.
Office Action dated Aug. 2, 2013 for U.S. Appl. No. 13/186,315.
Office Action dated Aug. 8, 2013 for U.S. Appl. No. 13/186,331.
Office Action dated Jan. 27, 2014 for U.S. Appl. No. 13/186,315.
Office Action dated Feb. 27, 2014 for U.S. Appl. No. 12/454,799.
Office Action dated May 22, 2014 for U.S. Appl. No. 13/186,228.
Office Action dated Jun. 25, 2014 for U.S. Appl. No. 13/136,315.
Office Action dated Jul. 2, 2014 for U.S. Appl. No. 13/154,989.
Office Action dated Aug. 1, 2014 for U.S. Appl. No. 12/454,799.
Office Action dated Aug. 29, 2014 for U.S. Appl. No. 12/467,755.
Office Action dated Oct. 29, 2014 for U.S. Appl. No. 13/186,228.
Office Action dated Oct. 14, 2014 for U.S. Appl. No. 12/152,893.
Office Action dated Oct. 30, 2014 for U.S. Appl. No. 13/896,235.
Office Action dated Jan. 13, 2015 for U.S. Appl. No. 12/467,755.
Office Action dated May 5, 2015 for U.S. Appl. No. 12/454,799.
Office Action dated Jul. 2, 2015 for U.S. Appl. No. 13/186,228.
Office Action dated Aug. 27, 2015 in U.S. Appl. No. 12/467,755.
Office Action Dated Jul. 8, 2016 for U.S. Appl. No. 13/186,228.
Office Action dated Jun. 22, 2012 for U.S. Appl. No. 13/363,022.
Office Action dated Sep. 20, 2012 for U.S. Appl. No. 13/016,811.
Office Action dated Jan. 30, 2014 for U.S. Appl. No. 13/154,989.
Office Action dated Jan. 5, 2017 for U.S. Appl. No. 14/033,081.
Office Action dated Oct. 12, 2016 for U.S. Appl. No. 14/320,479.
Office Action dated Feb. 22, 2017 for U.S. Appl. No. 14/497,070.
Office Action dated Jan. 4, 2016 in U.S. Appl. No. 13/186,228.
Office Action dated Apr. 27, 2006 in U.S. Appl. No. 11/087,937.
Office Action dated Mar. 1, 2007 in U.S. Appl. No. 11/087,937.
Office Action dated Aug. 23, 2007 in U.S. Appl. No. 11/087,937.
Office Action dated Mar. 25, 2008 in U.S. Appl. No. 11/087,937.
Office Action dated Sep. 26, 2008 in U.S. Appl. No. 11/087,937.
Office Action dated Apr. 30, 2008 in U.S. Appl. No. 11/371,347.
Office Action dated Dec. 3, 2008 in U.S. Appl. No. 11/371,347.
Office Action dated Mar. 26, 2008 in U.S. Appl. No. 11/371,346.
Office Action dated Oct. 16, 2008 in U.S. Appl. No. 11/371,346.
Office Action dated Mar. 20, 2009 in U.S. Appl. No. 11/371,346.
Office Action dated Sep. 29, 2009 in U.S. Appl. No. 11/371,346.
Office Action dated Sep. 21, 2011 in U.S. Appl. No. 12/790,379.
Office Action dated Feb. 8, 2008 in U.S. Appl. No. 11/544,306.
Office Action dated Oct. 15, 2008 in U.S. Appl. No. 11/544,306.
Office Action dated Mar. 19, 2009 in U.S. Appl. No. 11/544,306.
Office Action dated Sep. 2, 2009 in U.S. Appl. No. 11/544,306.
Office Action dated Dec. 24, 2009 in U.S. Appl. No. 11/544,306.
Office Action dated Sep. 19, 2012 in U.S. Appl. No. 12/395,489.
Office Action dated Jul. 2, 2012 in U.S. Appl. No. 13/079,747.
Ouporov, Igor V., and Leontis, Necocles B., "Refinement of the Solution Structure of a Branched DNA Three-Way Junction," Biophysical Journal, vol. 68, pp. 266-274. Jan. 1995.
Opalinska et al., "Nucleic-Acid Therapeutics: Basic Principles and Recent Applications", Nature Reviews Drug Discovery, vol. 1, pp. 503-514, 2002.
Park, S.H.; Yin, P.; Liu, Y.; Reif, J.H.; LaBean, T.H.; Yan, H. "Programmable DNA Self-Assemblies for Nanoscale Organization of Ligands and Proteins." Nano Letters 2005, 5, 729-733.
Park et al., "Rapid Identification of Candida dubliniensis Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Patel et al., Cancer Biology & Therapy 14: 8, 693-696; Aug. 2013.
Paul et al., "A self-replicating ligase ribozyme", PNAS, vol. 99, No. 20, pp. 12733-12740, Oct. 1, 2002.
Peng et al., Facile SNP detection using bifunctional, cross-linking oligonucleotide probes, Nucleic Acids Research vol. 36 No. 5e31 (2008), pp. 1-7.
Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.
Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.
Piston, D.W., and Gremersa, G.J. "Fluorescent protein FRET: the good, the bad and the ugly." Trends in Biochemical Sciences, 32, 2007.
Player et al., "Single-copy Gene Detection Using Branched DNA (bDNA)) In Situ Hybridization," J. Histochem & Cytochem, 49(5), pp. 603-611, 2001.
Pouton et al., "Key issues in non-viral gene delivery", Advanced Drug Delivery Reviews, vol. 46, pp. 187-203, 2001.
Piston et al., "Fluorescent protein FRET: the good, the bad and the ugly", Trends Biochem Sci., Sep. 2007, vol. 32, No. 9, pp. 407-414.
Provost, P. et al., "Ribonuclease activity and RNA binding of recombinant human Dicer," EMBO J., vol. 21, pp. 5864-5874, 2002.
Qi, L. et al.. 'Repurposing CRISPR as an RNA-Guided Platform for Sequence-Specific Control of Gene Expression', Cell, 152: 1173-83. (2013).
Qi et al., "Surface Transfer Doping of Diamond (100) by Tetrafluorotetracyanoquinodimethane", J. Am. Chem. Soc., vol. 129, pp. 8084-8085, 2007.
Qian et al., "Recent Developments in Signal Amplification Methods for In Situ Hybridization," Diagnostic Molecular Pathology, 12(1), pp. 1-13, 2003.
Qian, X., L. Jin, and R.V. Lloyd, In situ hybridization: basic approaches and recent development. The Journal of Histotechnology, 2004. 27(1): p. 53-67.
Rachofsky et al., "Probing structure and dynamics of DNA with 2-aminopurine: Effects of local environment on fluorescence," Biochemistry, vol. 40, pp. 946-956, 2001.
Raj et al., "Imaging Individual mRNA Molecules Using Multiple Singly Labeled Probes." *Nature Methods* 5.10 (Oct. 2008): 877-879.
Read et al., "Barriers to Gene Delivery Using Synthetic Vectors", Advances in Genetics, vol. 53, pp. 19-46, 2005.
Reif, J.H.; Sahu, S.; Yin, P. "Compact Error-Resilient Computational DNA tiling Assemblies." In Proc. $10^{th}$ International Meeting on DNA Computing; 2004.

(56) References Cited

OTHER PUBLICATIONS

Reif, J.H.; Sahu, S.; Yin, P. "Complexity of Graph Self-Assembly in Accretive Systems and Self-Destructible Systems." In Proc. 11th International Meeting on DNA Computing; 2005.
Response to Office Action filed on Jan. 12, 2017 in U.S. Appl. No. 14/320,479.
Restriction Requirement dated Feb. 23, 2006 in U.S. Appl. No. 11/087,937.
Reynolds et al., "Rational siRNA Design for RNA Interference." Nature Biotechnology 22.3 (Mar. 2004) 326-330.
Rosen, B. et al., "Whole-mount in situ hybridization in the mouse embryo: gene expression in three dimensions," Trends in Genetics, vol. 9, Issue 5, pp. 162-167, May 1993.
Rosenthal, A. et al., "Localizing transcripts to single cells suggests an important role of uncultured deltaproteobacteria in the termite gut hydrogen economy," PNAS, vol. 110, No. 40, pp. 16163-16168, Oct. 1, 2013.
Rothemund, P.; Papadakis, J.; Winfree, E. "Algorithmic Self-Assembly of DNA Sierpinski Triangles." PLoS Biology 2004, 2, 2041-2053.
Rothemund et al., "Design and Characterization of Programmable DNA Nanotubes", J. Am. Chem. Soc., vol. 126, pp. 16344-16352, 2004.
Rothemund, P.W.K., "Folding DNA to creat nanoscale shapes and patterns", Nature, vol. 440, pp. 297-302, 2006.
Rothemund, P.W.K.; Winfree, E. "The Program-size complexity of self-assembled squares (extended abstract)." In Proceedings of the thirty-second annual ACM symposium on Theory of computing; ACM Press: 2000.
Sahu et al., "A self-Assembly Model of Time-Dependent Glue Strength." In Proc. 11th International Meeting on DNA Computing; 2005.
Sambrook, J. et al., "Molecular cloning: a laboratory manual," Cold Springs Harbor Press, 1989.
Santalucia J. "A unified view of polymer, dumbbell, and oligonucleotide DNA nearest-neighbor thermodynamics" Proc Natl Acad Sci 95:1460-1465 (1998).
Sander, J. et al., 'CRISPR-Cas systems for editing, regulating and targeting genomes', Nat Biotech, 32: 347-55., (2014).
Saunders et al., "Introduction of DNA into Bacteria." *Methods in Microbiology* 29 (1999): 3-49.
Schärer et al., "DNA Interstrand Crosslinks: Natural and Drug-Induced DNA Adducts that Induce Unique Cellular Responses." *ChemBioChem* 6 (2005): 27-32.
Scherer et al., "Approaches for the sequence-specific knockdown of mRNA", Nature Biotechnology, vol., 21, No. 12, pp. 1457-1465, 2003.
Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "no tail (ntl) is the zebrafish homologue of the mouse T (Brachyury) gene." *Development* 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schweitzer et al., "Combining nucleic acid amplification and detection," Curr Opin Biotechnol, 12, pp. 21-27, 2001.
Seelig et al., "Catalyzed Relaxation of a Metastable DNA Fuel", Journal American Chemical Society, vol. 128, No. 37, pp. 12211-12220, 2006.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, Nature, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.

Seeman, "Nucleic acid nanstructures and topology", Angew. Chem. Int. Ed. vol. 37, pp. 3220-3238 (1998).
Seeman, et al., Nucleic Acid Nanostructures: Bottom Up Control of Geometry on the Nanoscale, Reports on Progress in Physics, 68 :237 (2005).
Sekulic, A.; Hudson, C.C; Homme, J.L.; Yin, P.; Otterness, D.M.; Karnitz, L.M.; Abraham, R.T. A Direct Linkage between the Phosphoinositide 3-Kinase-AKT Signaling Pathway and the Mammalian Target of Rapamycin in Mitogen-stimulated and Transformed Cells. Cancer Research 2000, 60, 3504-3513.
Serra M.J., Turner D.H., "Predicting thermodynamic properties of RNA" Methods Enzymol 259: 242-261 (1995).
Shah et al., "The Fries Isomerization of Acetyl and Benzoyl Esters of Umbelliferones." *J. Org. Chem.* 19 (1954): 1681-1685.
Shaner et al., "A guide to choosing fluorescent proteins", Nature Methods, vol. 2, No. 12, pp. 905-909, Dec. 2005.
Sharma, J.; Chhabra, R.; Cheng, a.; Brownell, J.; Liu, Y.; Yan, H. "Control of Self-Assembly of DNA Tubules through Integration of Gold Nanoparticles" Science 2009, 112-116.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent protein kinase PKR", Nature Biotechnology, vol. 20, pp. 895-900, Sep. 2002.
Shlyakhtenko et al., "Structure of Three-Way DNA Junctions 1. Non-Planar DNA Geometry" Journal of Biomolecular Structure and Dynamics, vol. 11: pp. 1175-1189, Nov. 6, 1994.
Shlyakhtenko et al., "Structure and Dynamics of Three-Way DNA Junctions: Atomic Force Microscopy Studies." Nucleic Acids Research. 2000. 28(19): 3472-3477.
Silverman et al., "Oligonucleotide Probes for RNA-Targeted Fluorescence In Situ Hybridization." *Advances in Clinical Chemistry* 43 (2007): 79-115.
Silverman et al., "Quenched Autoligation Probes Allow Discrimination of Live Bacterial Species by Single Nucleotide Differences in rRNA." *Nucleic Acids Research* 33.15 (2005): 4978-4986.
Singleton, P. et al., "Dictionary of Microbiology and Molecular Biology," 2nd Edition, J. Wiley & Sons, 1994.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Siolas et al., "Synthetic shRNAs as Potent RNAi Triggers." *Nature Biotechnology* 23.2 (Feb. 2005): 227-231.
Sokol et al., "Real time detection of DNA•RNA hybridization in living cells", Proc. Natl. Acad. Sci. USA, vol. 95, pp. 11538-11543, Sep. 1998.
Stack, E., et al. Multiplexed immunohistochemistry, imaging, and quantitation: A review, with an assessment of Tyramide signal amplification, multispectral imaging and multiplex analysis, . Methods, vol. 70, No. 1, (2014).
Stemmer, et al, Single Step Assembly of a Gene and Entire Plasmid from Large Numbers of Oligodeoxyribonnucleotides. Gene, vol. 164, pp. 49-53 (1995).
Storhoff et al., "One-pot colorimetric differentiation of polynucleotides with single base imperfections using gold nanoparticles," J. Am. Chem. Soc., 120, pp. 1959-1964, 1998.
Stratagene Catalog. gene characterization kits. Stratagene Catalog, p. 39, 1988.
Stuheimer, et al. "Global Structure of Three-Way DNA Junctions with and without Additional Unpaired Bases: A Fluorescence Resonance Energy Transfer Analysis". Biochemistry 1997. 35: pp. 13530-13538.
Sun et al.,"Side Chain Chemistry Mediates Backbone Fragmentation in Hydrogen Deficient Peptide Radicals." *Journal of Proteome Research* 8 (2009) 958-966.
Supplementary European Search Report from PCT/US2005/ 009471, dated May 6, 2008.

(56) References Cited

OTHER PUBLICATIONS

Supplemental Notice of Allowance dated Sep. 17, 2015 for U.S. Appl. No. 12/152,893.
Takei et al., "A Small Interfering RNA Targeting Vascular Endothelial Growth Factor as Cancer Therapeutics." Cancer Research 64. (May 15, 2004): 3365-3370.
Tani et al., "Synthesis and Structural Analysis of 2-Quinuclidonium Tetrafluoroborate." Nature 441 (Jun. 8, 2006) 731-734.
Tautz, D. et al., "A non-radioactive in situ hybridization method for the localization of specific RNAs in Drosophila embryos reveals translational control of the segmentation gene hunchback," Chromosoma, vol. 98, Issue 2, pp. 81-85, Aug. 1989.
Thisse, B., "Spatial and temporal expression of the zebrafish genome by large-scale in situ hybridization screening," Methods in Cell Biology, vol. 77, pp. 505-519, 2004.
Thisse, C. et al., "High-resolution in situ hybridization to whole-mount zebrafish embryos," Nature Protocols, vol. 3, No. 1, pp. 59-69, Jan. 2008.
Tijsterman et al., "Dicers at RISC: The Mechanism of RNAi", Cell, vol. 117, pp. 1-3, 2004.
Thomas et al., "Photoaffinity Cross-Linking and RNA Structure Analysis." (2000) 136-147. Methods in Enzymology 318 (2000) 136-147.
Thompson, N.L.; Lieto, A.M., and Allen, N.W. "Recent advances in fluorescence correlation spectroscopy." Curr. Opin.Struct. Biol., 12, 2002.
Trail, P., Antibody drug conjugates as cancer therapeutics, Antibodies, vol. 2, No. 1 pp. 113-129, (2013).
Tuerk et al., "Systematic Evolution of Ligands by Exponential Enrichment: RNA Ligands to Bacteriophage T4 DNA Polymerase," Science 249, pp. 505-510, 1990.
Tuleuova, N.; An, C. I.; Ramanculov, E.; Revzin, A; Yokobayashi, Y. "Modulating endogenous gene expression of mammalian cells via RNA-small molecule interaction" Biochem. Biophys. Res. Commun. 2008, 376, 169-173.
Turberfield, et al., "DNA fuel for free-running nanomachines, "Physical Review Letters, vol. 90, No. 11, pp. 118102-1-118102-4, Mar. 21, 2003.
Turk, Greg and Levoy, Marc. "Zippered polygon meshes from range images." In SIGGRAPH, pp. 311-318, 1994.
Tyagi et al., "Molecular Beacons: Probes that Fluoresce upon Hybridization," Nature Biotechnology 14, pp. 303-308, 1996.
Tyagi, et al., Multicolor Molecular Beacons for Allele Discrimination, Nature Biotechnology vol. 16, pp. 49-53, Jan. 1998.
Van De Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11), pp. 1249-1259, 1998.
Venkataraman et al., "An Autonomous Polymerization Motor Powered by DNA Hybridization." Nature Nanotechnology 2 (Aug. 2007): 490-494.
Venkataraman et al. "Selective Cell Death Mediated by Small Conditional RNAs", Proc Natl Acad Sci USA, early edition, approved Jul. 21, 2010, p. 1-6.
Venkataraman et al. Abstract of "Selective Cell Death Mediated by Small Conditional RNAs", Proc Natl Acad Sci USA, early edition, http://www.pnas.org/content/early/2010/09/01/1006377107. abstract.
Vermeulen et al., "The contributions of dsRNA structure to Dicer specificity and efficiency", RNA, vol. 11, pp. 674-682, 2005.
Vieregg et al., "Selective Nucleic Acid Capture with Shielded Covalent Probes", J. Am. Chem. Soc., 2013, vol. 135, 9691-9699.
Vieregg et al., "Selective Nucleic Acid Capture with Shielded Covalent Probes—Supplemental Materials", J. Am. Chem. Soc., 2013, vol. 135, pp. S1-S52.
Vodovozova et al., "Photoaffinity Labeling and its Application in Structural Biology." Biochemistry (Moscow) 72.1 (2007): 1-20.
Volker, et al., "Conformational energetics of stable and metastable states formed by DNA triple repeat oligonucleotides: implications for triplet expansion diseases,"PNAS, vol. 99, No. 23, pp. 14700-14705, Nov. 12, 2002.
Von Kiedrowski, "A Self-Replicating Hexadeoxynucleotide", Agnew. Chem. Int. Ed. Engl., vol. 25, No. 10, pp. 932-935, 1986.
Voorhoeve et al., "Knockdown Stands Up.:" Trends in Biotechnology 21.1 (Jan. 2003) 2-4.
Wagner et al., "Transferrin-Polycation Conjugates as Carriers for DNA Uptake into Cells", Proceedings of the National Academy of Sciences of the United States of America, vol. 87, pp. 3410-3414, May 1990.
Wallner, G. et al., "Optimizing fluorescent in situ hybridization with rRNA-targeted oligonucleotide probes for flow cytometric identification of microorganisms," Cytometry, vol. 14, Issue 2, pp. 136-143, 1993.
Wang, F. et al. From Cascaded Catalytic Nucleic Acids to Enzyme-DNA Nanostructures: Controlling Reactivity, Sensing, Logic Operations, and Assembly of Complex Structures. Chemical Reviews, vol. 114 No. 5, pp. 2881-2941, (2014.
Wang, F. et al., "RNAscope: A novel in situ RNA analysis platform for formalin-fixed, paraffin-embedded tissues," The Journal of Molecular Diagnostics, vol. 14, No. 1, pp. 22-29, Jan. 2012.
Wassarman et al., "Psoralen Crosslinking of Small RNAs in vitro." Molecular Biology Reports 17 (1993): 143-151.
Weiszmann, R. et al., "Determination of gene expression patterns using high-throughput RNA in situ hybridization to whole-mount Drosophila embryos," Nature Protoc., vol. 4, No. 5, pp. 605-618, 2009.
White et al., "The Catalytic Asymmetric Total Synthesis of Elatol." Journal of American Chemical Society 130.3 (2008): 810-811.
Wijen et al., "The in vivo Genetic Activity Profile of the Monofunctional Nitrogen Mustard 2-Chloroethylamine Differs Drastically from its Bifunctional Counterpart Mechlorethamine." Carcinogenesis 21.10 (2000) 1859-1867.
Wilkie et al., "Transcribed genes are localized according to chromosomal position within polarized Drosophila embryonic nuclei," Current Biology, 9, pp. 1263-1266, 1999.
Williams, B.R.G., "PKR; a sentinel kinase for cellular stress", Oncogene, vol. 18, pp. 6112-6120, 1999.
Willis, M.C., et al. Photocross-linking of 5-Iodouracil-Substituted RNA and DNA to Proteins. Science, 1993. 262: p. 1255-1257.
Winfree et al., "Design and self-assembly of two-dimensional DNA crystals", Nature, vol. 394, pp. 539-544, Aug. 6, 1998.
Winfree, E. Algorithmic Self-Assembly of DNA, Ph.D. thesis. Thesis, California Institute of Technology, 1998.
Winfree, E. "On the computational power of DNA annealing and ligation." Computation and Neural Systems, California Institute of Technology, May 25, 1995.
Wiznerowicz, M.; Szulc, J.; Trono, D. "Tuning silence: conditional systems for RNA interference" Nat. Methods 2006, 3, 682-688.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., "Receptor-mediated in Vitro Gene Transformation by a Soluble DNA Carrier System", The Journal of Biological Chemistry, vol. 262, No. 10, pp. 4429-4432, 1987.
Xie, Z.; Liu, S. J.; Bleris, L.; Benenson, Y. "Logic integration of mRNA signals by an RNAi-based molecular computer" Nucleic Acids Res. 2010, 38, 2692-2701.
Yamaguchi, T. et al., In situ {Dna}-hybridization chain reaction (HCR): a facilitated in situ HCR system for the detection of environmental microorganisms, Environmental Microbiology vol. 17, No. 7 2532-2541. 2015.
Yan et al., "DNA-Templated Self-Assembly of Protein Arrays and Highly Conductive Nanowires", Science, vol. 301, pp. 1882-1884, Sep. 26, 2003.
Yin et al., "Programming biomolecular self-assembly pathways", Nature, vol. 451, pp. 318-323, Jan. 17, 2008.
Yin, P.; Hartemink, "Theoretical and practical advances in genome halving." A.K. Bioinformatics 2005, 21, 869-879.

(56) References Cited

OTHER PUBLICATIONS

Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin, P.; Yan, H.; Daniell, X.; Turberfield, A.J.; Reif, J. "A Unidirectional DNA Walker that Moves Autonomously along a Track." Angewandte Chemie International Edition 2004, 43, 4906-4911.
Yin, P.; Turberfield, A.J.; Reif, J.H. "Designs of Autonomous Unidirectional Walking DNA Devices." In Proc. $10^{th}$ International Meeting on DNA computing; 2004.
Yoshimura et al., "Interstrand Photocrosslinking of DNA via p-carbamoylvinyl Phenol Nucleoside." *Bioorganic & Medicinal Chemistry Letters* 15 (2005): 1299-1301.
Yurke, et al., "A DNA-fuelled molecular machine made of DNA" *Nature*, vol. 406, Aug. 10, 2000, pp. 605-608
Zadeh. "Algorithms for nucleic acid sequence design." Doctoral Thesis [online], orally defended Dec. 8, 2009 (Dec. 8, 2009), published May 25, 2010 (May 25, 2010), [Retrieved on Jun. 7, 2011], pp. 1-85, Retrieved from the Internet: <URL: http://resolver.caltech.edu/CaltechTHESIS:05112010-205335518>.
Zadeh. "Algorithms for nucleic acid sequence design." Doctoral Thesis, defended Dec. 8, 2009; Abstract only [online]; downloaded from URL: http://thesis.library.caltech.edu/5801/ on Jul. 6, 2011.
Zadeh, J. N.; Wolfe, B. R.; Pierce, N. A "Nucleic acid sequence design via efficient ensemble defect optimization" J. Comput. Chem. 2011, 32, 439-452.
Zadeh et al., "Software News and Updates Nupack: Analysis and Design of Nucleic Acid Systems", Journal of Computational Chemistry, vol. 32, No. 1, pp. 170-173, 2011.
Zhang et al., Conformational flexibility facilitates self-assembly of complex DNA nanostructures, PNAS, vol. 105, No. 31, pp. 10665-10669, 2008.
Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zhang, D. Y.; Seelig, G. "Dynamic DNA nanotechnology using strand-displacement reactions" Nat. Chem. 2011, 3, 103-113.
Zhang et al., Targeted Gene Silencing by Small Interfering RNA-Based Knock-Down Technology, Current Pharmaceutical Biotechnology, vol. 5, pp. 1-7, 2004.
Zhang, H. et al., DNA-Mediated Homogeneous Binding Assays for Nucleic Acids and Proteins, Chemical Reviews vol. 113, No. 4, pp. 2812-2841, (2013).
Zheng et al., "Activation of the protein kinase PKR by short double-stranded RNAs with single-stranded tails", RNA, vol. 10, pp. 1934-1945, 2004.
Zhou et al., "RNA Interference and Potential Applications", Current Topics in Medicinal Chemistry, vol. 6, pp. 901-911, 2006.
Zuker et al., "Optimal computer folding of large RNA sequence using thermodynamics and auxiliary information," Nucleic Acids Research, vol. 9, No. 1, pp. 133-147, 1981.
International Preliminary Report on Patentability dated Jan. 17, 2019 in International Application No. PCT/US2017/040485.
Office Action dated Jan. 23, 2019 in U.S. Appl. No. 15/639,100.
International Search Report and Written Opinion dated Apr. 18, 2019 in International Application No. PCT/US2018/036969.
International Preliminary Report on Patentability dated Mar. 15, 2019 in International Application No. PCT/US2017/49198.
Office Action dated Jul. 10, 2019 in U.S. Appl. No. 15/639,100.
Ravan, H., Isothermal RNA Detection Through the Formation of DNA Concatermers Containing HRP-Mimicking DNAzymes on the Surface of Gold Nanoparticles, Biosensors and Bioelectronics, vol. 80, pp. 67-73, 2016.
Extended European Search Report, dated Feb. 7, 2020, in European Application No. EP 17847401.1.
Extended European Search Report, dated Dec. 9, 2019, in European Application No. 17824751.6.
International Preliminary Report, dated Dec. 26, 2019, in International Application No. PCT/US2018/036969.
Notice of Allowance, dated Sep. 5, 2019, in U.S. Appl. No. 15/639,100.
Communication of EP Publication Number, dated Mar. 25, 2020, in EP Application No. 18817173.0.
Lin, F. et al., Standardization of Diagnostic Immunohistochemistry Literature Review and Geisinger Experience, Archives of Pathology & Laboratory Medicine, vol. 138, No. 12, pp. 1564-1577, (2014).
Non-Final Office Action received in U.S. Appl. No. 11/087,937 dated Apr. 27, 2006 in 12 pages.
Final Office Action received in U.S. Appl. No. 11/087,937 dated Mar. 1, 2007 in 18 pages.
Non-Final Amendment Response filed in U.S. Appl. No. 11/087,937 dated May 31, 2007 in 12 pages.
Non-Final Office Action received in U.S. Appl. No. 11/087,937 dated Aug. 23, 2007 in 12 pages.
Non-Final Office Amendment Response filed in U.S. Appl. No. 11/087,937 dated Dec. 21, 2007 in 14 pages.
Final Office Action received in U.S. Appl. No. 11/087,937 dated Mar. 25, 2008 in 24 pages.
Final Amendment Response filed in U.S. Appl. No. 11/087,937 dated May 22, 2008 in 17 pages.
Non-Final Office Action received in U.S. Appl. No. 11/087,937 dated Sep. 26, 2008 in 18 pages.
Interview Summary in U.S. Appl. No. 11/087,937 dated Jan. 13, 2009 in 2 pages.
Non-Final Office Amendment Response filed in U.S. Appl. No. 11/087,937 dated Feb. 26, 2009 in 15 pages.
Notice of Allowance received in U.S. Appl. No. 11/087,937 dated Jun. 17, 2009 in 6 pages.
Notice of Allowance received in U.S. Appl. No. 11/087,937 dated Aug. 11, 2009 in 7 pages.
Office Action received in U.S. Appl. No. 11/087,937 dated Mar. 26, 2006 in 9 pages.
Advisory Action received in U.S. Appl. No. 11/087,937 dated Jun. 16, 2007 in 8 pages.
Advisory Action received in U.S. Appl. No. 11/087,937 dated Jun. 18, 2008 in 4 pages.
Request for Continued Examination and Response to Advisory Action filed in U.S. Appl. No. 11/087,937 dated Jun. 24, 2008 in 17 pages.
Non-Final Office Action received in U.S. Appl. No. 12/611,875 dated Mar. 17, 2011 in 35 pages.
Non-Final Office Amendment Response filed in U.S. Appl. No. 12/611,875 dated Aug. 9, 2011 in 9 pages.
Notice of Allowance received in U.S. Appl. No. 12/611,875 dated Sep. 22, 20011 in 10 pages.
Restriction Requirement received in U.S. Appl. No. 11/371,347 dated Mar. 19, 2008 in 5 pages.
Restriction Requirement Response filed in U.S. Appl. No. 11/371,347 dated Apr. 9, 2008 in 6 pages.
Non-Final Office Action received in U.S. Appl. No. 11/371,347 dated Apr. 13, 2008 in 12 pages.
Non-Final Office Amendment filed in U.S. Appl. No. 11/371,347 dated Jul. 29, 2008 in 10 pages.
Final Office Action received in U.S. Appl. No. 11/371,347 dated Dec. 3, 2008 in 7 pages.
Restriction Requirement received in U.S. Appl. No. 11/371,346 dated Jan. 24, 2017 in 5 pages.
Restriction Requirement Response filed in U.S. Appl. No. 11/371,346 dated Feb. 18, 2008 in 5 pages.
Non-Final Office Action received in U.S. Appl. No. 11/371,346 dated Mar. 26, 2008 in 10 pages.
Non-Final Office Amendment Response filed in U.S. Appl. No. 11/371,346 dated Jun. 25, 2008 in 9 pages.
Final Office Action received in U.S. Appl. No. 11/371,346 dated Oct. 16, 2008 in 9 pages.
Notice of Allowance received in U.S. Appl. No. 11/371,346 dated Jan. 4, 2009 in 10 pages.
Request for Continuation filed in U.S. Appl. No. 11/371,346 dated Feb. 17, 2009 in 12 pages.
Non-Final Office Action received in U.S. Appl. No. 11/371,346 dated Mar. 20, 2009 in 6 pages.

(56) References Cited

OTHER PUBLICATIONS

Non-Final Office Action Terminal Disclosure Response filled in U.S. Appl. No. 11/371,346 dated Jun. 16, 2009 in 12 pages.
Final Office Action received in U.S. Appl. No. 11/371,346 dated Sep. 29, 2009 in 9 pages.
Final Office Amendment Response filed in U.S. Appl. No. 11/371,346 dated Dec. 9, 2009 in 5 pages.
Restriction Requirement received in U.S. Appl. No. 12/790,379 dated Sep. 21, 2010 in 5 pages.
Restriction Requirement Response filed in U.S. Appl. No. 12/790,379 dated Jan. 11, 2011 in 8 pages.
Restriction Requirement received in U.S. Appl. No. 12/790,379 dated Jun. 13, 2011 in 6 pages.
Restriction Requirement Response filed in U.S. Appl. No. 12/790,379 dated Jul. 12, 2011 in 5 pages.
Non-Final Office Action received in U.S. Appl. No. 12/790,379 dated Sep. 21, 2011 in 18 pages.
Non-Final Office Amendment Response filed in U.S. Appl. No. 12/790,379 dated Oct. 4, 2011 in 6 pages.
Notice of Allowance received in U.S. Appl. No. 12/790,379 dated Nov. 1, 2011 in 21 pages.
Restriction Requirement received in U.S. Appl. No. 11/544,306 dated Nov. 14, 2007 in 10 pages.
Restriction Requirement received in U.S. Appl. No. 11/544,306 dated Dec. 12, 2007 in 4 pages.
Non-Final Office Action received in U.S. Appl. No. 11/544,306 dated Feb. 8, 2008 in 170 pages.
Non-Final Office Amendment Response filled in U.S. Appl. No. 11/544,306 dated May 22, 2008 in 11 pages.
Amendment Received in U.S. Appl. No. 11/544,306 dated Jul. 18, 2008 in 2 pages.
Amendment Received in U.S. Appl. No. 11/544,306 dated Dec. 2, 2009 in 12 pages.
Non-Final Corrected Office Action filed in U.S. Appl. No. 11/544,306 dated Jul. 24, 2008 in 11 pages.
Non-Final Office Action received in U.S. Appl. No. 11/544,306 dated Oct. 15, 2008 in 19 pages.
Non-Final Office Amendment Response filed in U.S. Appl. No. 11/544,306 dated Jan. 15, 2009 in 13 pages.
Non-Final Office Action received in U.S. Appl. No. 11/544,306 dated Mar. 19, 2009 in 22 pages.
Non-Final Office Amendment Response received in U.S. Appl. No. 11/544,306 dated Jun. 16, 2009 in 16 pages.
Final Office Action received in U.S. Appl. No. 11/544,306 dated Sep. 2, 2009 in 21 pages.
Non-Final Amendment Response filed in U.S. Appl. No. 11/544,306 dated Nov. 2, 2009 in 14 pages.
Request for Continuation filed in U.S. Appl. No. 11/544,306 dated Dec. 2, 2009 in 12 pages.
Non-Final Office Action received in U.S. Appl. No. 11/544,306 dated Dec. 24, 2009 in 16 pages.
Non-Final Amendment Response filed in U.S. Appl. No. 11/544,306 dated Apr. 23, 2010 in 10 pages.
Final Office Action received in U.S. Appl. No. 11/544,306 dated May 27, 2010 in 16 pages.
Interview Summary in U.S. Appl. No. 11/544,306 dated Jul. 23, 2010 in 3 pages.
Request for Continuation filed in U.S. Appl. No. 11/544,306 dated Aug. 25, 2010 in 14 pages.
Interview Summary in U.S. Appl. No. 11/544,306 dated Oct. 19, 2010 in 3 pages.
Interview Summary in U.S. Appl. No. 11/544,306 dated Oct. 25, 2010 in 3 pages.
Comments on Statement of Reasons for Allowance in U.S. Appl. No. 11/544,306 dated Apr. 22, 2011 in 2 pages.
Response to Rule 312 Communication in U.S. Appl. No. 11/544,306 dated Apr. 13, 2011 in 3 pages.
Advisory Action received in U.S. Appl. No. 11/544,306 dated Nov. 18, 2009 in 3 pages.
Non-Final Amendment Response filed in U.S. Appl. No. 11/544,306 dated Apr. 8, 2011 in 4 pages.
Amendment, RCE, and Response to Final Office Action in U.S. Appl. No. 11/544,306 dated Aug. 25, 2010 in 14 pages.
Restriction Requirement received in U.S. Appl. No. 12/040,735 dated Apr. 13, 2010 in 11 pages.
Restriction Requirement Response filed in U.S. Appl. No. 12/040,735 dated May 13, 2010 in 6 pages.
Restriction Requirement received in U.S. Appl. No. 12/040,735 dated Aug. 2, 2010 in 6 pages.
Restriction Requirement Response filed in U.S. Appl. No. 12/040,735 dated Aug. 17, 2010 in 6 pages.
Non-Final Office Action received in U.S. Appl. No. 12/040,735 dated Nov. 9, 2010 in 20 pages.
Interview Summary in U.S. Appl. No. 12/040,735 dated Apr. 12, 2011 in 3 pages.
Non-Final Amendment Response filed in U.S. Appl. No. 12/040,735 dated May 6, 2011 in 10 pages.
Final Office Action received in U.S. Appl. No. 12/040,735 dated Jul. 15, 2011 in 15 pages.
Interview Summary in U.S. Appl. No. 12/040,735 dated Oct. 5, 2011 in 3 pages.
Amendment accompanying Request for Continued Examination filed in U.S. Appl. No. 12/040,735 dated Nov. 7, 2012 in 10 pages.
Notice of Allowance received in U.S. Appl. No. 12/040,735 dated Aug. 3, 2012 in 15 pages.
Restriction Requirement received in U.S. Appl. No. 12/152,893 dated Nov. 20, 2009 in 10 pages.
Amendment and Restriction Requirement filed in U.S. Appl. No. 12/152,893 dated Dec. 18, 2009 in 8 pages.
Non-Final Office Action received in U.S. Appl. No. 12/152,893 dated Feb. 4, 2010 in 34 pages.
Non-Final Office Action filed in U.S. Appl. No. 12/152,893 dated Aug. 3, 2010 in 13 pages.
Final Office Action received in U.S. Appl. No. 12/152,893 dated Oct. 15, 2010 in 34 pages.
Non-Final Office Action received in U.S. Appl. No. 12/152,893 dated Oct. 14, 2014 in 61 pages.
Interview Summary U.S. Appl. No. 12/152,893 dated Jan. 22, 2015 in 3 pages.
Non-Final Office Action Response filed in U.S. Appl. No. 12/152,893 dated Feb. 17, 2015 in 12 pages.
Notice of Allowance received in U.S. Appl. No. 12/152,893 dated Jun. 26, 2015 in 10 pages.
Notice of Allowance received in U.S. Appl. No. 12/152,893 dated Sep. 17, 2015 in 5 pages.
Response to Final Office Action received in U.S. Appl. No. 12/152,893 dated Jan. 18, 2011 in 9 pages.
Restriction Requirement received in U.S. Appl. No. 12/395,489 dated Sep. 24, 2010 in 8 pages.
Restriction Requirement Response filed in U.S. Appl. No. 12/395,489 dated Oct. 22, 2010 in 6 pages.
Non-Final Office Action received in U.S. Appl. No. 12/395,489 dated Dec. 16, 2010 in 62 pages.
Non-Final Amendment Response filed in U.S. Appl. No. 12/395,489 dated May 16, 2011 in 11 pages.
Final Office Action received in U.S. Appl. No. 12/395,489 dated Nov. 25, 2011 in 16 pages.
Interview Summary received in U.S. Appl. No. 12/395,489 dated Oct. 5, 2011 in 3 pages.
Amendment accompanying Request for Continued Examination filed in U.S. Appl. No. 12/395,489 dated Jan. 12, 2012 in 9 pages.
Non-Final Office Action received in U.S. Appl. No. 12/395,489 dated Sep. 19, 2012 in 19 pages.
Non-Final Office Action Amendment Response filed in U.S. Appl. No. 12/395,489 dated Dec. 5, 2012 in 7 pages.
Notice of Allowance received in U.S. Appl. No. 12/395,489 dated Jan. 14, 2013 in 5 pages.
Notice of Allowance received in U.S. Appl. No. 12/395,489 dated Feb. 20, 2013 in 12 pages.
Amendment After Allowance (37 C.F.R. §1.312) filed in U.S. Appl. No. 12/395,489 dated Apr. 2, 2013 in 4 pages.

(56) References Cited

OTHER PUBLICATIONS

Response to Rule 312 Communication in U.S. Appl. No. 12/395,489 dated Jul. 8, 2013 in 2 pages.
Restriction Requirement received in U.S. Appl. No. 12/454,799 dated Feb. 8, 2010 in 6 pages.
Restriction Requirement Response filed in U.S. Appl. No. 12/454,799 dated Feb. 2, 2010 in 7 pages.
Non-Compliant Amendment Response filed in U.S. Appl. No. 12/454,799 dated Mar. 12, 2010 in 9 pages.
Non-Final Office Action received in U.S. Appl. No. 12/454,799 dated Apr. 16, 2010 in 15 pages.
Non-Final Office Action Amendment Response filed in U.S. Appl. No. 12/454,799 dated Jun. 25, 2010 in 9 pages.
Final Office Action received in U.S. Appl. No. 12/454,799 dated Sep. 20, 2010 in 5 pages.
Final Office Action Amendment Response filed in U.S. Appl. No. 12/454,799 dated Dec. 20, 2010 in 12 pages.
Final Office Action Amendment, RCE and Response filed in U.S. Patent Application No. 12/454,799 dated May 23, 2011 in 12 pages.
Non-Final Office Action received in U.S. Appl. No. 12/454,799 dated Feb. 27, 2014 in 16 pages.
Non-Final Office Action Amendment Response filed in U.S. Appl. No. 12/454,799 dated May 23, 2014 in 8 pages.
Final Office Action received in U.S. Appl. No. 12/454,799 dated Aug. 8, 2014 in 11 pages.
Final Office Action Amendment Response filed in U.S. Appl. No. 12/454,799 dated Oct. 17, 2014 in 12 pages.
Interview Summary U.S. Appl. No. 12/454,799 dated Oct. 19, 2014 in 3 pages.
Amendment with Request for Continued Examination filed in U.S. Appl. No. 12/454,799 dated Nov. 25, 2014 in 11 pages.
Non-Final Office Action received in U.S. Appl. No. 12/454,799 dated May 5, 2015 in 24 pages.
Non-Final Office Action Amendment Response filed in U.S. Appl. No. 12/454,799 dated Sep. 3, 2015 in 13 pages.
Final Office Action received in U.S. Appl. No. 12/454,799 dated Nov. 25, 2015 in 13 pages.
Advisory Action received in U.S. Appl. No. 12/454,799 dated Jan. 18, 2011 in 6 pages.
Advisory Action received in U.S. Appl. No. 12/454,799 dated Oct. 29, 2014 in 3 pages.
Request for Continued Examination in U.S. Appl. No. 12/454,799 dated May 23, 2011 in 2 pages.
Non-Final Office Action Amendment Response filed in U.S. Appl. No. 12/467,755 dated Feb. 3, 2010 in 7 pages.
Restriction Requirement Response filed in U.S. Appl. No. 12/467,755 dated Feb. 25, 2010 in 2 pages.
Non-Final Office Action Amendment Response filed in U.S. Appl. No. 12/467,755 dated Jun. 30, 2010 in 11 pages.
Non-Final Office Action Amendment Response filed in U.S. Appl. No. 12/467,755 dated Jul. 1, 2010 in 13 pages.
Final Office Action received in U.S. Appl. No. 12/467,755 dated Sep. 17, 2010 in 43 pages.
Interview Summary U.S. Appl. No. 12/467,755 dated Nov. 29, 2010 in 4 pages.
Final Office Action Amendment, RCE and Response filed in U.S. Appl. No. 12/467,755 dated Dec. 16, 2010 in 14 pages.
Non-Final Office Action received in U.S. Appl. No. 12/467,755 dated Apr. 1, 2014 in 16 pages.
Non-Final Office Action received in U.S. Appl. No. 12/467,755 dated Apr. 2, 2014 in 50 pages.
Non-Final Office Amendment Response filed in U.S. Appl. No. 12/467,755 dated Jun. 20, 2014 in 11 pages.
Final Office Action received in U.S. Appl. No. 12/467,755 dated Aug. 29, 2014 in 23 pages.
Final Office Action Amendment Response filed in U.S. Appl. No. 12/467,755 dated Nov. 25, 2014 in 16 pages.
Interview Summary U.S. Appl. No. 12/467,755 dated Jan. 13, 2015 in 29 pages.
Non-Final Office Action Amendment Response filed in U.S. Appl. No. 12/467,755 dated Apr. 10, 2015 in 18 pages.
Final Office Action received in U.S. Appl. No. 12/467,755 dated May 8, 2015 in 25 pages.
Interview Summary U.S. Appl. No. 12/467,755 dated Jul. 31, 2015 in 3 pages.
Final Office Action Accompanying Request for Continued Examination Amendment Response filed in U.S. Appl. No. 12/467,755 dated Aug. 7, 2015 in 22 pages.
Supplemental Amendment received filed in U.S. Appl. No. 12/467,755 dated Aug. 26, 2015 in 4 pages.
Non-Final Office Action received in U.S. Appl. No. 12/467,755 dated Aug. 27, 2015 in 20 pages.
Non-Final Office Action Amendment Response filed in U.S. Appl. No. 12/467,755 dated Nov. 23, 2015 in 13 pages.
Final Office Action received in U.S. Appl. No. 12/467,755 dated Feb. 4, 2016 in 21 pages.
Non-Final Office Action received in U.S. Appl. No. 12/454,743 dated Aug. 23, 2010 in 9 pages.
Restriction Requirement Response filed in U.S. Appl. No. 12/454,743 dated Sep. 23, 2010 in 9 pages.
Restriction Requirement Response filed in U.S. Appl. No. 12/454,743 dated Jan. 1, 2011 in 11 pages.
Non-Final Office Action received in U.S. Appl. No. 12/454,743 dated Mar. 10, 2011 in 25 pages.
Non-Final Office Action Amendment Response filed in U.S. Appl. No. 12/454,743 dated Aug. 10, 2011 in 10 pages.
Non-Final Office Action received in U.S. Appl. No. 12/454,743 dated Oct. 14, 2011 in 18 pages.
Non-Final Office Action Amendment Response filed in U.S. Appl. No. 12/454,743 dated Feb. 14, 2012 in 9 pages.
Notice of Allowance received in U.S. Appl. No. 12/454,743 dated Apr. 13, 2012 in 29 pages.
Non-Final Office Action received in U.S. Appl. No. 13/186,228 dated Nov. 6, 2012 in 6 pages.
Restriction Requirement Response filed in U.S. Appl. No. 13/186,228 dated Dec. 5, 2012 in 1 page.
Non-Final Office Action received in U.S. Appl. No. 13/186,228 dated Jan. 24, 2013 in 36 pages.
Non-Final Office Amendment Response filed in U.S. Appl. No. 13/186,228 dated Apr. 22, 2013 in 10 pages.
Final Office Action received in U.S. Appl. No. 13/186,228 dated Jun. 28, 2013 in 21 pages.
Final Office Amendment, RCE and Response filed in U.S. Appl. No. 13/186,228 dated Sep. 27, 2013 in 13 pages.
Non-Final Office Action received in U.S. Appl. No. 13/186,228 dated May 22, 2014 in 24 pages.
Non-Final Office Amendment Response filed in U.S. Appl. No. 13/186,228 dated Aug. 21, 2014 in 15 pages.
Final Office Action received in U.S. Appl. No. 13/186,228 dated Oct. 29, 2014 in 24 pages.
Final Office Action Amendment Response received in U.S. Appl. No. 13/186,228 dated Jan. 28, 2015 in 15 pages.
Non-Final Office Action received in U.S. Appl. No. 13/186,228 dated Jul. 2, 2015 in 29 pages.
Interview Summary U.S. Appl. No. 13/186,228 dated Oct. 2, 2015 in 4 pages.
Non-Final Office Action Amendment Response filed in U.S. Appl. No. 13/186,228 dated Oct. 29, 2015 in 18 pages.
Final Office Action received in U.S. Appl. No. 13/186,228 dated Jan. 4, 2016 in 13 pages.
Final Office Action and Request Under AFCP 2.0 Amendment Response filed in U.S. Appl. No. 13/186,228 dated Mar. 4, 2016 in 19 pages.
Final Office Action and Request Under AFCP 2.0 Amendment Response filed in U.S. Appl. No. 13/186,228 dated Apr. 6, 2016 in 19 pages.
Amendment with Request for Continued Examination filed in U.S. Appl. No. 13/186,228 dated Apr. 6, 2016 in 17 pages.
Non-Final Office Action received in U.S. Appl. No. 13/186,228 dated Jul. 8, 2016 in 15 pages.
Non-Final Office Action Amendment Response filed in U.S. Appl. No. 13/186,228 dated Oct. 7, 2016 in 17 pages.

(56) References Cited

OTHER PUBLICATIONS

Notice of Allowance received in U.S. Appl. No. 13/186,228 dated Nov. 8, 2016 in 15 pages.
Notice of Allowance received in U.S. Appl. No. 13/186,228 dated Apr. 5, 2017 in 36 pages.
Notice of Allowance received in U.S. Appl. No. 13/186,228 dated Jul. 31, 2017 in 9 pages.
Non-Final Office Action Amendment Response filed in U.S. Appl. No. 13/186,331 dated Jul. 19, 2013 in 11 pages.
Non-Final Office Action received in U.S. Appl. No. 13/186,228 dated Aug. 8, 2013 in 32 pages.
Non-Final Office Action Amendment Response filed in U.S. Appl. No. 13/186,228 dated Nov. 7, 2013 in 14 pages.
Final Office Action received in U.S. Appl. No. 13/186,228 dated Jan. 22, 2014 in 16 pages.
Non-Final Office Action received in U.S. Appl. No. 13/186,315 dated Aug. 2, 2013 in 46 pages.
Non-Final Office Action Amendment Response filed in U.S. Appl. No. 13/186,315 dated Nov. 1, 2013 in 13 pages.
Non-Final Office Action received in U.S. Appl. No. 13/186,315 dated Jan. 27, 2014 in 36 pages.
Non-Final Office Action Amendment Response filed in U.S. Appl. No. 13/186,315 dated Apr. 25, 2014 in 18 pages.
Final Office Action received in U.S. Appl. No. 13/186,315 dated Jun. 25, 2014 in 23 pages.
Final Office Action Amendment Response filed in U.S. Appl. No. 13/186,315 dated Aug. 29, 2014 in 15 pages.
Notice of Allowance received in U.S. Appl. No. 13/186,315 dated Oct. 8, 2014 in 12 pages.
Corrected Notice of Allowability received in U.S. Appl. No. 13/186,315 dated Nov. 12, 2014 in 3 pages.
Non-Final Office Action received in U.S. Appl. No. 14/033,081 dated Jan. 5, 2017 in 12 pages.
Interview Summary U.S. Appl. No. 14/320,479 dated Nov. 28, 2011 in 3 pages.
Non-Final Office Action Amendment Response filed in U.S. Appl. No. 14/320,479 dated May 23, 2016 in 7 pages.
Non-Final Office Amendment Response filed in U.S. Appl. No. 14/320,479 dated Oct. 12, 2016 in 34 pages.
Non-Final Office Action Amendment Response filed in U.S. Appl. No. 14/320,479 dated Jan. 12, 2017 in 17 pages.
Final Office Action received in U.S. Appl. No. 14/320,479 dated Feb. 7, 2017 in 12 pages.
Final Office Action and Request Under AFCP 2.0 Amendment Response filed in U.S. Appl. No. 14/320,479 dated Apr. 7, 2017 in 12 pages.
Notice of Allowance received in U.S. Appl. No. 14/320,479 dated Apr. 25, 2017 in 16 pages.
Interview Summary U.S. Appl. No. 14/320,479 dated Jun. 21, 2017 in 2 pages.
Response to Notice to File Corrected Application Papers and Amendment After Notice of Allowance Under 37 C.F.R. 1.312 filed in U.S. Appl. No. 14/320,479 dated Jul. 17, 2017 in 14 pages.
Response to 312 Amendment received in U.S. Appl. No. 14/320,479 dated Aug. 2, 2017 in 2 pages.
Preliminary Amendment and RCE received in U.S. Appl. No. 14/320,479 dated Aug. 14, 2017 in 11 pages.
Notice of Allowance received in U.S. Appl. No. 14/320,479 dated Aug. 24, 2017 in 10 pages.
Response to Notice to File Corrected Application Papers and Amendment After Notice of Allowance Under 37 C.F.R. 1.312 filed in U.S. Appl. No. 14/320,479 dated Oct. 9, 2017 in 4 pages.
Interview Summary U.S. Appl. No. 14/320,479 dated Jan. 17, 2018 in 2 pages.
Non-Final Office Action received in U.S. Appl. No. 14/497,070 dated Feb. 22, 2017 in 6 pages.
Restriction Requirement received in U.S. Appl. No. 15/639,100 dated Sep. 27, 2018 in 6 pages.
Restriction Requirement received in U.S. Appl. No. 15/639,100 dated Oct. 15, 2018 in 3 pages.
Non-Final Office Action received in U.S. Appl. No. 15/639,100 dated Jan. 23, 2019 in 69 pages.
Non-Final Office Amendment Response filed in U.S. Appl. No. 15/639,100 dated Apr. 22, 2019 in 9 pages.
Final Office Action received in U.S. Appl. No. 15/639,100 dated Jul. 10, 2019 in 12 pages.
Final Office Action Amendment Response filed in U.S. Appl. No. 15/639,100 dated Aug. 20, 2019 in 6 pages.
Notice of Allowance received in U.S. Appl. No. 15/639,100 dated Sep. 5, 2019 in 9 pages.
Notice of Non-Compliant Amendment received Mar. 9, 2010 in U.S. Appl. No. 12/454,799 in 2 pages.
Response to Notice of Non-Compliant Amendment filed on Mar. 12, 2010 in U.S. Appl. No. 12/454,799 in 6 pages.
Notice of Non-Compliant Amendment received Dec. 7, 2010 in U.S. Appl. No. 12/454,743 in 5 pages.
Comments on Reasons for Notice of Allowance and Summary of Interview filed Jul. 13, 2012 in U.S. Appl. No. 12/454,743 in 4 pages.
Comments in Response to Notice of Allowance filed Sep. 11, 2019 in U.S. Appl. No. 15/639,100 in 6 pages.
Restriction Requirement Received May 23, 2016 in U.S. Appl. No. 14/320,479 in 7 pages.
Response to Restriction Requirement filed Jul. 19, 2016 in U.S. Appl. No. 14/320,479 in 2 pages.
Comments on Statements of Reasons for Allowance filed Nov. 17, 2017 in U.S. Appl. No. 14/320,479 in 3 pages.
Notice to Filed Corrected Application Papers Received on Aug. 16, 2017 in U.S. Appl. No. 14/320,479 in 3 pages.
Notice to Filed Corrected Application Papers Received on May 22, 2017 in U.S. Appl. No. 14/320,479 in 3 pages.
Interview summary Received Mar. 29, 2017 in U.S. Appl. No. 14/033,081 in 3 pages.
Comments on Reasons for Allowance filed Jan. 7, 2015 in U.S. Appl. No. 13/186,315 in 2 pages.
Summary of interview filed Jan. 7, 2015 in U.S. Appl. No. 13/186,315 in 3 pages.
Advisory Action Received Sep. 9, 2014 in U.S. Appl. No. 13/186,315 in 6 pages.
Amendment with Request for Continued Examination filed Apr. 22, 2014 in U.S. Appl. No. 13/186,331 in 11 pages.
Notice of Allowance Received Jul. 1, 2014 in U.S. Appl. No. 13/186,331 in 8 pages.
Comments on Reasons for Allowance filed Sep. 23, 2014 in U.S. Appl. No. 13/186,331 in 2 pages.
Advisory Action Received Mar. 31, 2016 in U.S. Appl. No. 13/186,228 in 8 pages.
Summary of interview filed Feb. 6, 2017 in U.S. Appl. No. 13/186,228 in 2 pages.
Comments on Reasons for Allowance filed Oct. 23, 2017 in U.S. Appl. No. 13/186,228 in 3 pages.

\* cited by examiner

Stage 1: Target protein detection using primary antibody labeled with hairpin probe that sequesters an HCR initiator Target Stage 2: Probe activation using unstructured trigger oligo HCR hairpins Tethered fluorescent HCR amplification polymer Stage 3: Signal amplification using HCR (a) Scheme E: Secondary antibody labeled with unstructured HCR initiator (b) Scheme F: Secondary antibody labeled with HCR hairpin Stage 3: Probe activation using unstructured HCR initiator HCR initiator I1

Stage 4: Signal amplification using HCR

HCR hairpins
H1
H2

Tethered fluorescent HCR amplification polymer

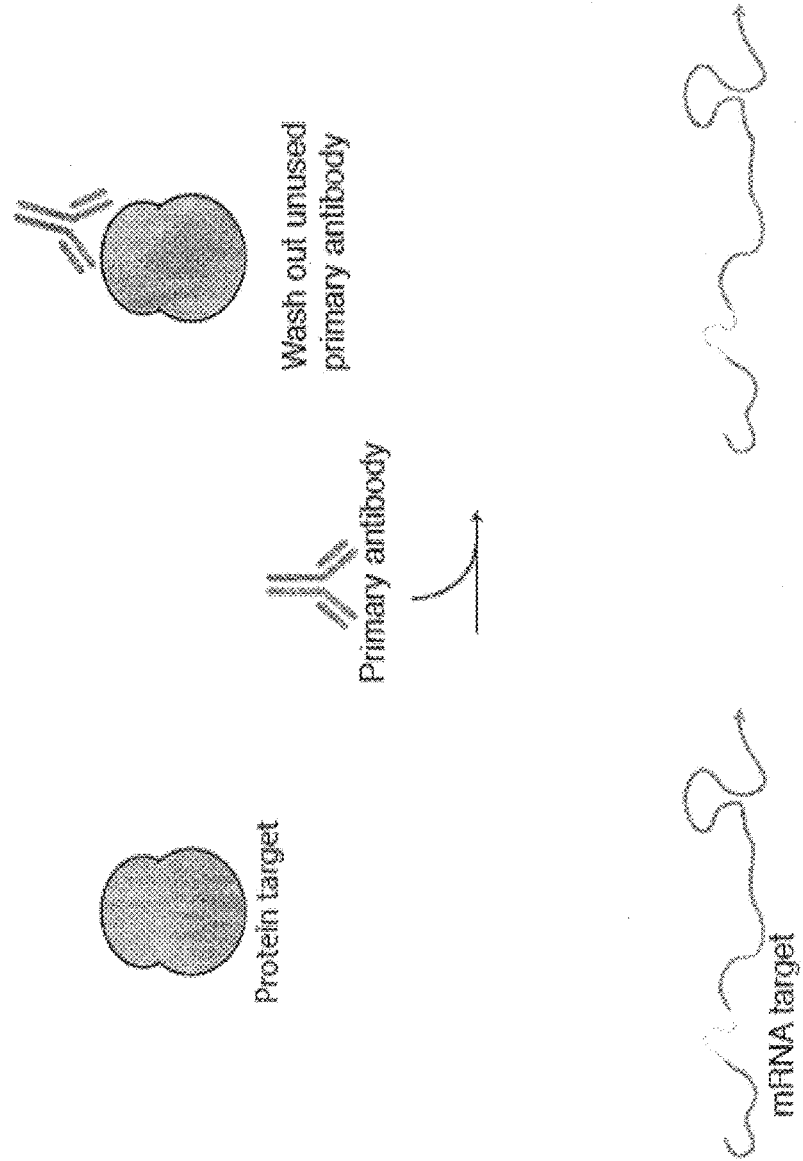

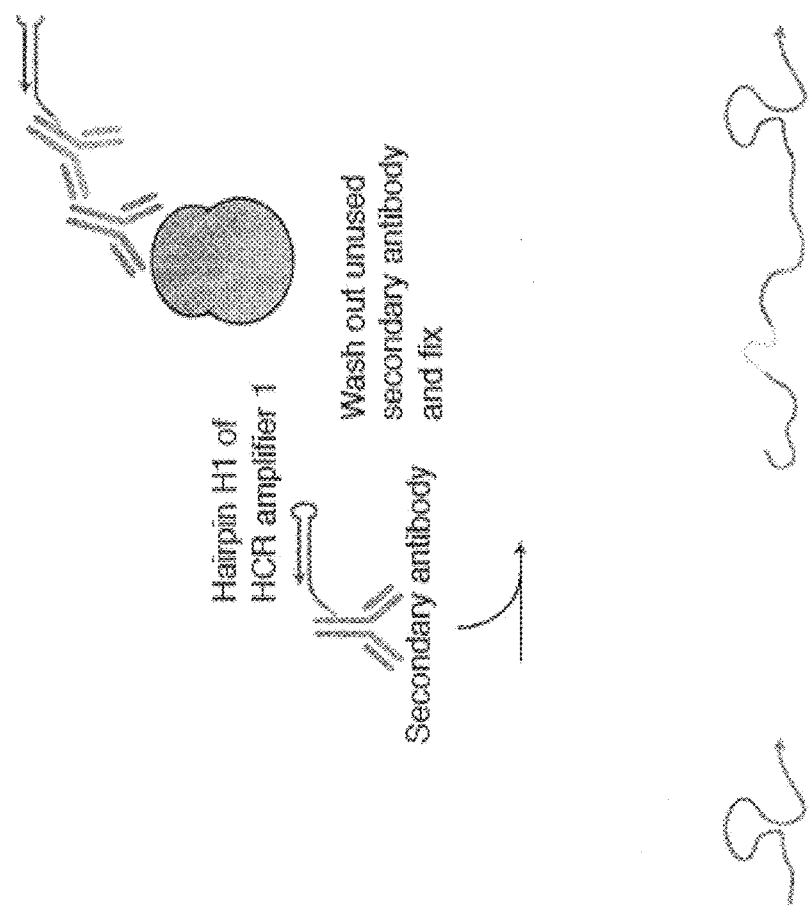

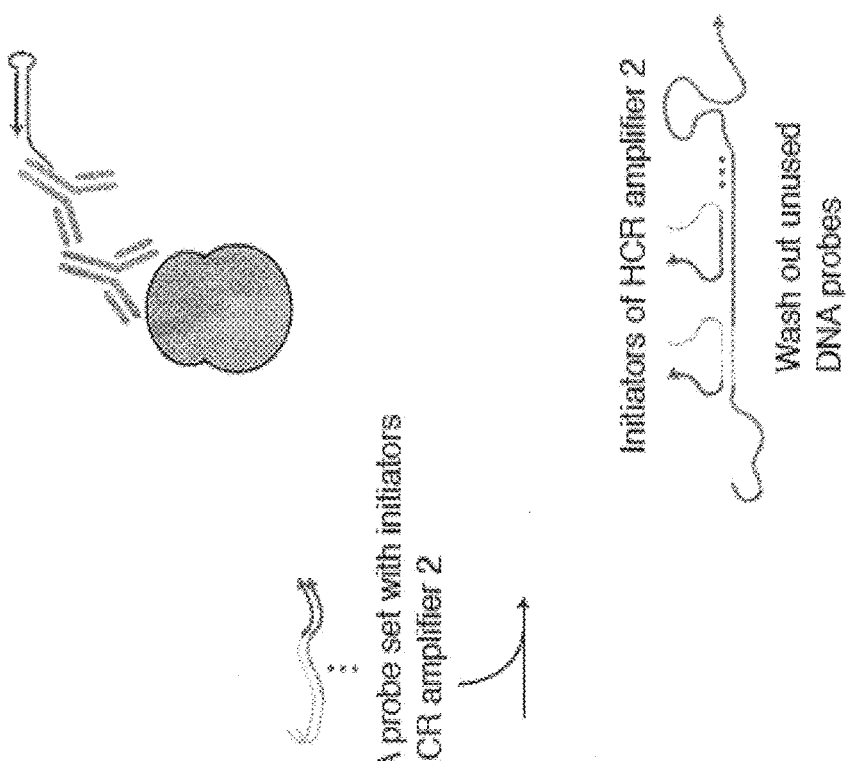

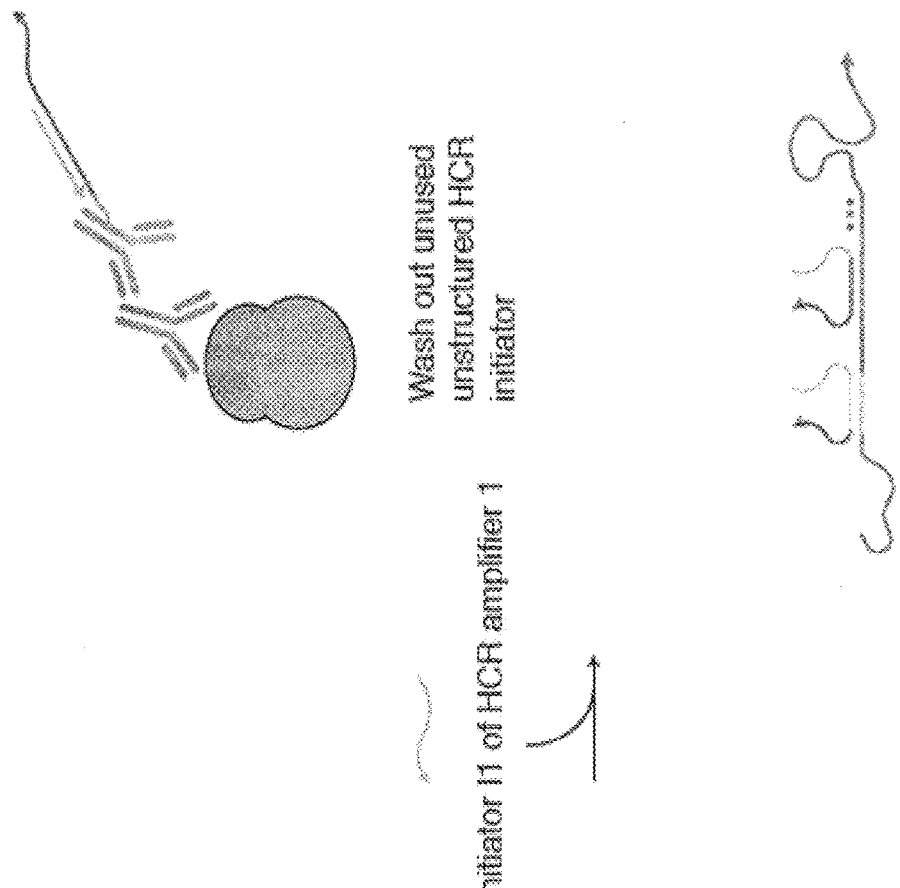

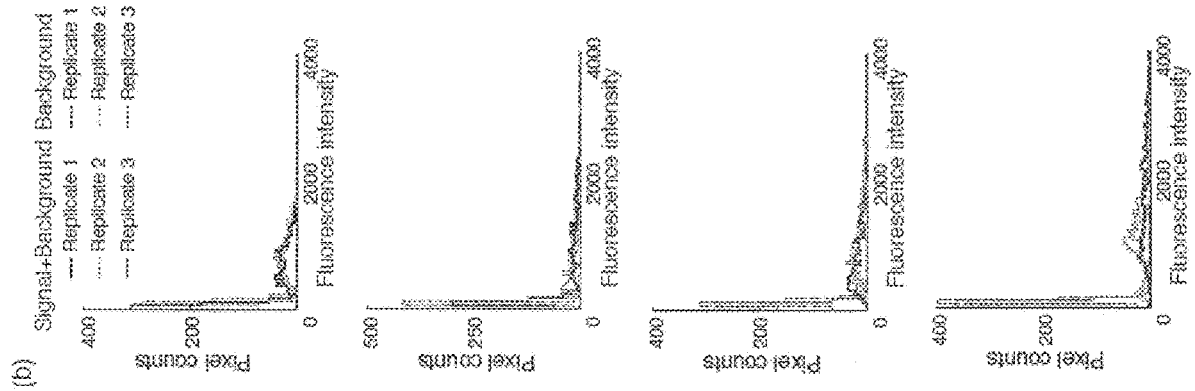

IMMUNOHISTOCHEMISTRY VIA HYBRIDIZATION CHAIN REACTION

INCORPORATION BY REFERENCE TO ANY PRIORITY APPLICATIONS

This Application claims priority to U.S. Provisional Patent Application No. 62/381,474 filed Aug. 30, 2016, the disclosure of which is hereby incorporated by reference in its entirety herein.

STATEMENT REGARDING FEDERALLY SPONSORED R&D

This invention was made with government support under Grant No. EB006192 awarded by the National Institutes of Health, under Grant No. CCF1317694 awarded by the National Science Foundation, and under Grant No. HR0011-17-2-0008 awarded by the Defense Advanced Research Projects Agency. The government has certain rights in the invention.

BACKGROUND

Field

The present invention relates generally to methods of hybridization chain reaction (HCR).

Description of the Related Art

Hybridization chain reaction is a method for the triggered self-assembly of nucleic acid molecules starting from metastable hairpin monomers. Metastable hairpin monomers undergo a chain reaction of hybridization events to form a nicked double stranded amplification polymer when triggered by a nucleic acid initiator strand. The hairpin monomers store the energy to drive the polymerization process in their single stranded loops and toeholds.

SUMMARY

In some embodiments, a method is provided. The method comprises providing a probe comprising a target-binding region linked to a structured nucleic acid region, wherein the structured nucleic acid region sequesters an HCR initiator. The method further includes adding a trigger oligo, wherein the trigger oligo binds to the structured nucleic acid region, which changes conformation to expose the initiator; and amplifying from the initiator using HCR.

In some embodiments, a method is provided. The method comprises providing: at least one target-binding moiety labeled with a modified HCR hairpin; a target molecule; a trigger oligo; and a pair of polymerizing HCR hairpins. The trigger oligo binds to the modified HCR hairpin and the pair of polymerizing HCR hairpins do not bind to each other or directly to the modified HCR hairpin unless the trigger oligo has first bound to the modified HCR hairpin. The method further includes performing HCR to produce a polymer; and detecting a signal from the polymer.

In some embodiments, a method is provided. The method comprises providing: at least one target-binding moiety labeled with a structured probe sequestering an HCR initiator; a target molecule; a trigger oligo; and at least a pair of polymerizing HCR hairpins, wherein the trigger oligo binds to the structured probe and the pair of polymerizing HCR hairpins do not bind to each other or to the sequestered HCR initiator, unless the trigger oligo has first bound to the structured probe. The method further includes performing HCR; and detecting a signal.

BRIEF DESCRIPTION OF THE DRAWINGS

FIG. 1A depicts an HCR mechanism. FIG. 1B depicts an antibody driven binding embodiment, which includes an HCR amplification stage. FIG. 1C denotes a multiplexed experimental timeline of some embodiments of the process, simultaneously adding initiator-labeled antibodies for each of three targets, washing out unbound antibodies, simultaneously adding hairpin monomers for each of three HCR amplifiers, washing out unpolymerized hairpin monomers.

FIG. 2A depicts scheme A. FIG. 2B depicts scheme B. FIG. 2C depicts scheme C. FIG. 2D depicts scheme D. These embodiments can be combined or modified as provided herein. The figures depict both generic and specific embodiments.

FIG. 3A depicts scheme E. FIG. 3B depicts scheme F. FIG. 3C depicts scheme G. FIG. 3D depicts scheme H. These embodiments can be combined or modified as provided herein. The figures depict both generic and specific embodiments.

DETAILED DESCRIPTION

Figure 1A:
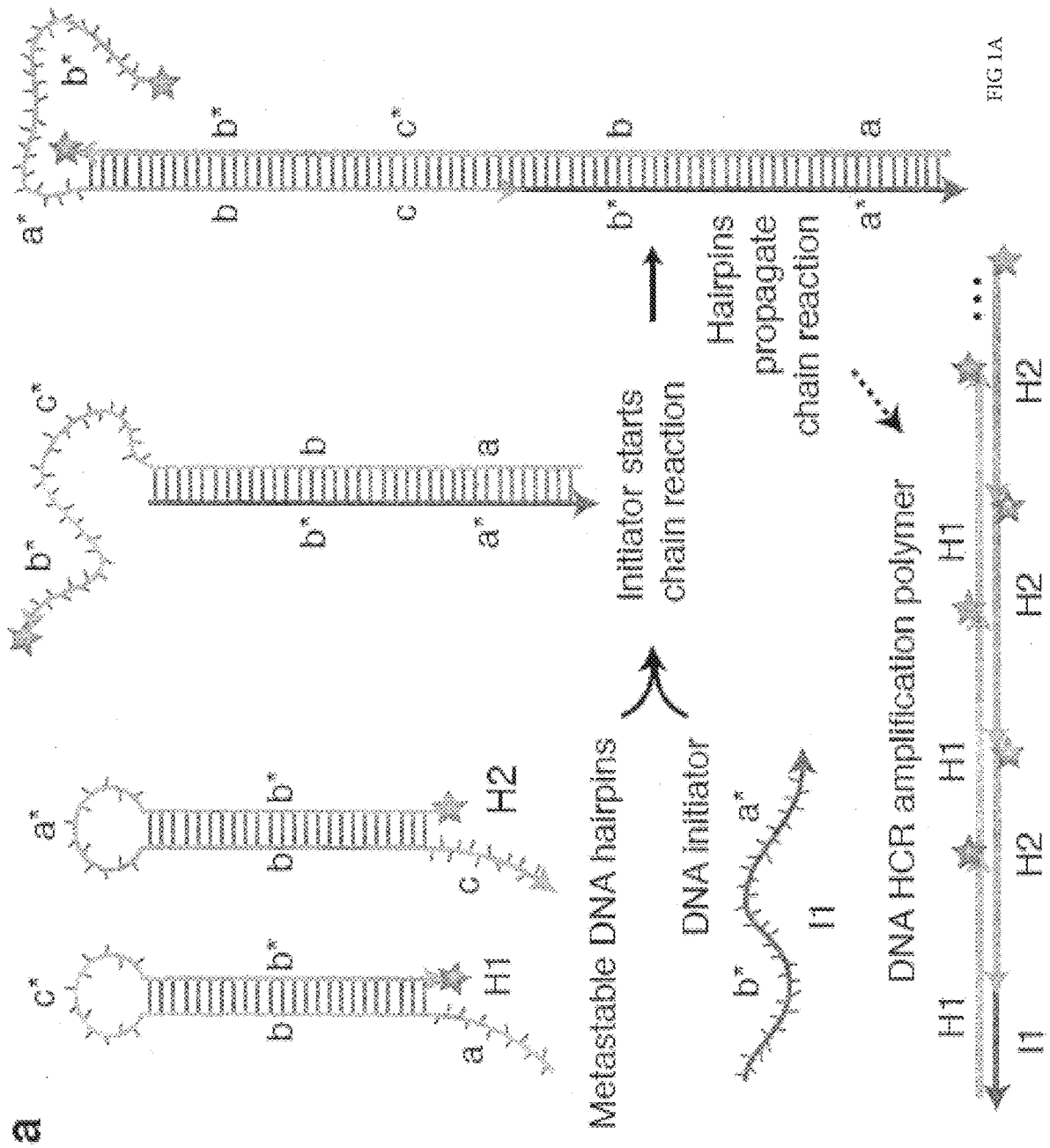
FIGS. 1A-1C depict in situ amplification via hybridization chain reaction (HCR).

Provided herein are embodiments employing immunohistochemistry and hybridization chain reactions. By combining these techniques, superior processes and kits can be obtained for the detection of various targets. In some embodiments, in order to reduce any inadvertent signaling that can occur in a sample, the IHC component of the process is distinguished or separated from the HCR side of the process. This can be achieved in a number of ways, for example, by sequestering an initiator component within (or modifying it or removing it) from the antibody linked component. Thus reducing any inadvertent HCR amplification (or background HCR reactions). In some embodiments, this is done via a trigger oligo, which binds to the modified HCR hairpin on the antibody, so as to then expose the initiator, which can then trigger HCR signal amplification (e.g., FIG. 3C). Other embodiments are provided herein as well. In some embodiments, the IHC aspect can involve a primary antibody assay or a secondary antibody assay (where the modified HCR hairpin is linked to the secondary antibody, in some embodiments). In some embodiments, any of the methods provided in one or more of the figures can be employed to reduce background or inadvertent triggering events.

By way of context, Hybridization Chain Reaction (HCR) is a method for the triggered hybridization of nucleic acid molecules starting from metastable hairpin monomers or other metastable nucleic acid structures. See, for example, Dirks, R. and Pierce, N. Proc. Natl. Acad. Sci. USA 101(43): 15275-15278 (2004), and U.S. patent application Ser. No. 11/087,937, filed Mar. 22, 2005, U.S. Pat. No. 8,105,778, Jan. 31, 2012, and U.S. Pat. No. 8,507,204, Aug. 13, 2013, each of which is incorporated herein by reference in its entirety. HCR does not require any enzymes and can operate isothermally. Traditionally, HCR ISH involves an unstructured nucleic acid probe that carries an exposed HCR initiator or a structured nucleic acid probe that initially sequesters an HCR initiator but changes conformation to expose an HCR initiator upon binding to a nucleic acid target. In either scenario, an exposed HCR initiator will trigger polymerization of metastable HCR monomers to form an HCR amplification polymer. By contrast, some of the present embodiments require an additional process or component before polymerization will occur.

For example, some embodiments provided herein add an additional step or component, such as a trigger oligo, which is used to activate a structured nucleic acid probe carried by an antibody probe. In some embodiments, the structured nucleic acid probe is a hairpin probe that initially sequesters an HCR initiator that is exposed upon binding of the trigger oligo to the input domain of the hairpin probe, enabling the initiator to trigger HCR signal amplification. Prior techniques did not involve a trigger oligo as a part of the target detection and signal amplification cascade. With prior HCR-ISH techniques, in a first scenario, an unstructured nucleic acid probe carries an exposed HCR initiator that is accessible to trigger HCR signal amplification. Hence, if the probe binds non-specifically in the sample, it will nonetheless trigger HCR signal amplification and lead to generation of amplified background. In a second scenario, a structured nucleic acid probe initially sequesters an HCR initiator that is then exposed when the probe selectively hybridizes to the nucleic acid target molecule, thus activating the probe so that it can trigger HCR signal amplification. Hence, if the probe binds non-specifically in the sample, it will remain inactive and not lead to generation of amplified background. With prior HCR-IHC techniques, an antibody probe carries an exposed HCR initiator that is accessible to trigger HCR signal amplification. Hence, if the antibody binds non-specifically in the sample, it will nonetheless trigger HCR signal amplification and lead to generation of amplified background. Moreover, the unstructured initiator oligos labeling the antibody increase the stickiness of the antibody probe, inhibiting penetration into the sample and increasing non-specific binding. Labeling the antibody probe with multiple exposed HCR initiators in order to increase the signal generated per target molecule further increases the stickiness of the antibody probe due to multivalent non-specific base-pairing between the sample and the multiple exposed HCR initiators, thus further increasing non-specific binding and reducing sample penetration.

In some embodiments, the use of an antibody probe carrying a hairpin probe sequestering an HCR initiator reduces non-specific binding of the antibody probe and increases the ability of the antibody probe to penetrate the sample. Compared to an exposed HCR initiator, the duplex stem of the hairpin probe reduces the availability of bases to base-pair non-specifically in the sample, thus reducing non-specific binding and increasing sample penetration. In some embodiments, after an antibody probe penetrates the sample and binds selectively to a target within the sample, the hairpin probe labeling the antibody is activated using a trigger oligo that binds to the hairpin probe to expose an HCR initiator, enabling subsequent HCR signal amplification. In some embodiments, an antibody probe is labeled with multiple structured nucleic acid probes such that it penetrates the sample and binds selectively to the target; subsequently each structured nucleic acid probe is activated by a trigger oligo, in each case exposing an HCR initiator; subsequently each exposed HCR initiator triggers self-assembly of an HCR amplification polymer, leading to multiple HCR amplification polymers tethered to the same antibody probe, thus increasing the signal generated per target molecule.

In some embodiments, the nucleic acid probe attached to the antibody can be any nucleic acid that exposes an HCR initiator upon selective hybridization to the trigger oligo. The trigger oligo can, in turn, include a first HCR initiator, which would otherwise be washed out of the sample, but upon selective binding to the nucleic acid probe, exposes a second HCR initiator that triggers HCR signal amplification, leading to self-assembly of an HCR amplification polymer tethered to the antibody.

By way of further context, an HCR amplifier comprises of two kinetically trapped nucleic acid hairpin monomers (H1 and H2) that co-exist metastably in the absence of a cognate initiator strand (I1 with sequence domains 'b*-a*'; FIG. 1A). Arrival of the initiator triggers a chain reaction in which H1 and H2 hairpin monomers sequentially nucleate and open to assemble into a long nicked double-stranded amplification polymer (Dirks and Pierce 2004). Each HCR hairpin monomer includes an input domain with an exposed single-stranded toehold and an output domain with a single-stranded toehold sequestered in the hairpin loop. Hybridization of the initiator to the input domain of H1 (FIG. 1A, 'a-b') opens the hairpin monomer to expose its output domain (FIG. 1A, 'c*-b*'). Hybridization of this output domain to the input domain of H2 (FIG. 1A, 'c-b') opens the hairpin monomer to expose an output domain (FIG. 1A, 'b*-a*') identical in sequence to the initiator. Regeneration of the initiator sequence provides the basis for a chain reaction of alternating H1 and H2 polymerization steps leading to formation of a nicked double-stranded polymer.

Figure 1B:
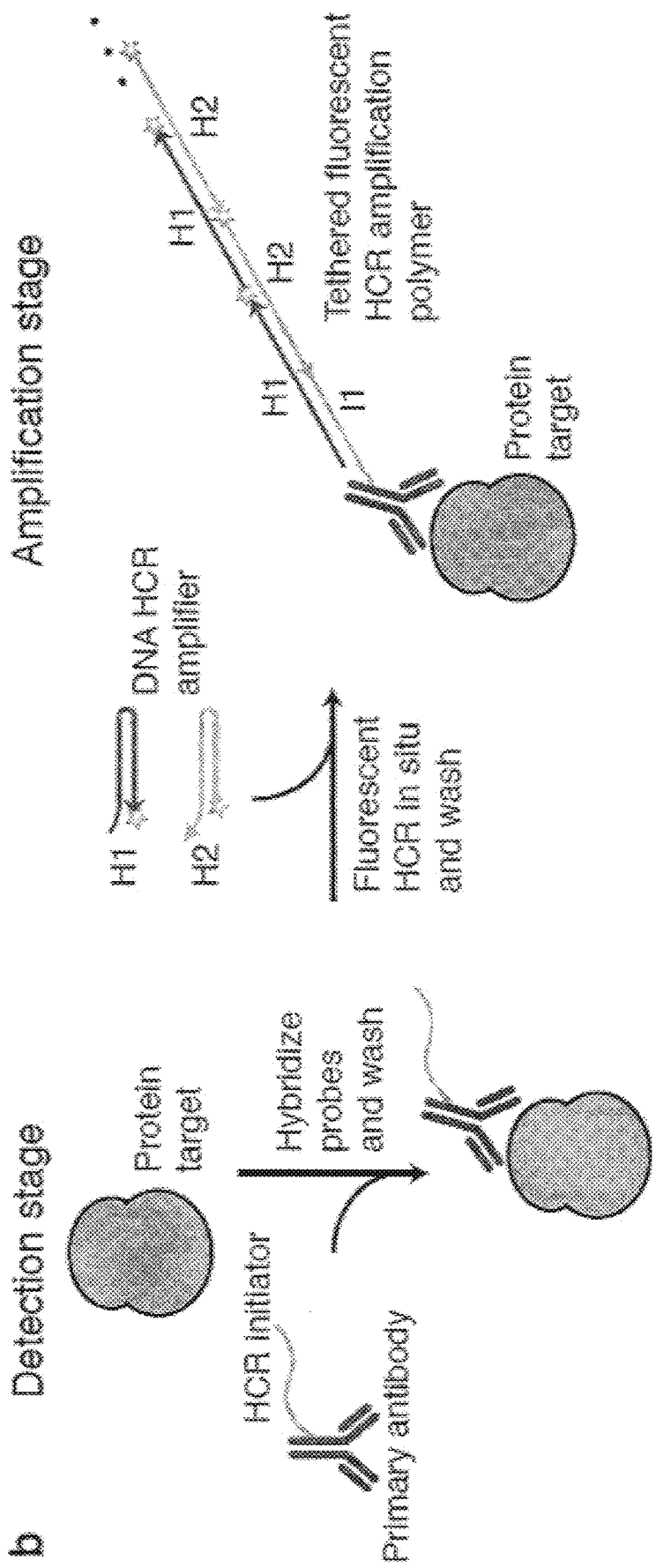

Using HCR-IHC, antibody probes that selectively bind protein targets carry DNA HCR initiators that trigger chain reactions in which metastable fluorophore-labeled DNA hairpins self-assemble into tethered fluorescent amplification polymers (FIG. 1B). The same IHC protocol can be used independent of the number of targets (FIG. 1C): in the detection stage, antibody probes for all targets bind in parallel; in the amplification stage, orthogonal HCR amplifiers carrying spectrally distinct fluorophores operate in parallel for all targets.

HCR draws on principles from the emerging disciplines of molecular programming and dynamic nucleic acid nanotechnology to provide isothermal enzyme-free signal amplification in diverse technological settings (Zhang et al. 2013; Jung and Ellington 2014; Wang et al. 2014; Ikbal et al. 2015) and it is particularly well-suited to the demands of in situ amplification (Choi et al. 2010; Choi et al. 2014). First, HCR is programmable, providing the basis for straightforward multiplexing using orthogonal amplifiers that operate independently and carry spectrally distinct fluorophores. Use of a protocol independent of the number of target species is convenient for any sample, but essential for delicate samples such as sea urchin embryos that are easily damaged during serial multiplexing protocols. Second, HCR hairpins do not self-assemble until they encounter a probe carrying the cognate initiator, enabling deep sample penetration prior to growth of bright amplification polymers at the site of target molecules. The fact that the amplification reagents are structured hairpin monomers with a duplex stem reduces the potential for non-specific hybridization within the sample and also increases the ease of engineering multiple orthogonal amplifiers. The fact that amplification polymers carry up to hundreds of fluorophores (Choi et al. 2014) makes it possible to achieve high signal-to-background even when autofluorescence is high (e.g., in whole-mount vertebrate embryos (Choi et al. 2014; Huss et al. 2015; McLennan et al. 2015) or in bacteria contained within environmental samples or other organisms (Rosenthal et al. 2013; Nikolakakis et al. 2015; Yamaguchi et al. 2015)). Third, HCR amplification polymers remain tethered to their initiating probes, preventing signal from diffusing away from targets. Fourth, previously validated HCR amplifiers (Choi et al. 2014) can be used for new studies without modification. In some embodiments, all that is needed to map a new target molecule is an antibody probe labeled with a structured nucleic acid probe sequestering an initiator for a previously validated HCR amplifier. In this scenario, it is not necessary to engineer a new HCR amplifier for each new target molecule.

DEFINITIONS AND EMBODIMENTS

The term "target binding region" refers to a region in an antibody or fragment thereof that binds to a target molecule.

The term "structured nucleic acid molecule" refers to a nucleic acid molecule that forms intramolecular base pairs, such as a hairpin probe, which contains a duplex stem comprising intramolecular base pairs. The term "unstructured nucleic acid molecule" refers to a nucleic acid molecule that predominantly does not form intramolecular base pairs, such that all of the bases in the molecule are predominantly available to base-pair.

The term "HCR initiator" refers to a nucleic acid region that can trigger the polymerization of two metastable HCR hairpin monomer species to form an HCR amplification polymer. An exposed HCR initiator is functional and triggers polymerization of the metastable HCR hairpin monomers under polymerizing conditions. A sequestered HCR initiator is non-functional and does not trigger polymerization of the metastable HCR hairpins monomers under polymerizing conditions. A sequestered HCR initiator (hence, initially non-functional) can be exposed (hence, becoming functional) upon binding of another molecule to the sequestering molecule.

The term "trigger oligo" refers to a nucleic acid molecule that binds to a structured nucleic acid probe carried by a target-binding probe (for example, an antibody) such that binding of the trigger oligo to the structured nucleic acid probe exposes a functional HCR initiator. In some embodiments, the initiator is previously sequestered by the structured nucleic acid probe. In some embodiments, the trigger oligo comprises a functional HCR initiator. In some embodiments, the trigger oligo binds to the nucleic acid probe associated with the target-binding probe and thereby exposes a functional HCR initiator.

The term "hairpin probe" refers to a nucleic acid strand that forms intramolecular base pairs to yield a duplex stem with a single-stranded toehold at one end and a single-stranded hairpin loop at the other.

The term "toehold" refers to nucleation site of a domain comprising a nucleic acid sequence designed to initiate hybridization of the domain with a complementary nucleic acid sequence. The secondary structure of a monomer may be such that the toehold is exposed or sequestered. For example, in some embodiments, the secondary structure of the toehold is such that the toehold is available to hybridize to a complementary nucleic acid (the toehold is "exposed," or "accessible"), and in other embodiments, the secondary structure of the toehold is such that the toehold is not available to hybridize to a complementary nucleic acid (the toehold is "sequestered," or "inaccessible"). If the toehold is sequestered or otherwise unavailable, the toehold can be made available by some event such as, for example, the opening of the hairpin of which it is a part. When exposed, a toehold is configured such that a complementary nucleic acid sequence can nucleate at the toehold. In some embodiments, nucleation of a complementary nucleic acid sequence at an exposed toehold initiates branch migration that opens up the hairpin of a hairpin monomer.

The term "stem section" refers to a region on a hairpin probe that hybridizes to a complementary portion of the probe ("complement to the stem section") to form a duplex stem.

The term "input domain" refers to a region of a hairpin probe that comprises the "toehold" and "stem section".

The term "output domain" refers to a region of a hairpin probe that comprises the "hairpin loop" and "complement to the stem section".

The term "hairpin loop" refers to a single-stranded region that loops back on itself and is closed by a base pair.

The term "complement to the stem section" refers to a region of a hairpin probe that hybridizes to a complementary portion of the same probe ("stem section") to form a duplex stem.

The term "label binding site" refers to a region on a HCR hairpin monomer that is complementary to the "complement to the label binding site."

The term "complement to the label binding site" refers to a region on a HCR hairpin monomer that is complementary to the "label binding site."

The term "reporter molecule" refers to a molecule that can be detected.

The term "HCR hairpin monomer" when used without further modification, refers to a monomer that is capable of performing HCR signal amplification.

The term "modified HCR hairpin monomer" as used herein refers to an HCR hairpin monomer with a modified input domain comprising a modified toehold sequence and a sequestered HCR initiator within its output domain, such that it is not capable of trigger HCR on its own, but exposes a functional HCR initiator upon binding of a trigger oligo to the input domain, thus enabling triggering of HCR signal amplification.

The term "modified input domain" refers to an input domain that has a modified toehold sequence.

The term "modified toehold sequence" refers a toehold sequence that is not a nucleation site for the complement to a standard toehold sequence.

The term "nucleic acid" refers to DNA, RNA, 2'OMe-RNA, LNA, or any DNA analog, RNA analog, or synthetic polymer capable of base-pairing.

Methods

Figure 2A:
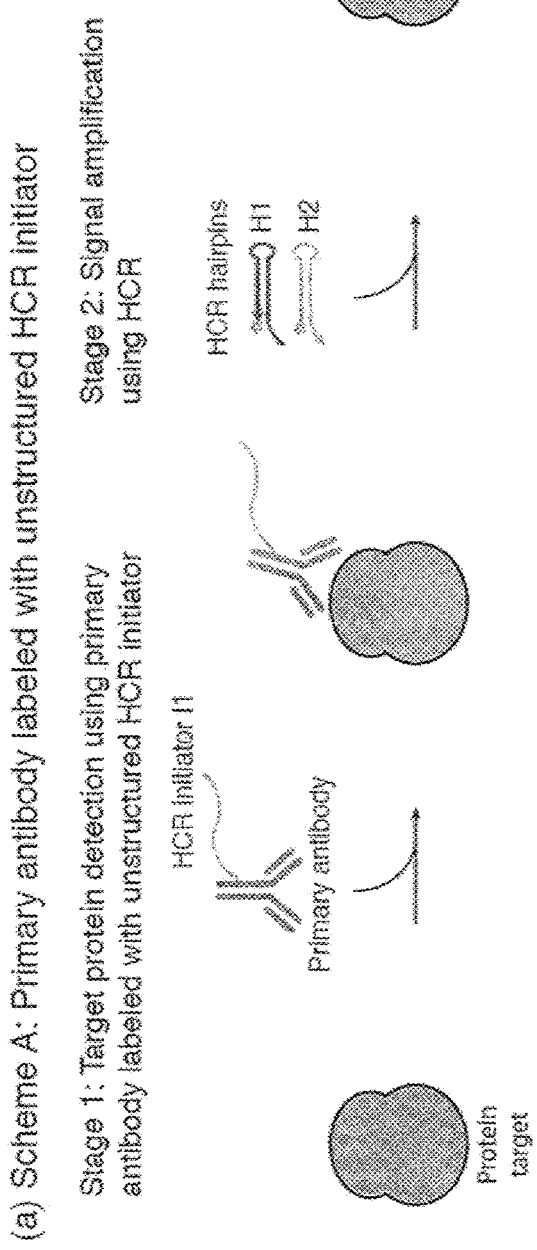
FIGS. 2A-2D depicts some embodiments of HCR immunohistochemistry (HCR-IHC) using oligo-labeled primary antibodies.
Figure 2B:
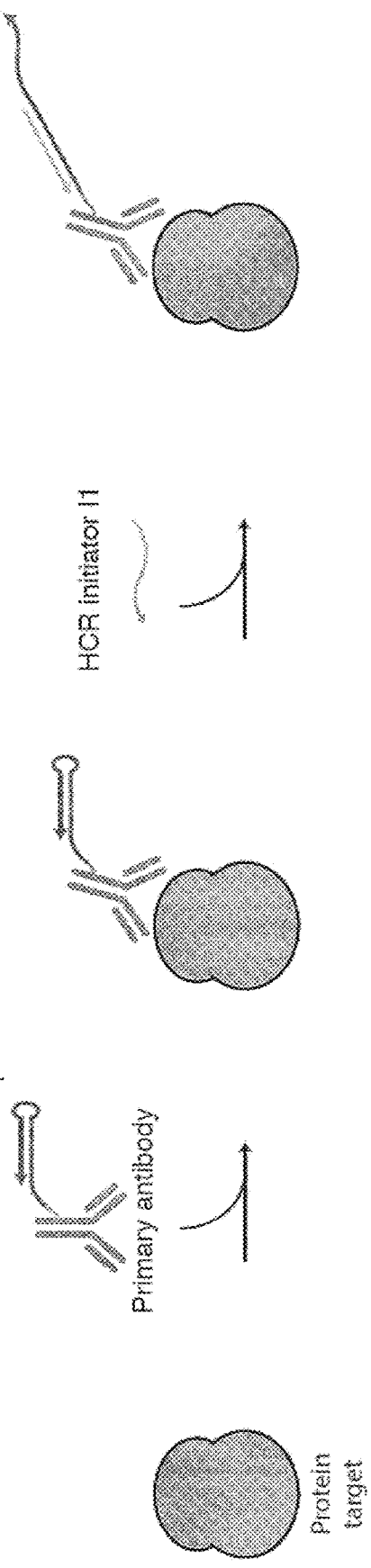
Figure 2B:
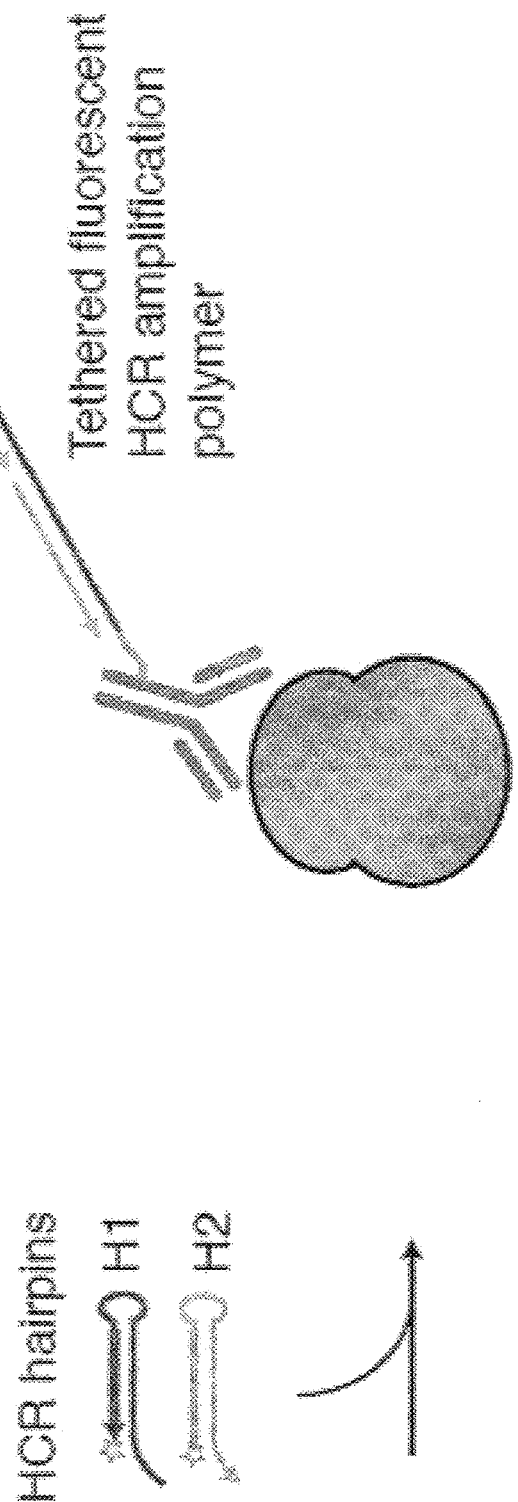
Figure 2C:
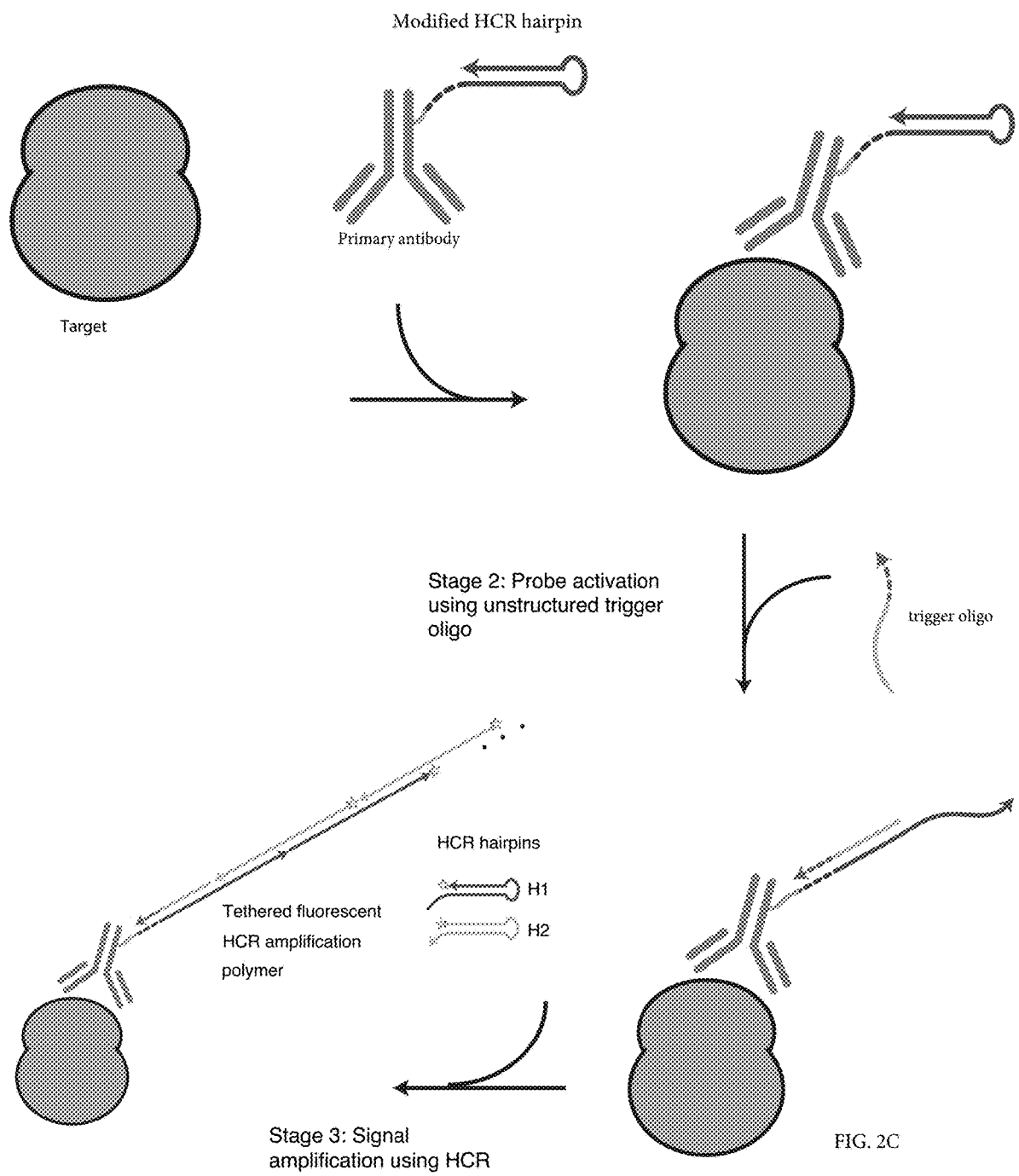
Figure 2D:
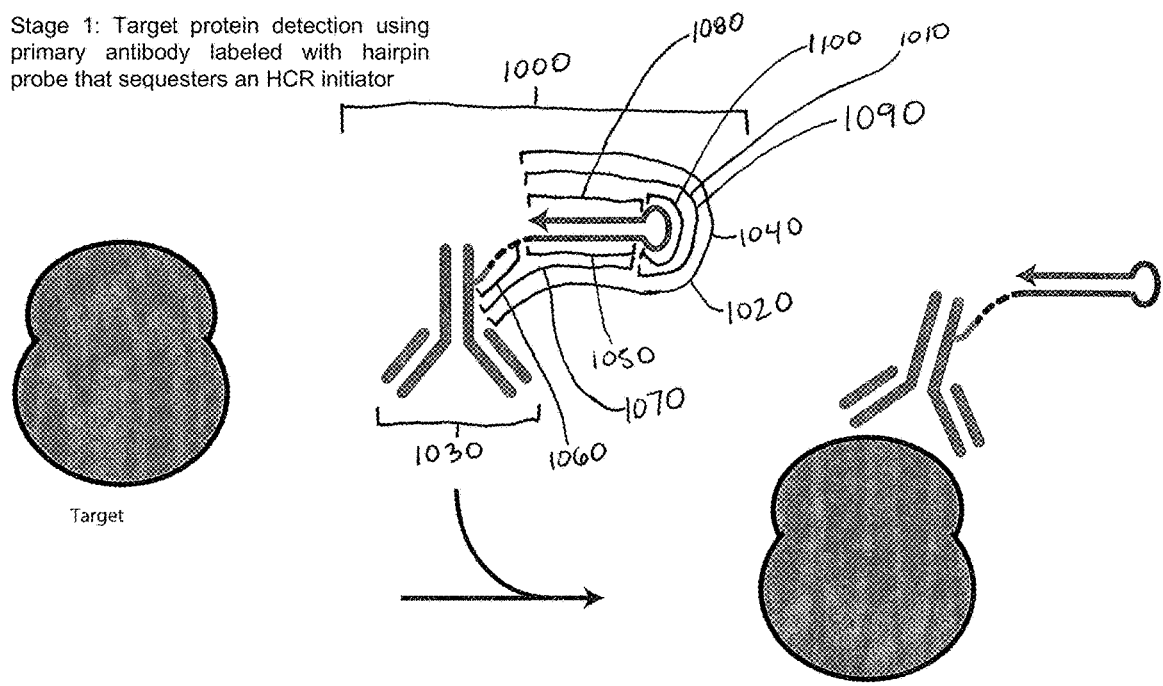
Figure 2D:
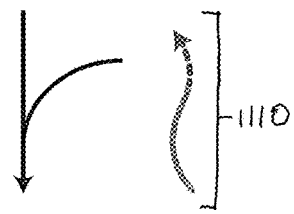
Figure 2D:
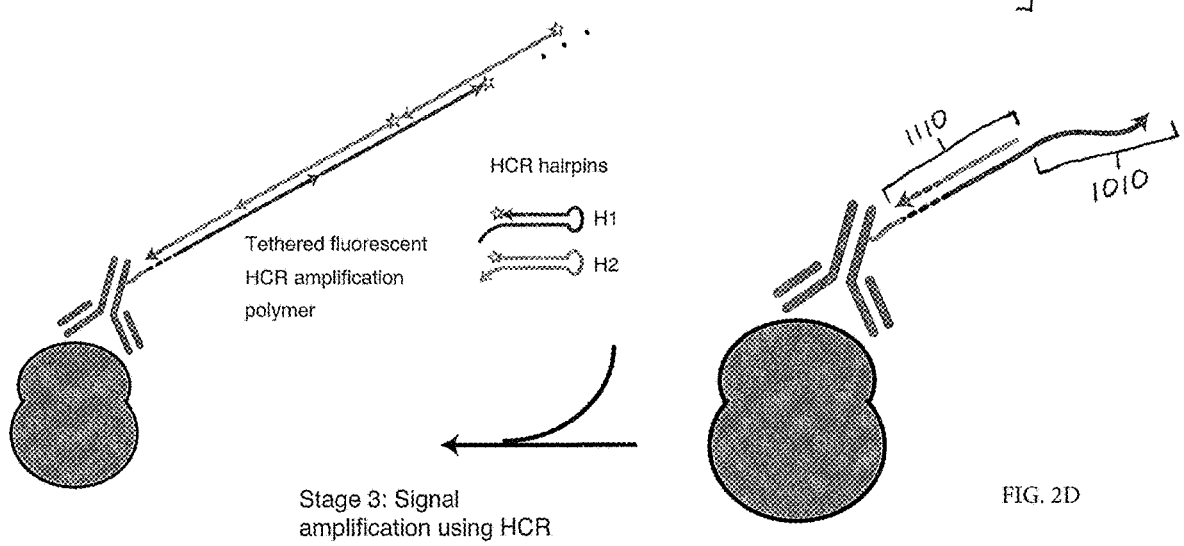

In some embodiments, a method is provided as depicted FIG. 2D. In some embodiments, a probe 1000 is provided, comprising a target binding region 1030 (that can be, e.g., a primary antibody, but is not so limited in all embodiments)

that is linked to a structured nucleic acid probe 1040 (that can be, e.g., a hairpin probe, but is not so limited in all embodiments) that sequesters an HCR initiator 1010. In some embodiments, when the HCR initiator is sequestered, it cannot effectively trigger HCR signal amplification. In some embodiments, the structured nucleic acid probe 1040 is a hairpin probe 1020 that comprises an input domain 1070 and an output domain 1090. In some embodiments, the input domain 1070 comprises a toehold 1060 and a stem section 1050. In some embodiments, the output domain 1090 comprises a complement to the stem section 1080 and a hairpin loop 1100. In some embodiments, the output domain 1090 comprises the HCR initiator 1010. In some embodiments, the HCR initiator is the whole output domain. In some embodiments, the HCR initiator is only a portion of the output domain. Addition of a trigger oligo 1110 results in binding of the trigger oligo 1110 to the hairpin probe 1020 at the toehold 1060 and stem section 1050. This results in a conformation change of the hairpin probe 1020, which exposes the HCR initiator 1010. Exposure of the HCR initiator 1010 enables triggering of HCR signal amplification in which metastable HCR hairpin monomers self-assemble to form an HCR amplification polymer. Additional embodiments of FIG. 2D are described below.

In some embodiments, a method is provided that comprises providing a probe comprising a target-binding region linked to a structured nucleic acid region. The structured nucleic acid region sequesters an HCR initiator. One then adds a trigger oligo. The trigger oligo binds to the structured nucleic acid region, which changes conformation to expose the initiator. One then amplifies from the initiator using HCR. Washes can occur such that unbound probe and unbound trigger oligo are each removed prior to the next step.

In some embodiments, a method is provided comprising providing: at least one target-binding moiety labeled with a modified HCR hairpin probe; a target molecule; a trigger oligo; and a pair of metastable HCR hairpins monomer species. The trigger oligo binds to the modified HCR hairpin and the pair of metastable HCR hairpin monomers do not bind directly to the modified HCR hairpin unless the trigger oligo has first bound to the modified HCR hairpin probe; performing HCR signal amplification to produce an HCR amplification polymer; and detecting a signal from the polymer. Washes can occur such that unbound probe, unbound trigger oligo, and unbound HCR hairpin monomers are each removed prior to the next step.

In some embodiments, a method is provided comprising providing: at least one target-binding moiety labeled with a structured probe sequestering an HCR initiator; a target molecule; a trigger oligo; and at least a pair of metastable HCR hairpin monomer species. The trigger oligo binds to the structured probe and the pair of metastable HCR hairpin monomer species do not bind to the structured probe, unless the trigger oligo has first bound to the structured probe to expose the HCR initiator. The exposed HCR initiator then triggers HCR signal amplification, generating a detectable signal when the target molecule is present. The amplified signal is then detected. Washes can occur such that unbound probe, unbound trigger oligo, and unbound metastable hairpin monomers are each removed prior to the next step.

In some embodiments, the target-binding region comprises DNA, RNA, LNA, PNA, 2'OMe-RNA, a synthetic nucleic acid analog, amino acid, or synthetic amino acid analog.

In some embodiments, the target-binding region is an antibody. In some embodiments, the antibody comprises a primary antibody. In some embodiments, the antibody further comprises a secondary antibody. In some embodiments, the antibody comprises a first antibody that binds to the target molecule, and a second antibody that binds to the first antibody, wherein the structured nucleic acid region is linked to the second antibody but is not linked to the first antibody. In some embodiments, an antibody fragment is used. In some embodiments, any molecule or structure that binds to a desired target, suitable for in vitro, in situ, ex vivo, in vivo detection, can be employed.

In some embodiments, the structured nucleic acid region comprises DNA, RNA, LNA, PNA, 2'OMe-RNA, or a synthetic nucleic acid analog. In some embodiments, the structured nucleic acid region comprises or consists of a hairpin probe. In some embodiments, the hairpin probe comprises: an input domain comprising a toehold and a stem section, and an output domain comprising a hairpin loop and a complement to the stem section, such that the exposed output domain comprises an HCR initiator. In some embodiments, the hairpin probe is an HCR hairpin monomer. In some embodiments, the hairpin probe is not an HCR hairpin monomer.

In some embodiments, the hairpin probe comprises a modified HCR hairpin monomer with a modified input domain that has a modified toehold sequence, wherein the modified HCR hairpin monomer is configured such that its output domain is a sequestered HCR initiator that does not trigger HCR, but wherein the trigger oligo hybridizes to the modified input domain to expose the HCR initiator, triggering HCR signal amplification via self-assembly of first and second HCR hairpin monomer species. In some embodiments, the hairpin probe cannot or is not configured to trigger HCR or participate within HCR signal amplification directly. Of course, with the assistance of a trigger oligo, HCR polymerization then becomes possible.

In some embodiments, the trigger oligo binds to the hairpin probe at a toehold and/or stem section, thereby changing the conformation of the hairpin probe to expose a functional HCR initiator. In some embodiments, the trigger oligo is or comprises a first HCR initiator, such that upon binding to the input domain of the hairpin probe further comprising an output domain that is or comprises a sequestered second HCR initiator, the second HCR initiator is exposed and is thus able to trigger HCR signal amplification.

In some embodiments, the trigger oligo binds to the input domain, thereby exposing the output domain which is capable of triggering HCR. In some embodiments, the trigger oligo comprises a nucleotide sequence. In some embodiments, the trigger oligo hybridizes to the probe and thereby exposes the initiator (previously sequestered within the structured probe).

In some embodiments, in any of the binding reactions described herein, binding comprises hybridization. In some embodiments, binding comprises selective protein-protein interaction. In some embodiments, binding comprises selective nucleic acid-protein interaction. In some embodiments, binding comprises ionic binding. In some embodiments, binding comprises covalent bonding.

In some embodiments, the target molecule is a protein. In some embodiments, the target molecule is a small molecule or nucleic acid. In some embodiments, the target molecule is a complex of two or more proteins, nucleic acids, and/or small molecules. In some embodiments, the target molecule comprises a nucleotide sequence. In some embodiments, the target molecule comprises an amino acid sequence. In some embodiments the target comprises a molecule or a complex of two or more molecules.

In some embodiments, HCR signal amplification is performed using at least a first and second set of HCR hairpin monomer. In some embodiments, HCR is performed using a first, second, third, and fourth set of HCR hairpin monomers. In some embodiments, HCR is performed using more than two sets of HCR hairpin monomers, for example, more than 10 sets of HCR hairpin monomers, more than 100 sets of HCR hairpin monomers, more than 1,000 sets of HCR hairpin monomers, more than 10,000 sets of HCR hairpin monomers, or 100,000 sets of HCR hairpin monomers. In some embodiments, the first and second set of HCR hairpin monomers each further comprise a reporter molecule. In some embodiments, the first and second set of HCR hairpin monomers each further comprise a label-binding site that is configured to hybridize to a complement to the label binding site, wherein the complement to the label binding site further comprises a reporter molecule. In some embodiments, the HCR monomers comprise a label-binding site.

In some embodiments, the reporter molecules are fluorescent molecules, non-fluorescent molecules, FRET molecules, or rare earth elements. In some embodiments, the reporter molecule comprises a quenched or FRET arrangement. In some embodiments, the reporter molecules are rare metal lanthanide complexes. In some embodiments, the reporter molecules are gold nanoparticles. In some embodiments the reporter molecules are dyes such as rhodamine, fluorescein, phycobiliproteins, acridines or cyanine compounds. In some embodiments, any reporter molecule whose presence or absence can be monitored can be employed. In some embodiments, the reporter molecule comprises a fluorescent molecule such as a fluorophore, or a colorimetric compound, that allows the resulting polymers to be visualized. In some embodiments, the reporter molecule is directly observable. In some embodiments, the reporter molecule is indirectly observable. In some embodiments, the reporter molecule comprises an enzyme or is enzymatic, and/or can mediate enzymatic signaling after HCR polymerization. In some embodiments, reporting is achieved by catalyzed reporter deposition ("CARD"). In some embodiments, a label binding site on one or more of the HCR hairpin monomer species can enable binding of a complement to the label binding site, wherein the complement to the label binding site carries a reporter molecule. In some embodiments, one type of reporter molecule carried by the hairpin monomers or the complement to the label binding site can mediate enzymatic signal amplification (CARD) after HCR polymerization such that a second type of reporter molecules deposited in the vicinity of HCR polymers will then be detected. In some embodiments, the reporter molecule is at least one of a luminescent molecule, FRET molecules, fluorophore/quencher molecular pairs, or other detectable markers. In some embodiments, the reporter molecule can allow for a secondary molecule (such as a secondary antibody) to be employed for detection of the polymerization event. In some embodiments, the hairpin monomers can be labeled with reporter molecules (e.g., a fluorophore and a quencher) such that hairpin monomers are quenched but that the conformation change that occurs during HCR polymerization leads to fluorescent HCR amplification polymers.

In some embodiments, each HCR amplifier comprises at least two types of kinetically trapped nucleic acid hairpin monomers that co-exist metastably in the absence of the initiator. In some embodiments, each HCR amplifier comprises more than two types of kinetically trapped nucleic acid hairpin monomers, for example, at least 10 kinetically trapped nucleic acid hairpin monomers, at least 100 kinetically trapped nucleic acid hairpin monomers, at least 1,000 kinetically trapped nucleic acid hairpin monomers, at least 10,000 kinetically trapped nucleic acid hairpin monomers, or at least 100,000 kinetically trapped nucleic acid hairpin monomers.

In some embodiments, any of the methods described herein further comprise washing away any unbound probe from a sample. In some embodiments, washing away any unbound probe requires more than one wash, for example, two washes, three washes, four washes, or five washes.

In some embodiments, any of the washes provided herein can result in the removal of greater than 50% of any unbound probe from the sample, greater than 55%, greater than 60%, greater than 65%, greater than 70%, greater than 75%, greater than 80%, greater than 85%, greater than 90%, greater than 95%, greater than 99%, greater than 99.9%, greater than 99.99%, greater than 99.999%, or greater than 99.9999999%.

In some embodiments, a trigger oligo is added to the sample, after unbound probe has been washed from the sample. In some embodiments, any of the methods described herein further comprise: washing the sample to remove unpolymerized HCR hairpin monomers; adding a label probe that comprises a complement to the label binding site and a reporter molecule; washing unbound label probe; and detecting a presence or absence of the reporter molecule. In some embodiments, any of the embodiments provided herein further include washing away the unbound trigger oligo.

In some embodiments, any of the washes provided herein can result in the removal of greater than 50% of any unpolymerized HCR hairpin monomers from the sample, greater than 55%, greater than 60%, greater than 65%, greater than 70%, greater than 75%, greater than 80%, greater than 85%, greater than 90%, greater than 95%, greater than 99%, greater than 99.9%, greater than 99.99%, greater than 99.999%, or greater than 99.9999999%.

In some embodiments, amplifying using HCR comprises adding at least two different species of HCR hairpin monomers to the sample. In some embodiments, the two different species comprise a first species comprising a first reporter molecule and a second species comprising a second reporter molecule.

In some embodiments, amplifying using HCR comprises adding three species, or four species, or five species, or six species, or seven species, or eight species, or nine species, or 10 species of HCR hairpin monomers to the sample. In some embodiments, amplifying using HCR comprises adding more than 10 species of HCR hairpin monomers to the sample, for example, 50 species, 100 species, 150 species, 200 species, 250 species, 300 species, 350 species, 400 species, 450 species, 500 species, 550 species, 600 species, 650 species, 700 species, 750 species, 800 species, 850 species, 900 species 950 species, or 1,000 species. In some embodiments, amplifying using HCR comprises adding more than 1,000 species of HCR hairpin monomers to the sample, for example, 2,000 species, 3,000 species, 4,000 species, 5,000 species, 6,000 species, 7,000 species, 8,000 species, 9,000 species, or 10,000 species. In some embodiments, amplifying using HCR comprises adding more than 10,000 species of HCR hairpin monomers to the sample, for example, 20,000 species, 30,000 species, 40,000 species, 50,000 species, 60,000 species, 70,000 species, 80,000 species, 90,000 species, or 100,000 species. In some embodiments, amplifying provides a fluorescent amplification polymer. In some embodiments, amplifying generates a detectable polymer that indicates a presence of a target molecule, wherein the target molecule is bound by the target-binding region. In some embodiments, amplifying using HCR comprises added three species, four species, five species, six species, seven species, eight species, nine species, or 10 species of HCR hairpin monomers to the sample. In some embodiments, amplifying using HCR comprises adding more than 10 species of HCR hairpin monomers, for example, 100 species of HCR hairpin monomers, 1,000 species of HCR hairpin monomers, 10,000 species of HCR hairpin monomers, or 100,000 species of HCR hairpin monomers.

In some embodiments, more than one target is assayed for at a time, wherein each probe comprises a target-binding region selective for each target to be assayed for. In some embodiments, two, three, four, five, six, seven, eight, nine, or 10 targets at a time, wherein each probe comprises a target-binding region selective for each target to be assayed for. In some embodiments, more than 10 targets are assayed for. In some embodiments, more than 100 targets are assayed for at a time, wherein each probe comprises a target-binding region specific for each target to be assayed for. In some embodiments more than 1,000 targets are assayed for, for example, more than 10,000 targets are assayed for, or 100,000 targets are assayed for, wherein each probe comprises a target-binding region selective for each target to be assayed for.

In some embodiments, multiple targets are assayed for at the same time, wherein each of probe comprises a target-binding region selective for a different target molecule and further comprises a structured nucleic acid probe sequestering an HCR initiator for a different HCR amplifier, such that each structured nucleic acid probe can be activated to expose its HCR initiator by a different trigger oligo. In some embodiments, two, three, four, five, six, seven, eight, nine, or 10 HCR amplifiers are used to perform signal amplification for different targets simultaneously. In some embodiments, more than 10 HCR amplifiers are used to perform signal amplification for different targets simultaneously. In some embodiments, more than 100 HCR amplifiers are used to perform signal amplification for different targets simultaneously. In some embodiments, more than 1000 HCR amplifiers are used to perform signal amplification for different targets simultaneously. In some embodiments, more than 10,000 HCR amplifiers are used to perform signal amplification for different targets simultaneously. In some embodiments, more than 100,000 HCR amplifiers are used to perform signal amplification for different targets simultaneously.

In some embodiments, any of the methods described herein is an immunohistochemistry assay. In some embodiments, any of the methods described herein is an immunocytochemistry assay. In some embodiments, any of the methods described herein further comprise parallel multiplexing performed for two or more targets simultaneously, wherein the two or more target molecules are each separately bound by selective probes. In some embodiments, parallel multiplexing is performed for 10 or more targets simultaneously wherein the 10 or more target molecules are each separately bound by selective probes. In some embodiments, parallel multiplexing is performed for 100 or more targets simultaneously wherein the 100 or more target molecules are each separately bound by selective probes. In some embodiments, parallel multiplexing is performed for 1,000 or more targets simultaneously wherein the 1,000 or more target molecules are each separately bound by selective probes. In some embodiments, parallel multiplexing is performed for 10,000 or more targets simultaneously wherein the 10,000 or more target molecules are each separately bound by selective probes. In some embodiments, parallel multiplexing is performed for 100,000 or more targets simultaneously wherein the 100,000 or more target molecules are each separately bound by selective probes.

In some embodiments, the target-binding moiety comprises a primary antibody. In some embodiments, the target-binding moiety comprises a secondary antibody. In some embodiments, in any of the methods described herein, the method comprises use of more than one target-binding moiety, for example, two target-binding moieties, three target-binding moieties, four target-binding moieties, five target-binding moieties, six target-binding moieties, seven target-binding moieties, eight target-binding moieties, nine target-binding moieties, or 10 target-binding moieties. In some embodiments more than 10 target-binding moieties are used in any of the methods described herein, for example, more than 100 target-binding moieties, more than 1,000 target binding moieties, more than 10,000 target binding moieties, or 100,000 target binding moieties.

In some embodiments, the modified HCR hairpin comprises a domain that is complementary (will hybridize) to a domain on the trigger oligo. In some embodiments, the modified HCR hairpin comprises a domain that is only partially complementary (will hybridize) to a domain on the trigger oligo. In some embodiments, the modified HCR hairpin does not comprise a domain that is complementary to a domain on the trigger oligo.

In some embodiments, the structured nucleic acid probe comprises a domain that is complementary (will hybridize) to a domain on the trigger oligo. In some embodiments, the structured nucleic acid probe comprises a domain that is partially complementary (will hybridize) to a domain on the trigger oligo. In some embodiments, the structured nucleic acid probe does not comprise a domain that is complementary to a domain on the trigger oligo.

In some embodiments, any of the methods described herein further comprise binding the trigger oligo to the modified HCR hairpin, wherein binding of the trigger oligo to the modified HCR hairpin results in opening of the modified HCR hairpin.

In some embodiments, the method further comprises binding the trigger oligo to the structured probe, wherein binding of the trigger oligo to the structured probe exposes the previously sequestered HCR initiator.

In any of the methods described herein, any one or more of the following can be detected and/or assayed for: molecules, DNA molecules, RNA molecules, protein molecules, small molecules, synthetic molecules, or complexes of molecules. In some embodiments, the target is more than one target, such as a complex of proteins, or a complex of a protein and a nucleic acid, etc. In some embodiments, inorganic or non-organic materials can also be assayed for. In some embodiments, the target is a nucleic acid molecule. In some embodiments, the target is a protein. In some embodiments, the target consists of at least one of: mRNA, miRNA, lncRNA, rRNA, non-coding RNA, or genomic DNA. In some embodiments, the target is comprised of an amino acid sequence. In some embodiments, the target is comprised of a complex of molecules. In some embodiments, the target is at least one of: DNA, RNA, protein, or small molecule target molecules or complexes in vitro, in situ, ex vivo, or in vivo. In some embodiments, the target is a complex of molecules that is made up of at least one of: DNA, RNA, protein, or small molecule target molecules. In some embodiments the target comprises a molecule or complex in vitro, in situ, or in vivo.

Figure 1C:
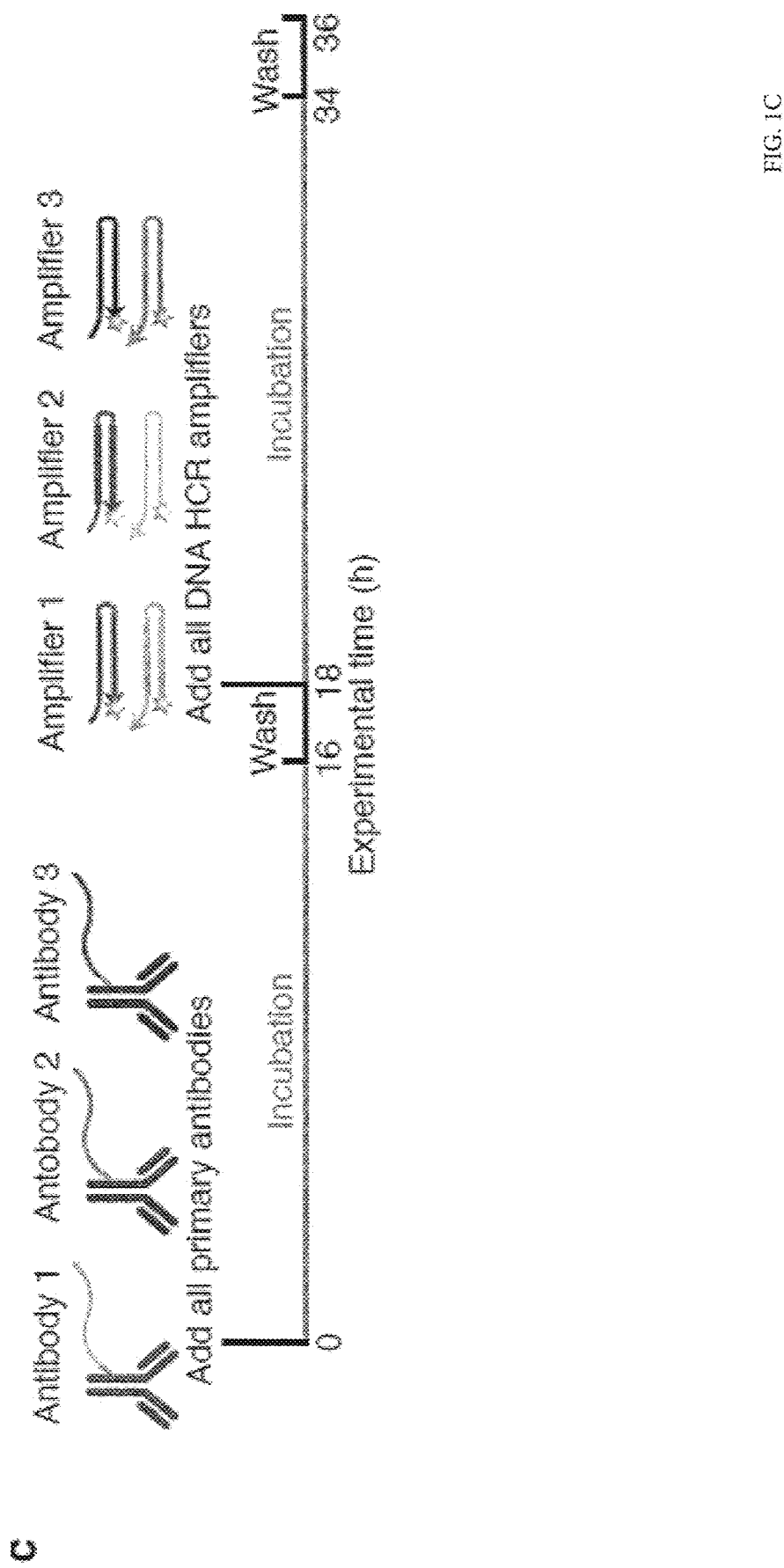

FIG. 1A depicts further embodiments involving HCR. In particular, FIG. 1A shows metastable fluorescent hairpins that self-assemble into fluorescent amplification polymers upon detection of a cognate initiator. Initiator I1 nucleates with hairpin monomer H1 via base-pairing to single-stranded toehold 'a', mediating a branch migration that opens the hairpin monomer to form complex I1·H1 containing single-stranded segment 'c*-b*'. This complex nucleates with hairpin monomer H2 by means of base-pairing to toehold 'c', mediating a branch migration that opens the hairpin monomer to form complex I1·H1·H2 containing single-stranded segment 'b*-a*'. Thus, the initiator sequence is regenerated, providing the basis for a chain reaction of alternating H1 and H2 polymerization steps. Stars denote fluorophores. Arrowhead denotes 3' end of each strand. FIG. 1B shows an immunohistochemistry protocol. Detection stage: antibody probes carrying HCR initiators are hybridized to protein targets and unused probes are washed from the sample. Amplification stage: initiators trigger self-assembly of tethered fluorescent amplification polymers and unused hairpins are washed from the sample. FIG. 1C shows an experimental timeline. The same two-stage protocol is used independent of the number of target molecule species. For multiplexed experiments, antibody probes for different target species carry orthogonal initiators that trigger orthogonal HCR amplification cascades labeled by spectrally distinct fluorophores.

FIGS. 2A-2B depict further embodiments involving HCR-IHC schemes that use oligo-labeled primary antibodies.

Scheme A of FIG. 2A depicts an embodiment using a primary antibody labeled with unstructured HCR initiator.

Stage 1 of Scheme A: Target protein detection using primary antibody labeled with unstructured HCR initiator. Antibody probes are hybridized within the fixed sample and unused probes are washed away.

Stage 2 of Scheme A: Signal amplification using HCR. HCR hairpins are hybridized within the fixed sample and unused hairpins are washed away. This is a simple 2-stage scheme.

Performance implications of Scheme A: With Scheme A, unstructured HCR initiators carried by the primary antibody can inhibit sample penetration and/or increase non-specific binding of the antibody probe within the sample, generating amplified background during Stage 2.

Scheme B of FIG. 2B depicts an embodiment using primary antibody labeled with HCR hairpin. To reduce the potential for non-specific binding of the antibody probe, Scheme B instead labels the primary antibody with one or more HCR hairpins. Because each HCR hairpin contains a duplex stem, the potential for off-target base pairing of the oligo-labeled antibody probe is reduced compared to Scheme A.

Stage 1 of Scheme B: Target protein detection using primary antibody labeled with HCR hairpin. Antibody probes are hybridized within the fixed sample and unused probes are washed away.

Stage 2 of Scheme B: Probe activation using unstructured HCR initiator. Initiators are hybridized within the fixed sample and unused initiators are washed away. The HCR initiators open the HCR hairpins carried by the antibody probe, activating the hairpins by exposing an HCR initiator for subsequent triggering of HCR signal amplification in Stage 3.

Stage 3 of Scheme B: Signal amplification using HCR. HCR hairpins are hybridized within the fixed sample and unused hairpins are washed away.

Performance implications of Scheme B: Compared to Scheme A, where one or more HCR initiators label the antibody probe, the individual HCR initiators used in Scheme B are less susceptible to non-specific binding within the sample, and there is no potential for polyvalent off-target binding (which does exist with Scheme A if antibody probes carry more than one HCR initiator). With Scheme B, if the HCR initiator binds non-specifically in the sample during Stage 2, it will lead to amplified background during Stage 3.

Scheme C of FIG. 2C depicts an embodiment using a primary antibody labeled with a modified HCR hairpin. This embodiment reduces background by changing the toehold sequence for the input domain of the modified hairpins labeling the antibody probe, as well as the corresponding sequence in an unstructured trigger oligo that will be used to activate the modified hairpins carried by the antibody probe. For example, the antibody probe can be labeled with modified versions of the H1 hairpin monomer containing input domain ('e-b') instead of the input domain ('a-b') carried by a standard H1 hairpin monomer. This modified version of H1 can be activated by a trigger oligo ('b*-e*') in Stage 2 that is not itself an HCR initiator. As a result, if the trigger oligo binds non-specifically in the sample, it will not generate amplified background in Stage 3.

Stage 1 of Scheme C: Target protein detection using primary antibody labeled with modified HCR hairpin. Antibody probes are hybridized within the fixed sample and unused probes are washed away.

Stage 2 of Scheme C: Probe activation using unstructured trigger oligo. The trigger oligos open the modified hairpins carried by the antibody probe, activating the modified hairpins by exposing an HCR initiator for subsequent triggering of HCR signal amplification in Stage 3.

Stage 3 of Scheme C: Signal amplification using HCR. HCR hairpins are hybridized within the fixed sample and unused hairpins are washed away.

Performance Implications of Scheme C: Compared to Scheme B, Scheme C has the additional benefit that non-specific binding of the unstructured trigger oligo in Stage 2 does not lead to amplified background in Stage 3. Because the unstructured trigger oligo is not an HCR initiator, only the activated hairpins carried by the antibody probes are capable of triggering growth of HCR amplification polymers in Stage 3.

Scheme D of FIG. 2D depicts an embodiment using a primary antibody labeled with a hairpin probe that sequesters an HCR initiator. In this embodiment, instead of using a modified HCR hairpin where only the toehold of the input domain is changed relative to a normal HCR hairpin, the hairpin probe that labels the antibody can have domain dimensions and/or domain sequences that differ from a normal HCR hairpin. For example, the toehold length of the input domain could be extended relative to that of a normal HCR hairpin to promote high-yield activation of the hairpin probes carried by the antibody probes. Functionally, the hairpin probe labeling the antibody probe has the property that it predominantly initiates HCR if and only if it has been activated by the trigger oligo in Stage 2. Stage 1 of Scheme D: Target protein detection using primary antibody labeled with hairpin probe that sequesters an HCR initiator. Antibody probes are hybridized within the fixed sample and unused probes are washed away.

Stage 2 of Scheme D: Hairpin probe activation using unstructured trigger oligo. The trigger oligos open the hairpin probes carried by the antibody probe, activating the hairpin probes by exposing an HCR initiator for subsequent triggering of HCR signal amplification in Stage 3.

Stage 3 of Scheme D: Signal amplification using HCR. HCR hairpins are hybridized within the fixed sample and unused hairpins are washed away.

Performance Implications of Scheme D: This scheme has the potential to increase the yield of hairpin activation on antibody probes.

In some embodiments, instead of labeling the primary antibody with an oligo, another option is to use unlabeled primary antibodies, and instead to use oligo-labeled secondary antibodies to initiate the growth of tethered fluorescent HCR amplification polymers. The following four Schemes (E, F, G, H) of FIGS. 3A-3D parallel the four previous schemes (A, B, C, D) of FIGS. 2A-2D; in each case, there is one extra stage corresponding to the use of a secondary antibody to detect the primary antibody, and the oligo label has been shifted from the primary antibody to the secondary antibody.

Figure 3A:
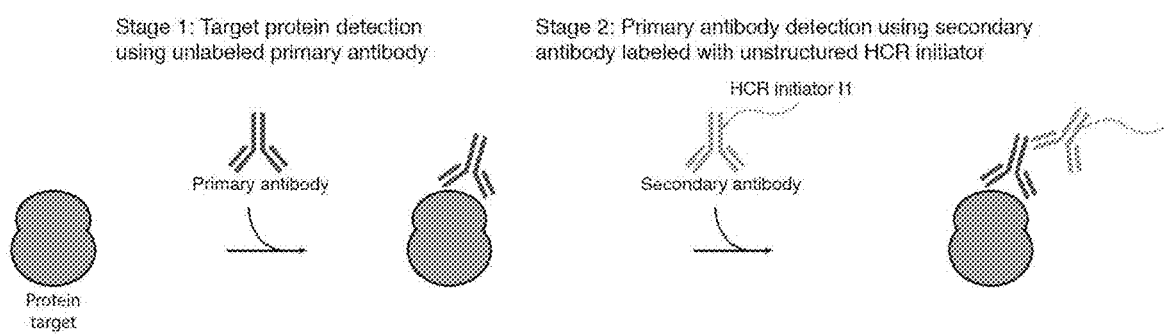
FIGS. 3A-3D depicts HCR-IHC using oligo-labeled secondary antibodies.
Figure 3A:
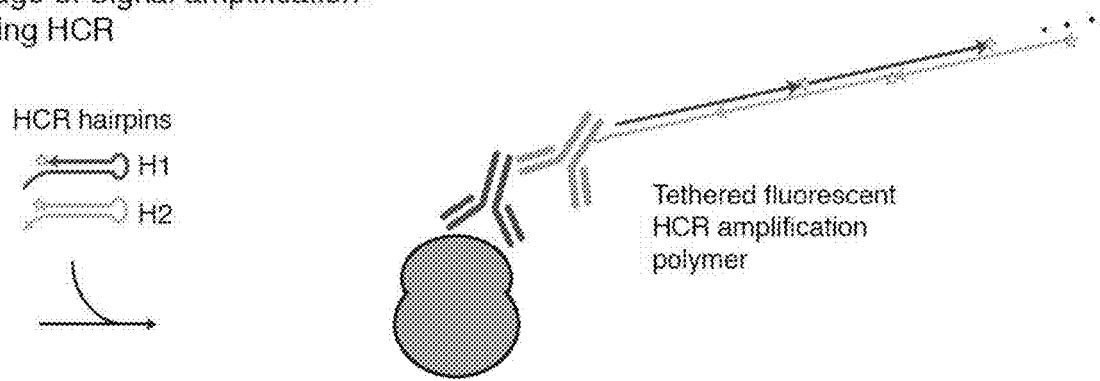

Scheme E of FIG. 3A depicts an embodiment using a secondary antibody labeled with unstructured HCR initiator. Stage 1 of Scheme E: Target protein detection using unlabeled primary antibody. Stage 2 of Scheme E: Primary antibody detection using secondary antibodies labeled with unstructured HCR initiators. Stage 3 of Scheme E: Signal amplification using HCR.

Figure 3B:
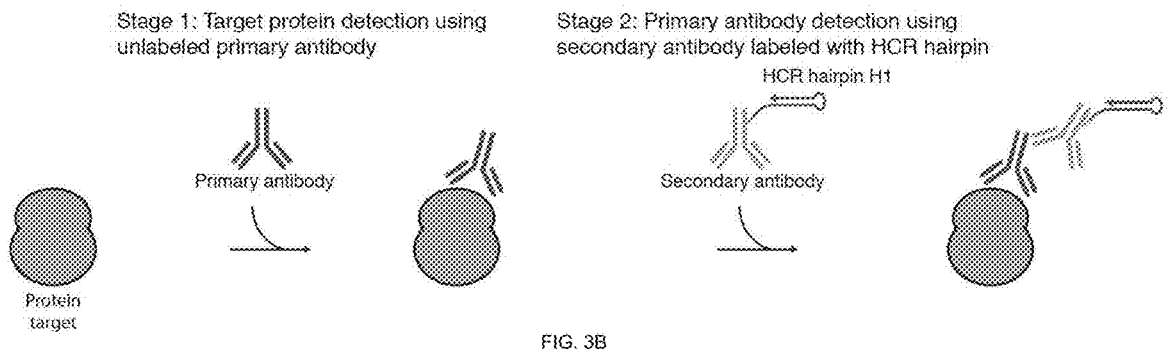
Figure 3B:
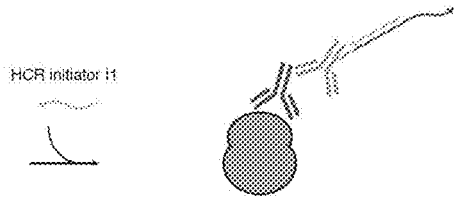
Figure 3B:

Scheme F of FIG. 3B depicts an embodiment of a secondary antibody labeled with HCR hairpin. Stage 1 of Scheme F: Target protein detection using unlabeled primary antibody. Stage 2 of Scheme F: Primary antibody detection using secondary antibodies labeled with HCR hairpins. Stage 3 of Scheme F: Probe activation using an unstructured HCR initiator. Stage 4 of Scheme F: Signal amplification using HCR.

Figure 3C:
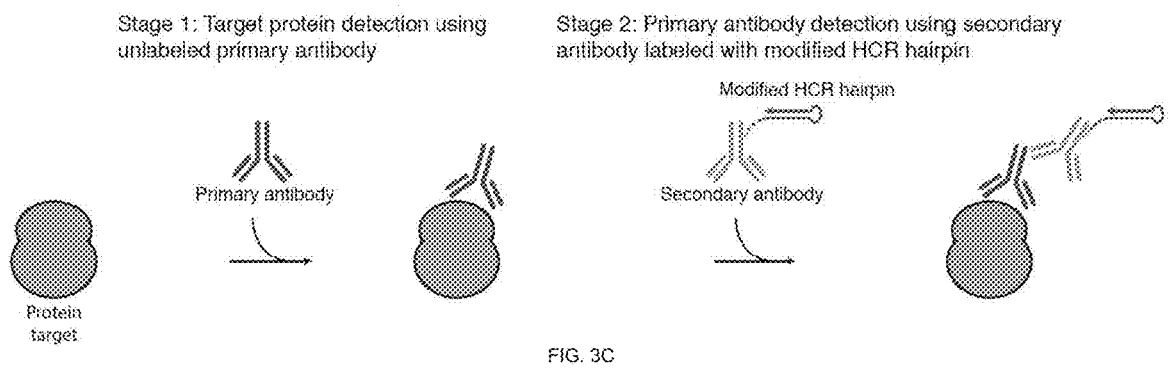
Figure 3C:
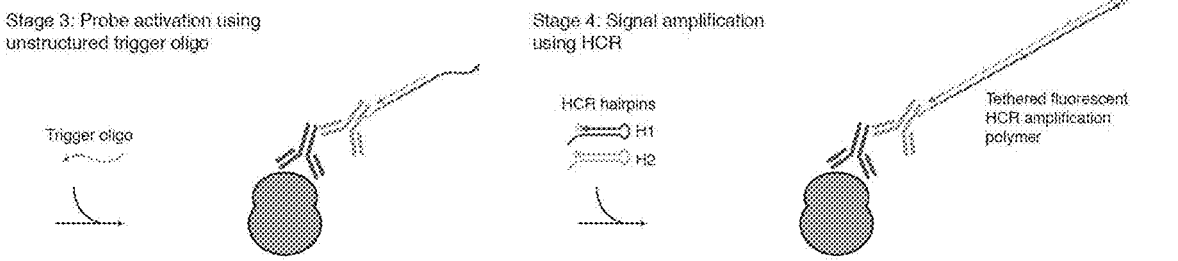

Scheme G of FIG. 3C depicts an embodiment using a secondary antibody labeled with modified HCR hairpin. Stage 1 of Scheme G: Target protein detection using unlabeled primary antibody. Stage 2 of Scheme G: Primary antibody detection using secondary antibodies labeled with modified HCR hairpins. Stage 3 of Scheme G: Probe activation using an unstructured trigger oligo. Stage 4 of Scheme G: Signal amplification using HCR.

Figure 3D:
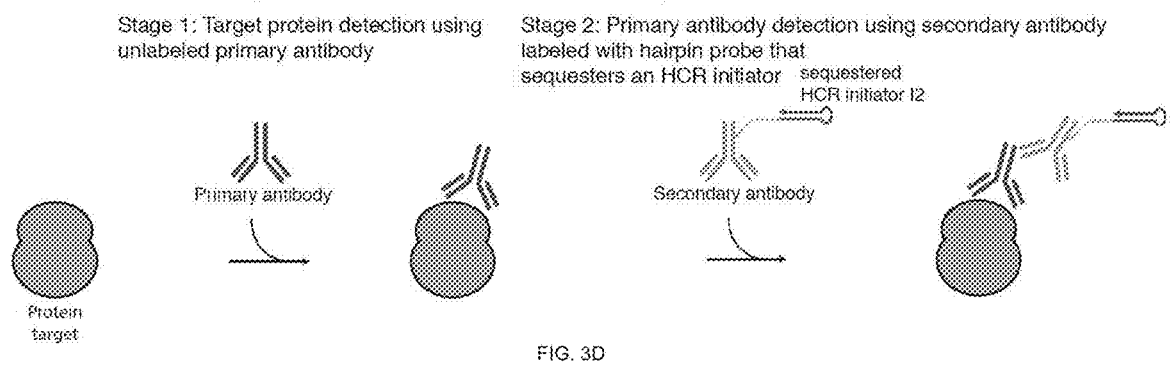
Figure 3D:
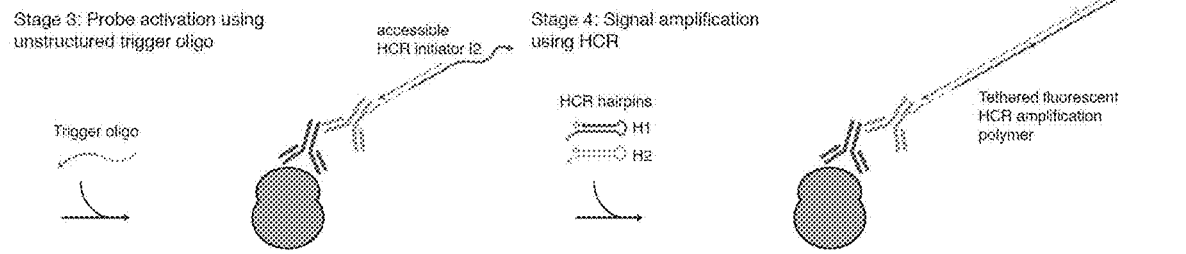

Scheme H of FIG. 3D depicts an embodiment using a secondary antibody labeled with a hairpin probe that sequesters an HCR initiator. Stage 1 of Scheme H: Target protein detection using unlabeled primary antibody. Stage 2 of Scheme H: Primary antibody detection using secondary antibodies labeled with hairpin probes that sequester an HCR initiator. Stage 3 of Scheme H: Hairpin probe activation using an unstructured trigger oligo. Stage 4 of Scheme H: Signal amplification using HCR.

In some embodiments, a disadvantage of using a secondary antibody (Schemes E, F, G, H of FIGS. 3A-3D) is the need for an extra stage in the protocol (relative to Schemes A, B, C, D of FIGS. 2A-2D).

Performance Implications: In some embodiments, the advantage of using oligo-labeled secondary antibodies is that a library of orthogonal secondary antibodies can be validated and reused for different primary antibodies. For example, consider a library of five orthogonal secondary antibodies. These could each be reused for 1000 primary antibodies that detect different target proteins.

In some embodiments, an advantage of using oligo-labeled primary antibodies is the ability to perform highly multiplexed experiments in which multiple target types are detected simultaneously using different primary antibodies that each bind selectively to a single target type; for example simultaneous detection of 10 target types, or 100 target types, or 1000 target types, or 10,000 target types, or 100,000 target types.

Figure 9:
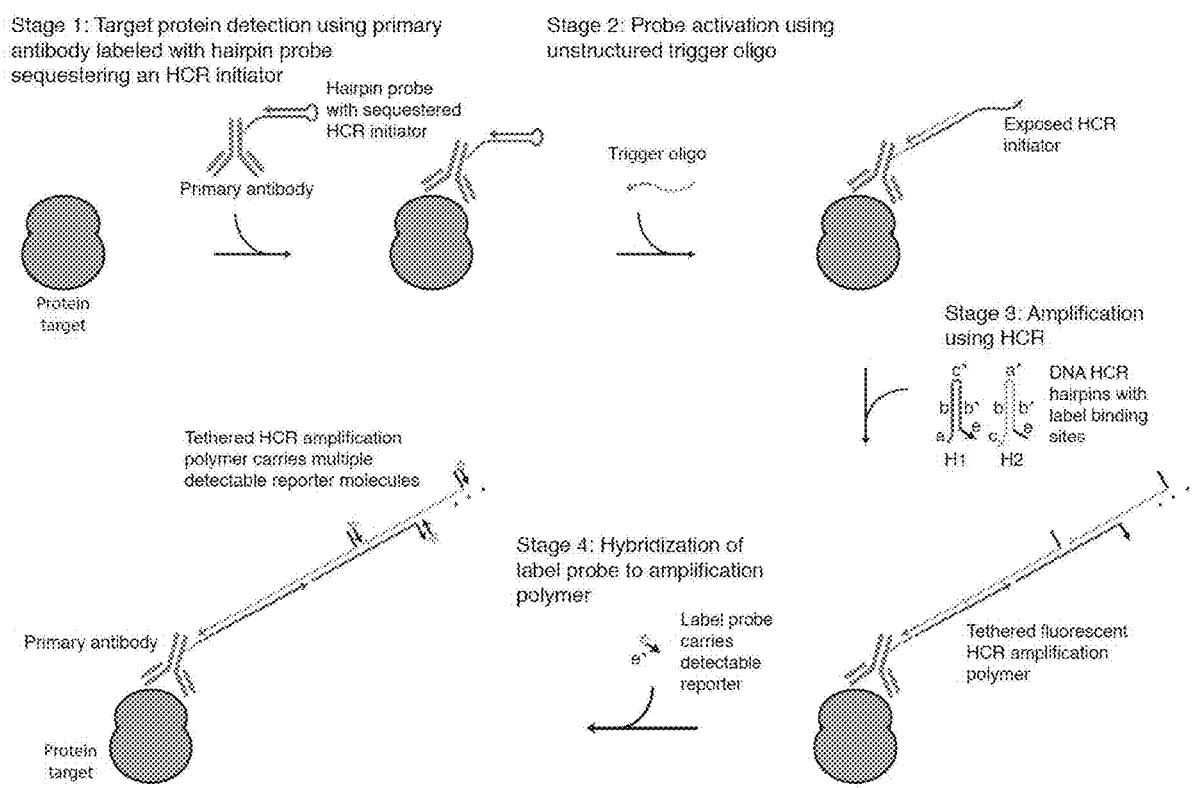
FIG. 9. HCR-IHC using label probes.
Figures 1A, 1B, 1C:
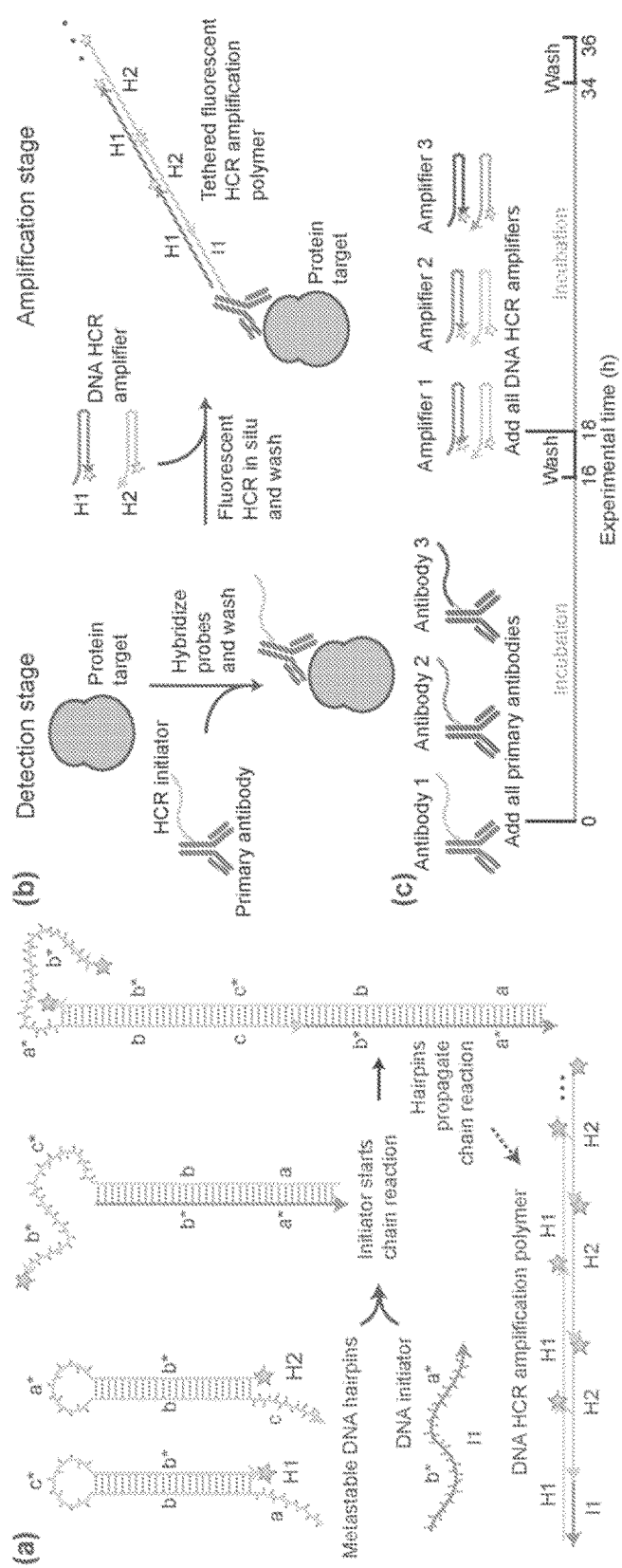
Figure 2A:
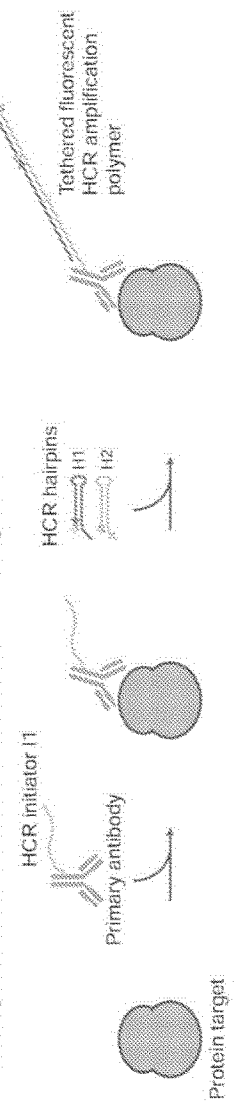
Figure 2B:
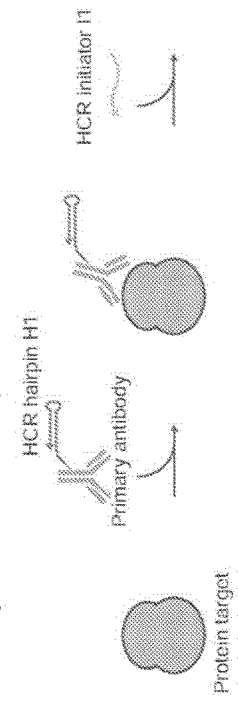
Figure 2C:
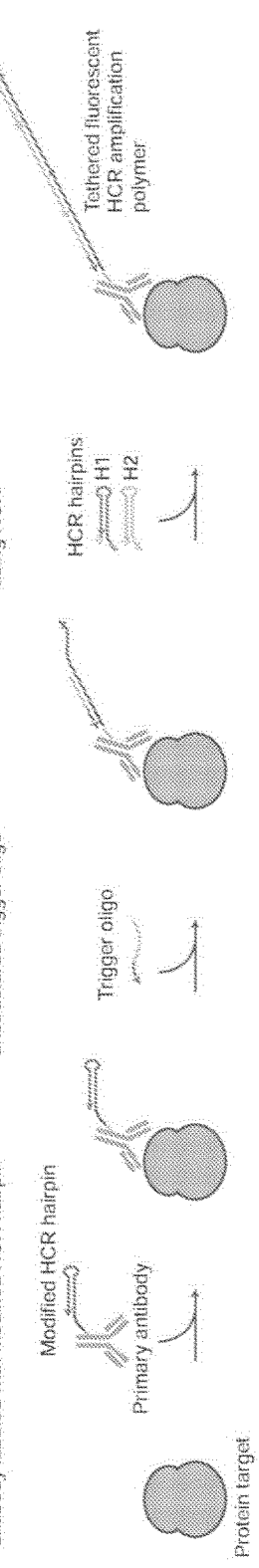
Figure 3A:
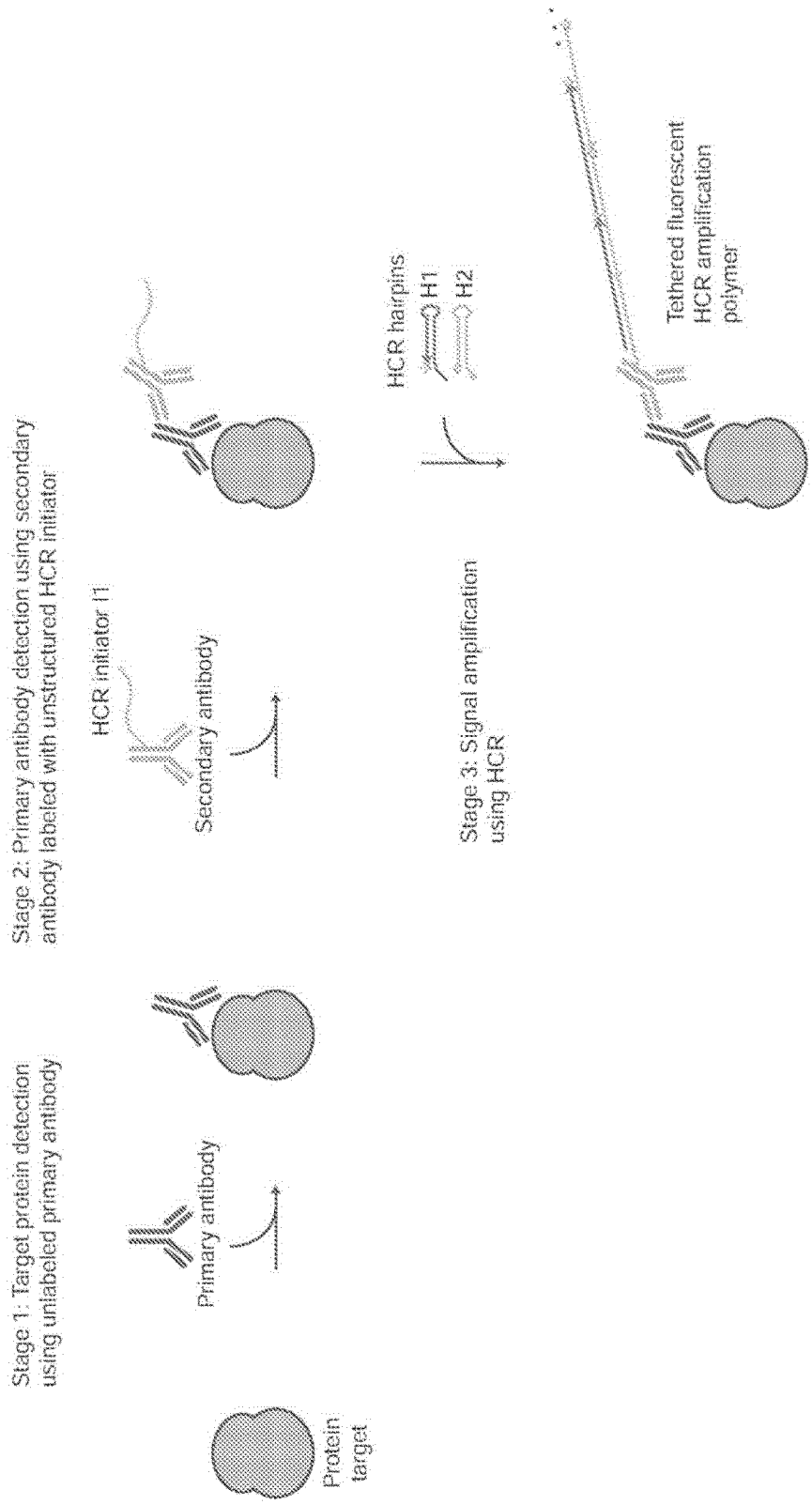
Figure 3B:
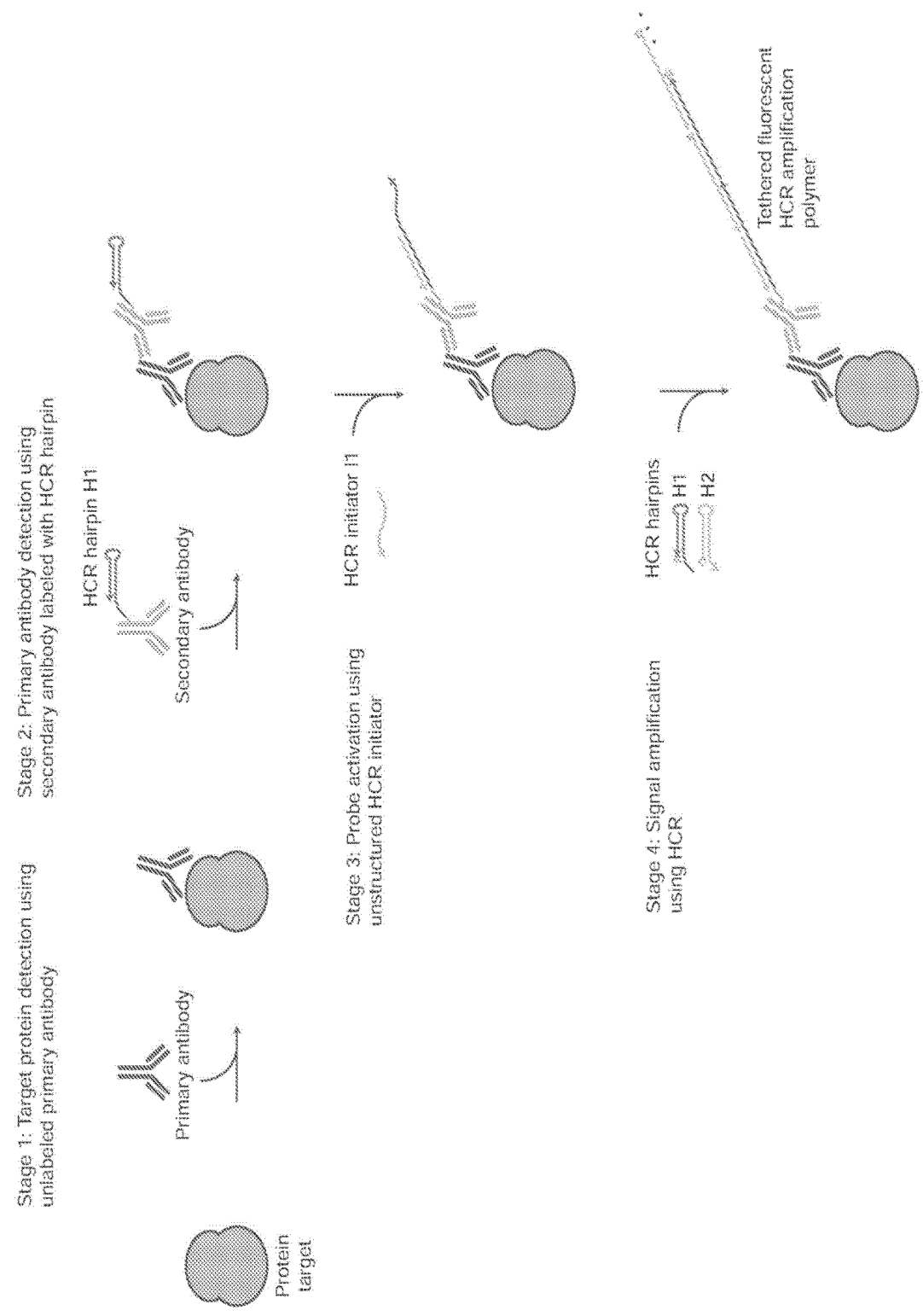
Figure 3C:
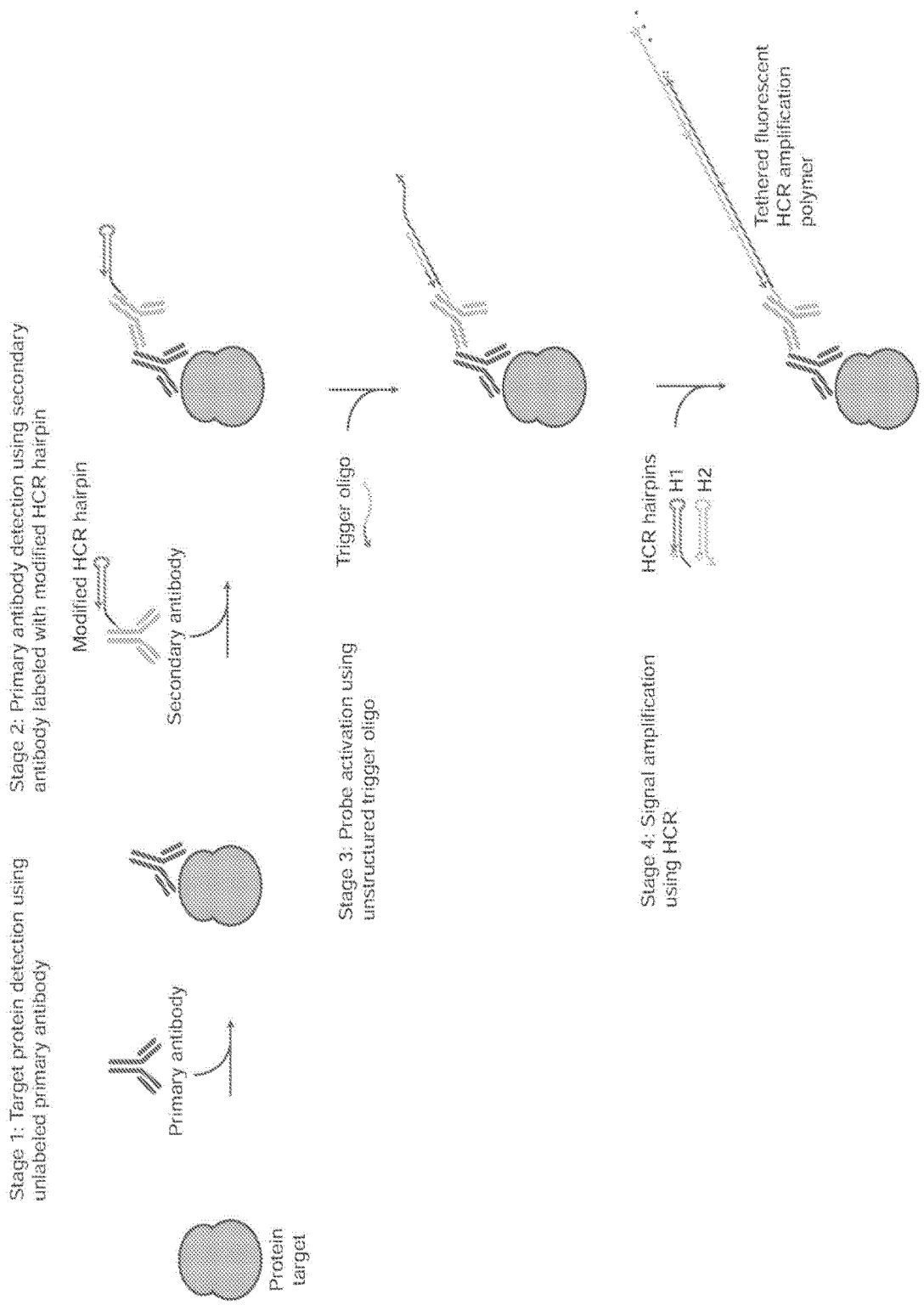
Figure 3D:
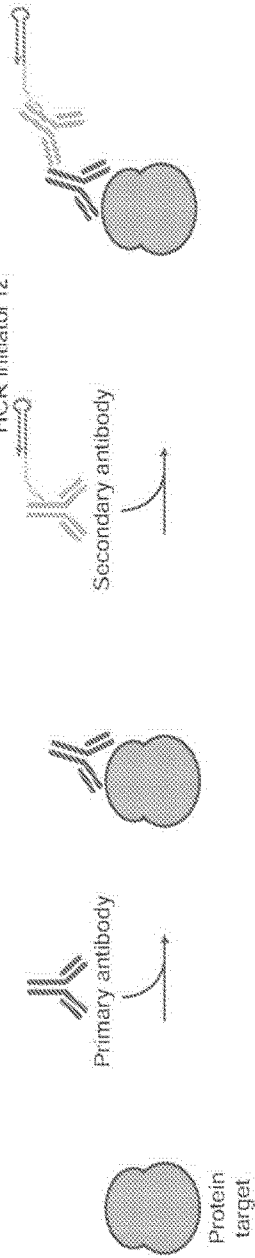
Figure 3D:
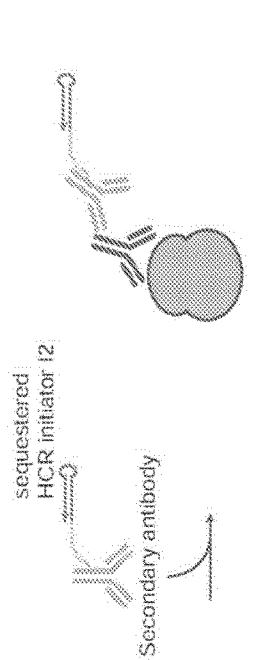
Figure 3D:
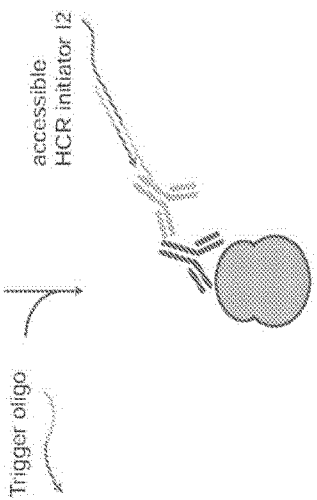
Figure 3D:
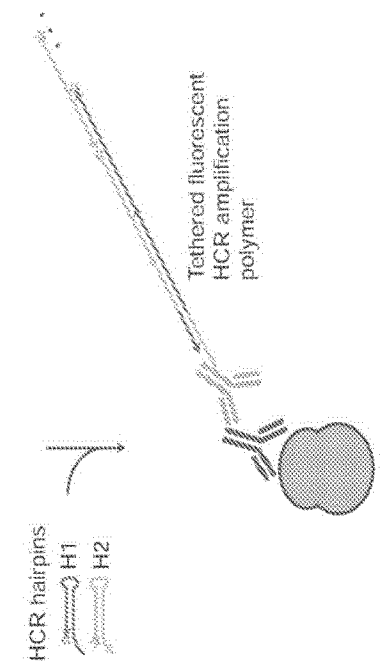
Figures 4A, 4B, 4C:
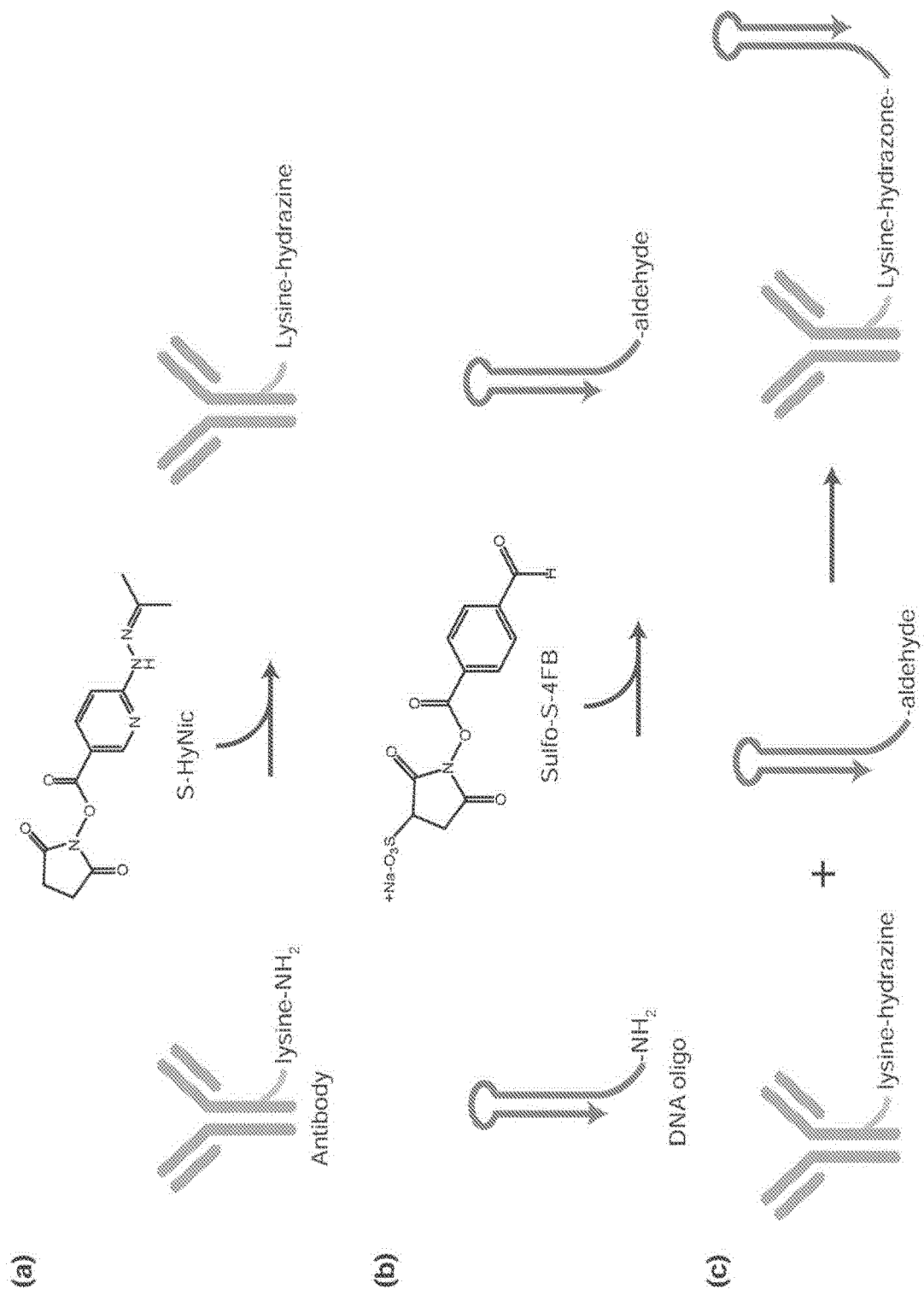
Figure 5:
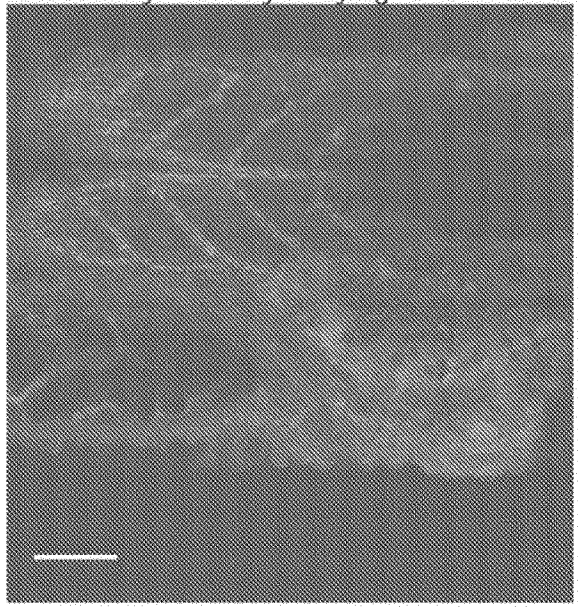
Figure 5:
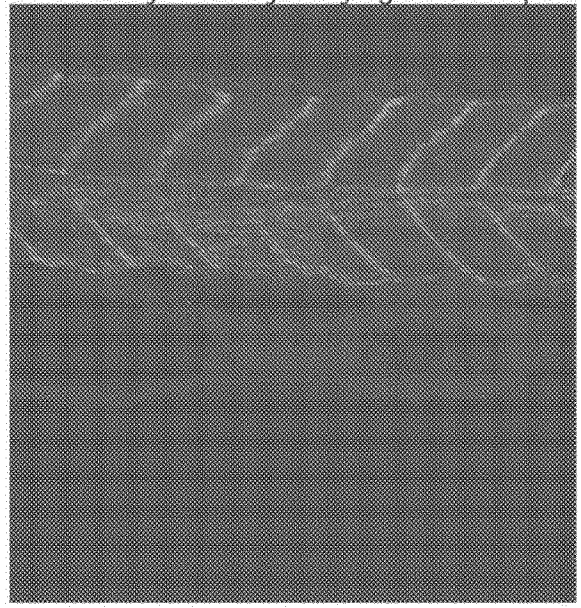
Figures 6A, 6B:
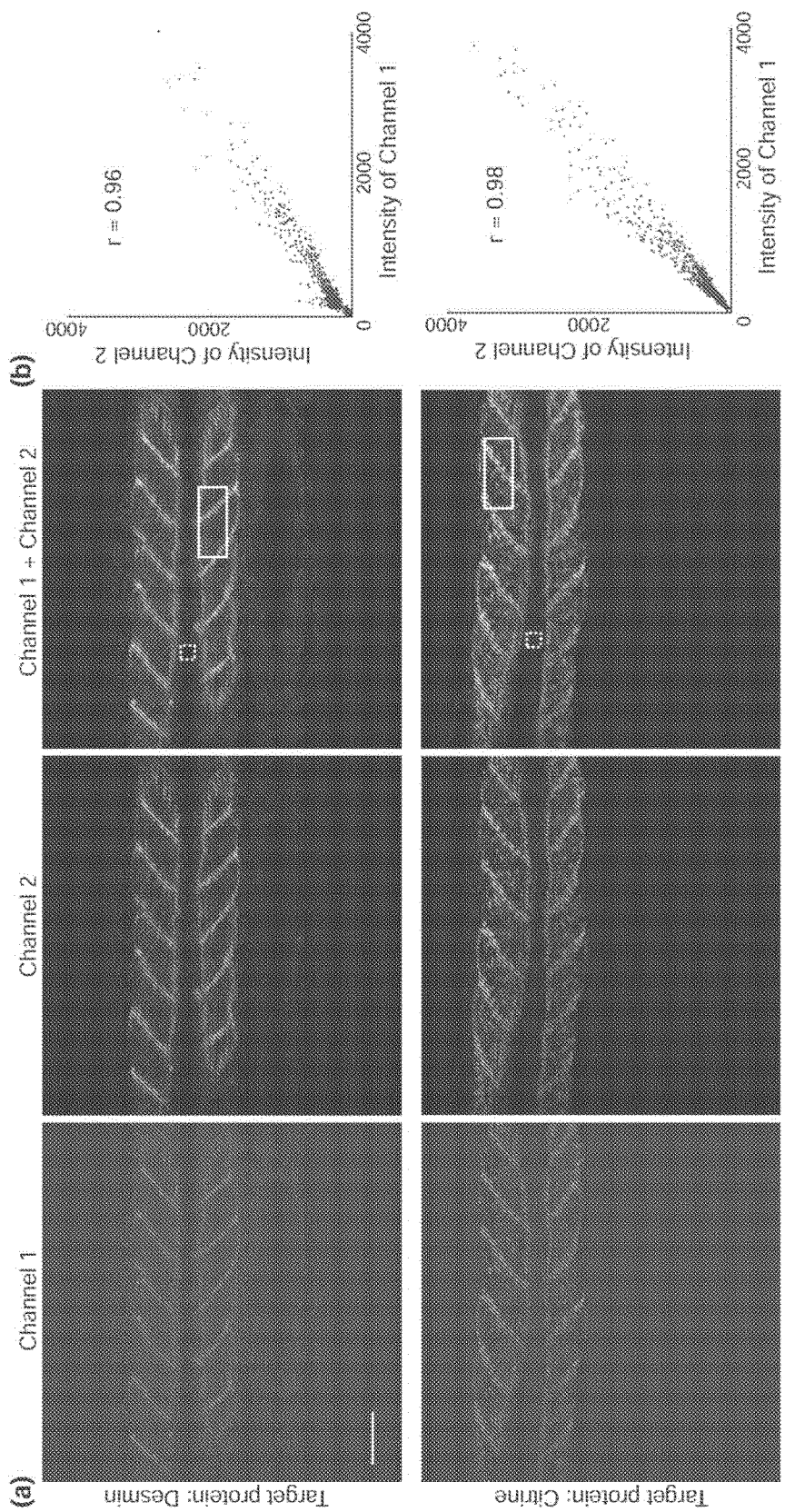
Figure 7:
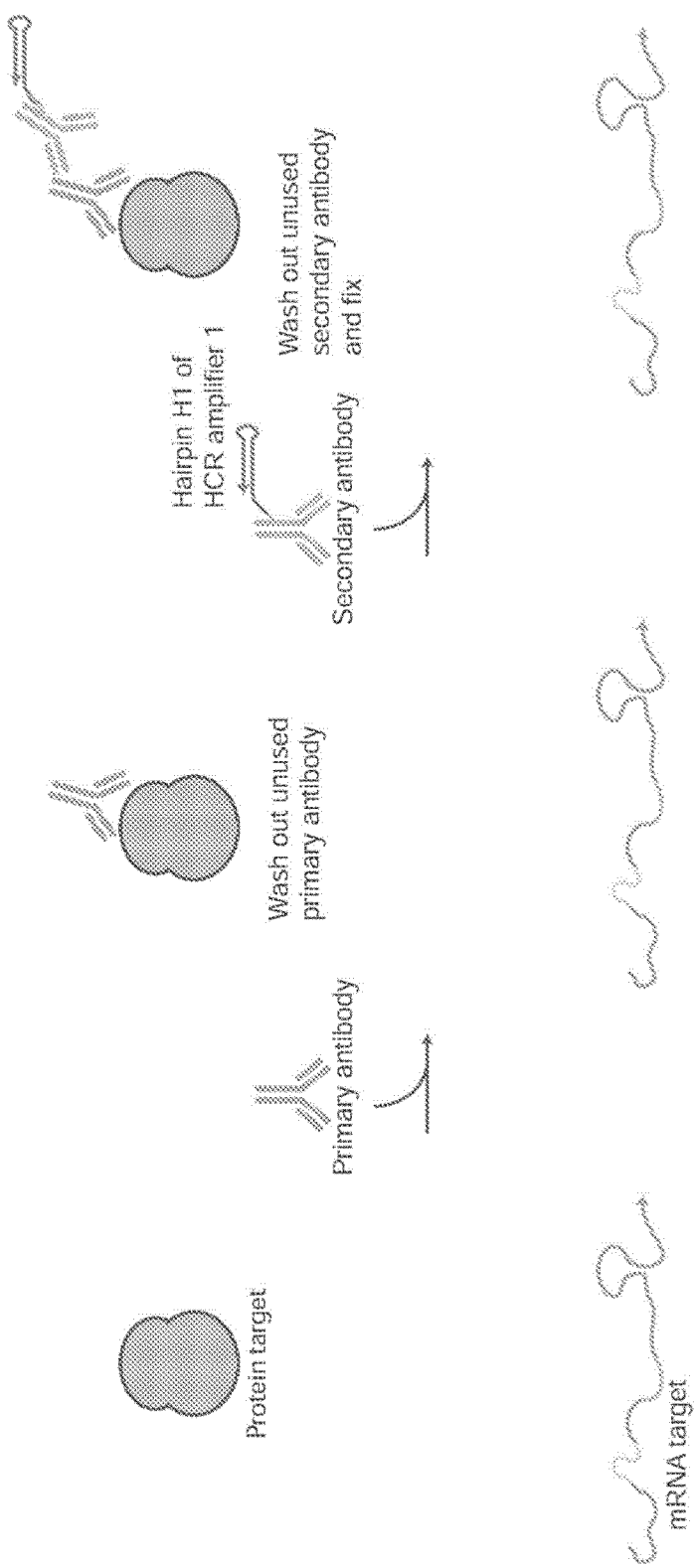
Figure 7:
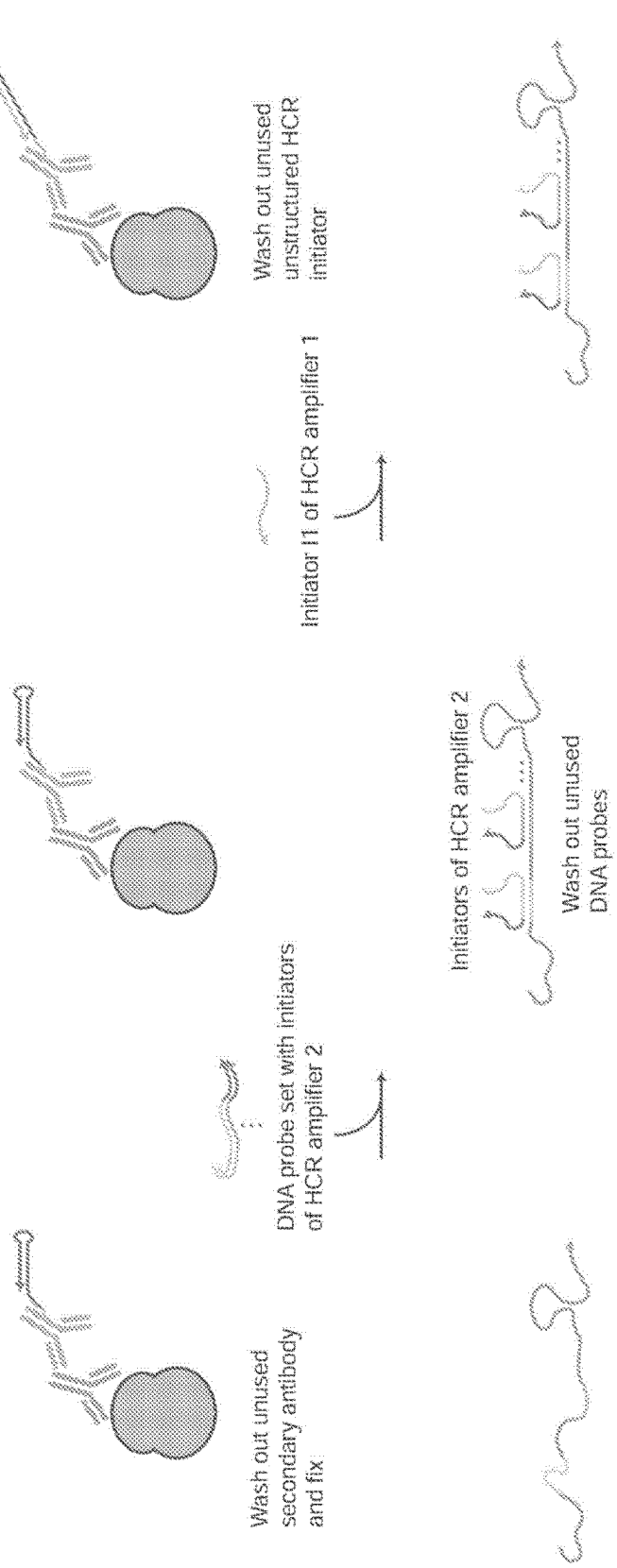
Figure 7:
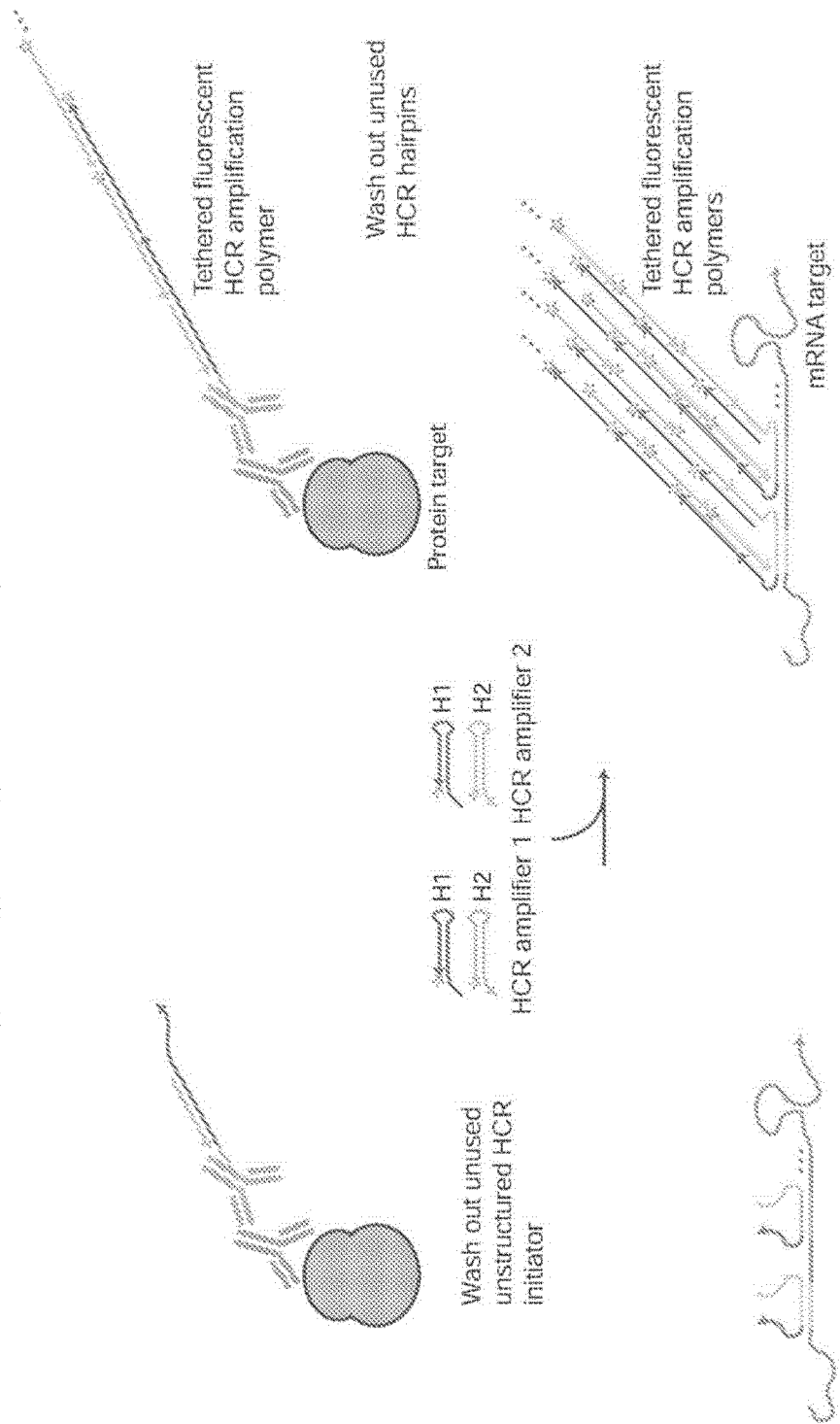

In some embodiments, a method is provided that is depicted in FIG. 9. The method comprises a four-stage scheme: a) Stage 1: target detected using primary antibody probe carrying nucleic acid hairpin probe sequestering HCR initiator; unbound probe washed from sample. Stage 2: Unstructured trigger oligo activates hairpin probe, exposing HCR initiator; unbound trigger oligos washed from sample. Stage 3: signal amplification via polymerization of H1 and H2 hairpins, each carrying label binding site; unbound H1 and H2 hairpins washed from sample. Stage 4: label probes comprising a complement to the label binding site and additionally comprising a detectable reporter are hybridized to the amplification polymers; unbound label probes are washed from the sample.

EXAMPLES

Examples of HCR-IHC

Example 1

Figure 4A:
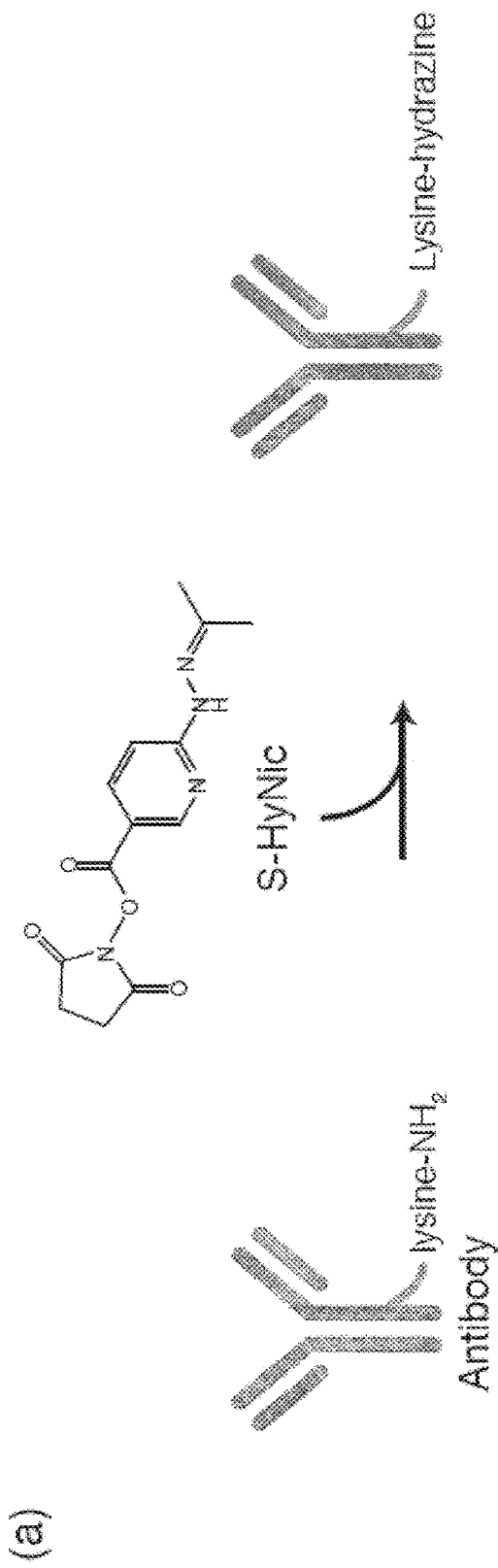
FIGS. 4A-4C. Antibody-oligo conjugation scheme.
Figure 4B:
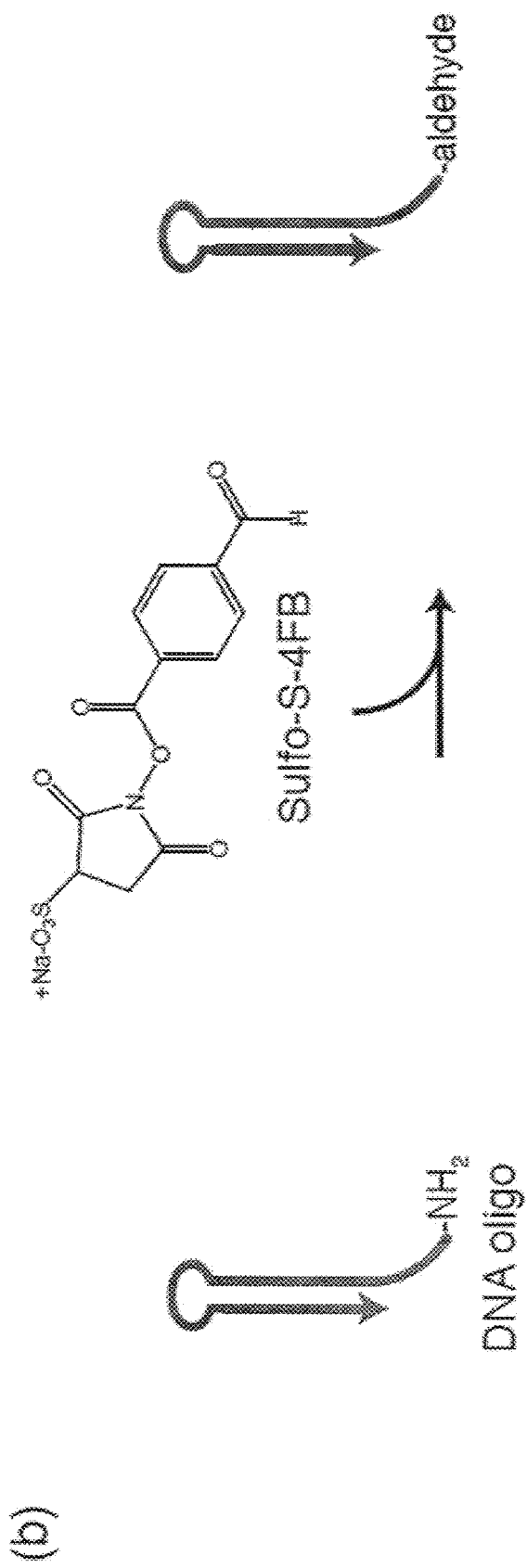
Figure 4C:
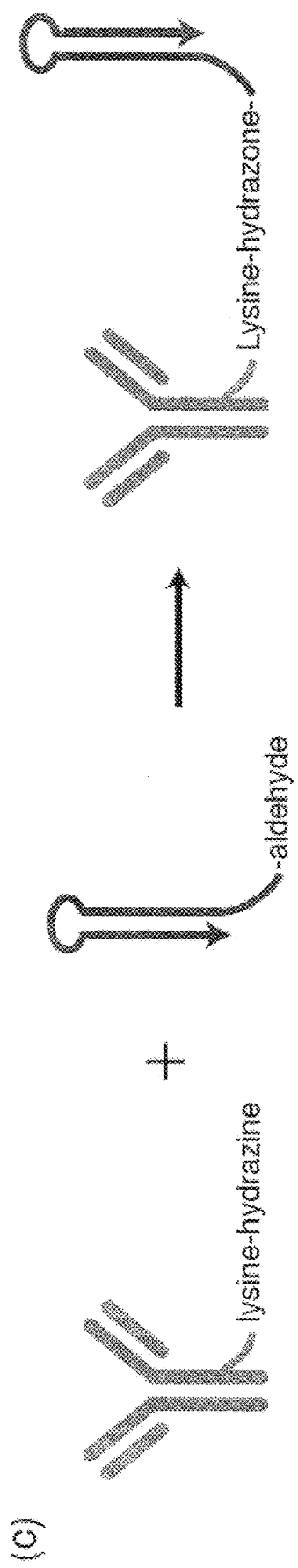

An example of an antibody-oligo conjugation scheme is shown in FIGS. 4A-4C. As shown in FIG. 4A, the heterobifunctional linker S-HyNiC is reacted with the amine group of lysine residues within the antibody, functionalizing the antibody with a hydrazide group. In FIG. 4B the oligo is synthesized with an amine group and reacted with a heterobifunctional linker S-4FB, functionalizing the oligo with an aldehyde group. In FIG. 4C the two functionalized components are incubated together in the presence of an aniline catalyst that promotes the formation of a hydrazone bond, covalently linking the antibody and the oligo.

Example 2

Figure 5:
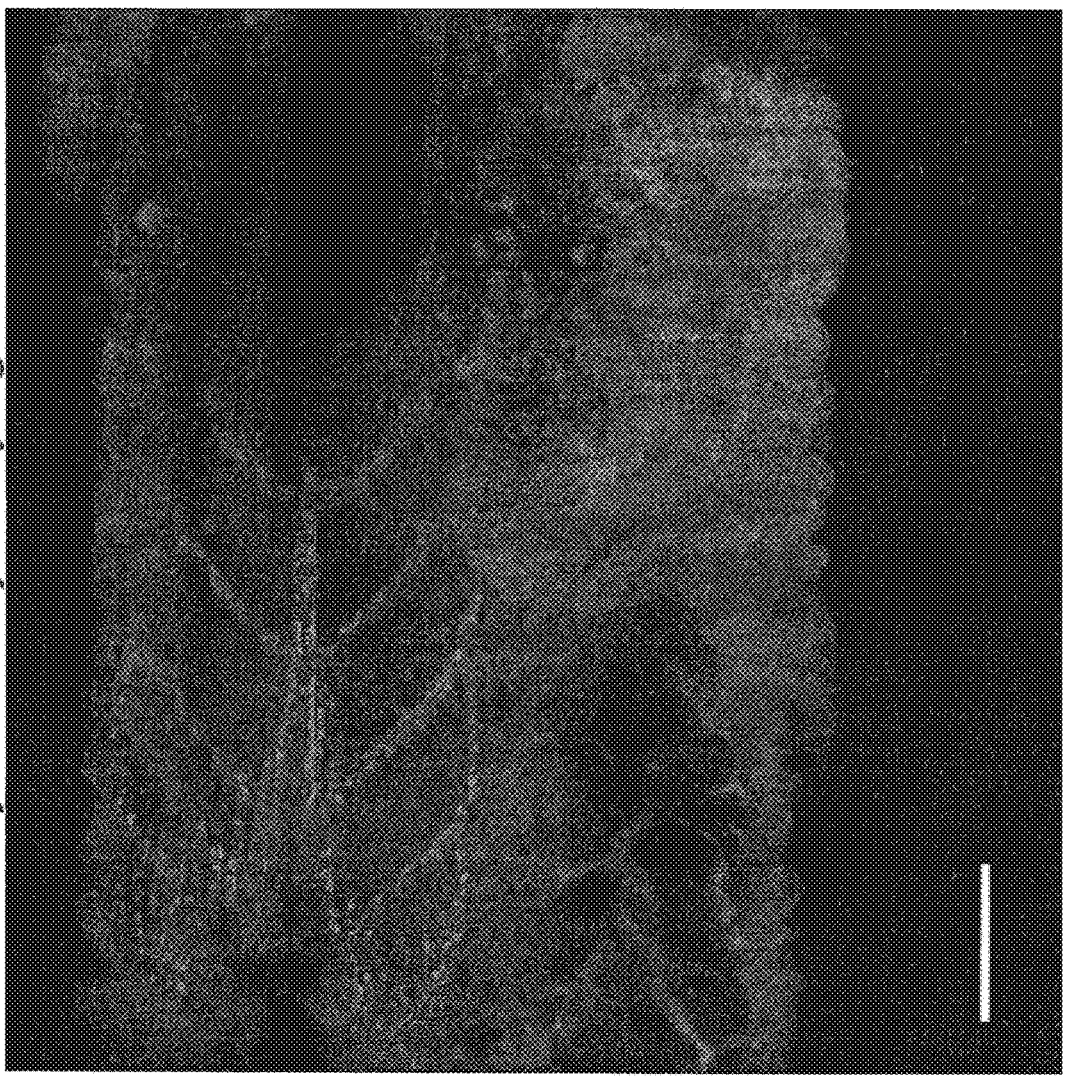
FIG. 5. Performance results of Scheme E (secondary antibody carrying HCR initiator) vs Scheme F (secondary antibody carrying HCR hairpin) in whole-mount zebrafish embryos.

A HCR-IHC result is illustrated in FIG. 5. Reduced background was observed using Scheme F (secondary antibodies carrying HCR hairpins) relative to Scheme E (secondary antibodies carrying unstructured HCR initiators), indicating that antibodies labeled with HCR hairpins are less prone to non-specific binding than antibodies labeled with unstructured HCR initiators. As shown in FIG. 5, sample penetration was improved and background was reduced using the hairpin-labeled antibodies (Scheme F). Embryos fixed 27 hours post-fertilization (hpf). Scale bar: 50 µm.

Example 3

Figure 6A:
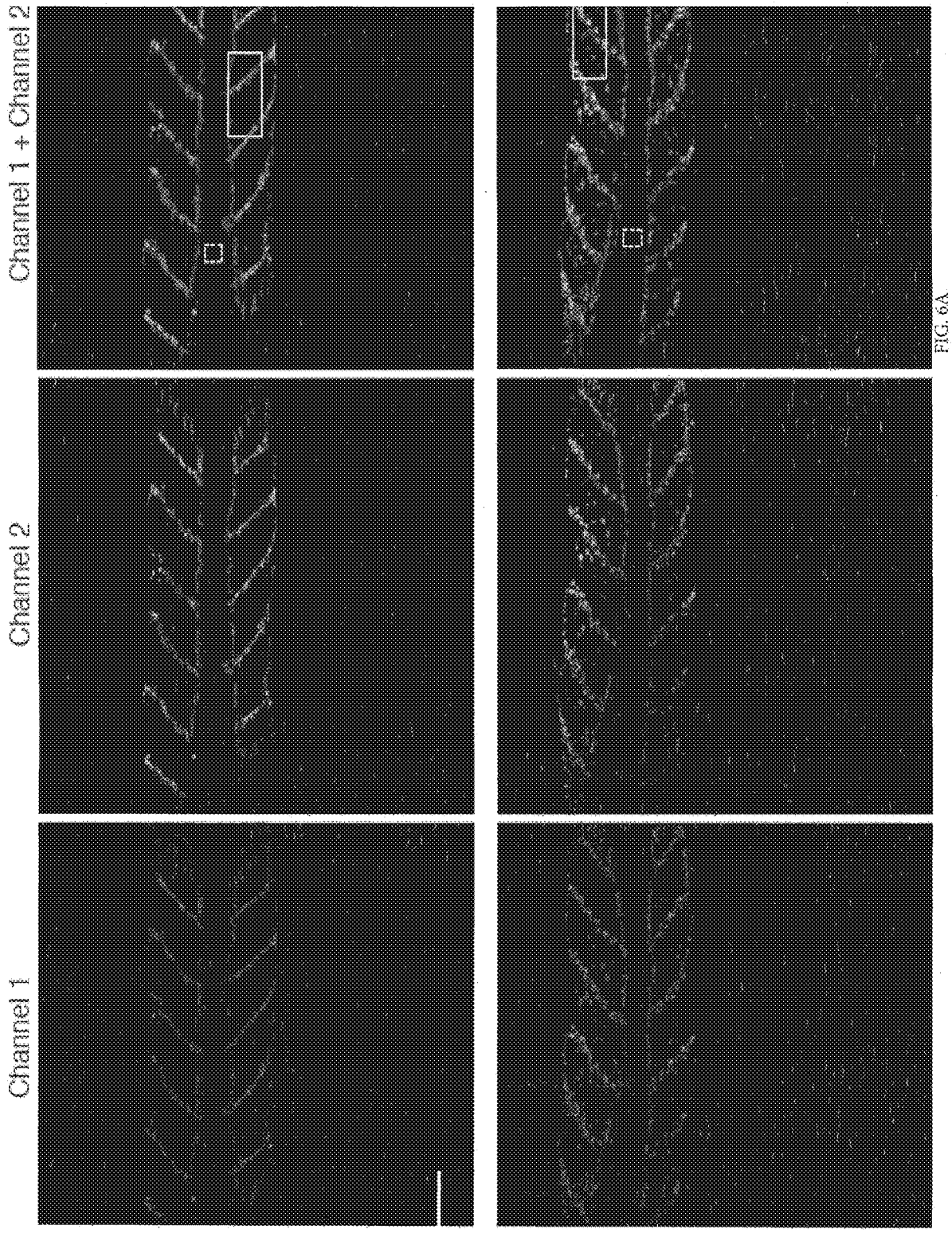
FIGS. 6A-6B. Relative quantitation of target protein expression via HCR-IHC.
Figure 6B:
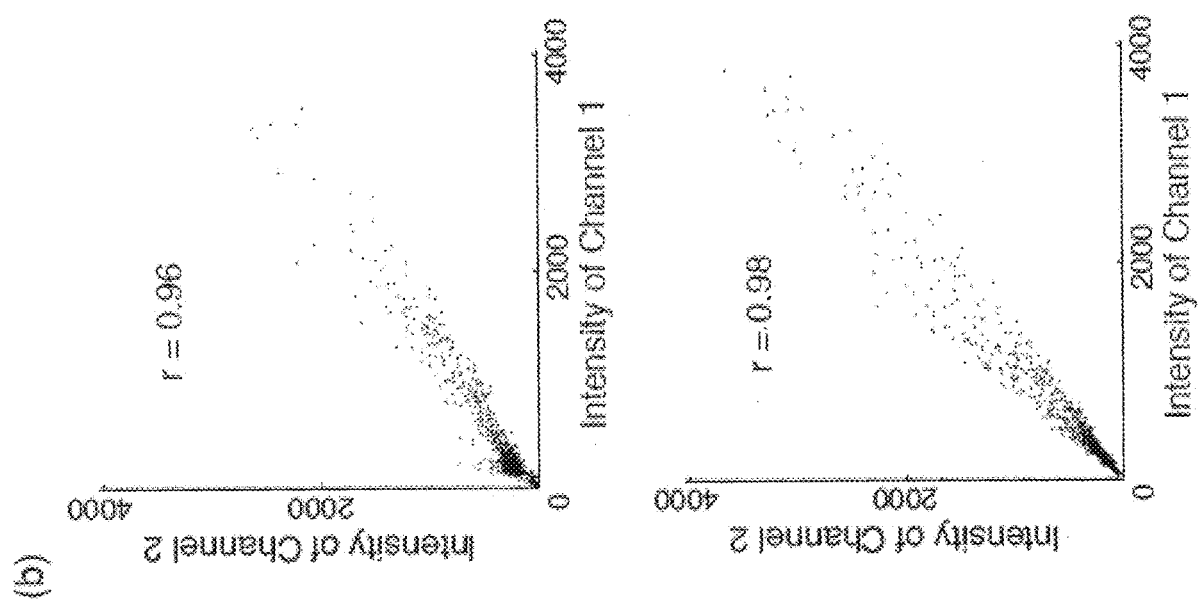

The quantitative nature of HCR is illustrated in FIGS. 6A-6B. Using Scheme F of FIG. 3B, target proteins were detected using primary antibodies (Stage 1). Then, two batches of secondary antibodies carrying orthogonal HCR hairpins were used to detect the primary antibodies (Stage 2). These probes were then each activated using their orthogonal HCR initiators (Stage 3). HCR amplification was then performed using the two orthogonal HCR systems carrying spectrally distinct fluorophores (Stage 4), leading to redundant imaging of protein expression. If HCR signal scales linearly with primary antibody abundance, a 2-channel scatter plot of voxel intensities will reveal a linear distribution. If primary antibody binding scales linearly with target protein abundance, HCR-ISH will enable relative quantitation of protein abundance within the fixed sample.

FIG. 6A shows redundant 2-channel mapping of protein expression using two batches of secondary antibody and two orthogonal HCR amplifiers carrying spectrally distinct fluorophores. Row 1: Zebrafish line: wild type. Target protein: Desmin. Primary antibody: rabbit anti-Desmin. Secondary antibody: donkey anti-rabbit. Row 2: Zebrafish line: ct-122a. Target protein: Citrine. Primary antibody: chicken anti-GFP (which binds selectively to Citrine protein). Secondary antibody: goat anti-chicken. FIG. 6B Highly correlated subcellular voxel intensities within the solid boundary (Pearson correlation coefficient: r=0.96 for Desmin, r=0.98 for Citrine). To avoid inflating the correlation coefficient, voxels were excluded that fell below background thresholds in both channels (excluded voxels lie in the black rectangles at the lower left corner of the correlation plots). For each channel, the background threshold was defined as the mean plus two standard deviations for the voxels in the small white dashed square. Embryos fixed 27 hours post-fertilization. Scale bar: 50 μm.

Example of Simultaneously Mapping Protein and mRNA Expression Via HCR-IHC/HCR-ISH Example 4

Figure 7:
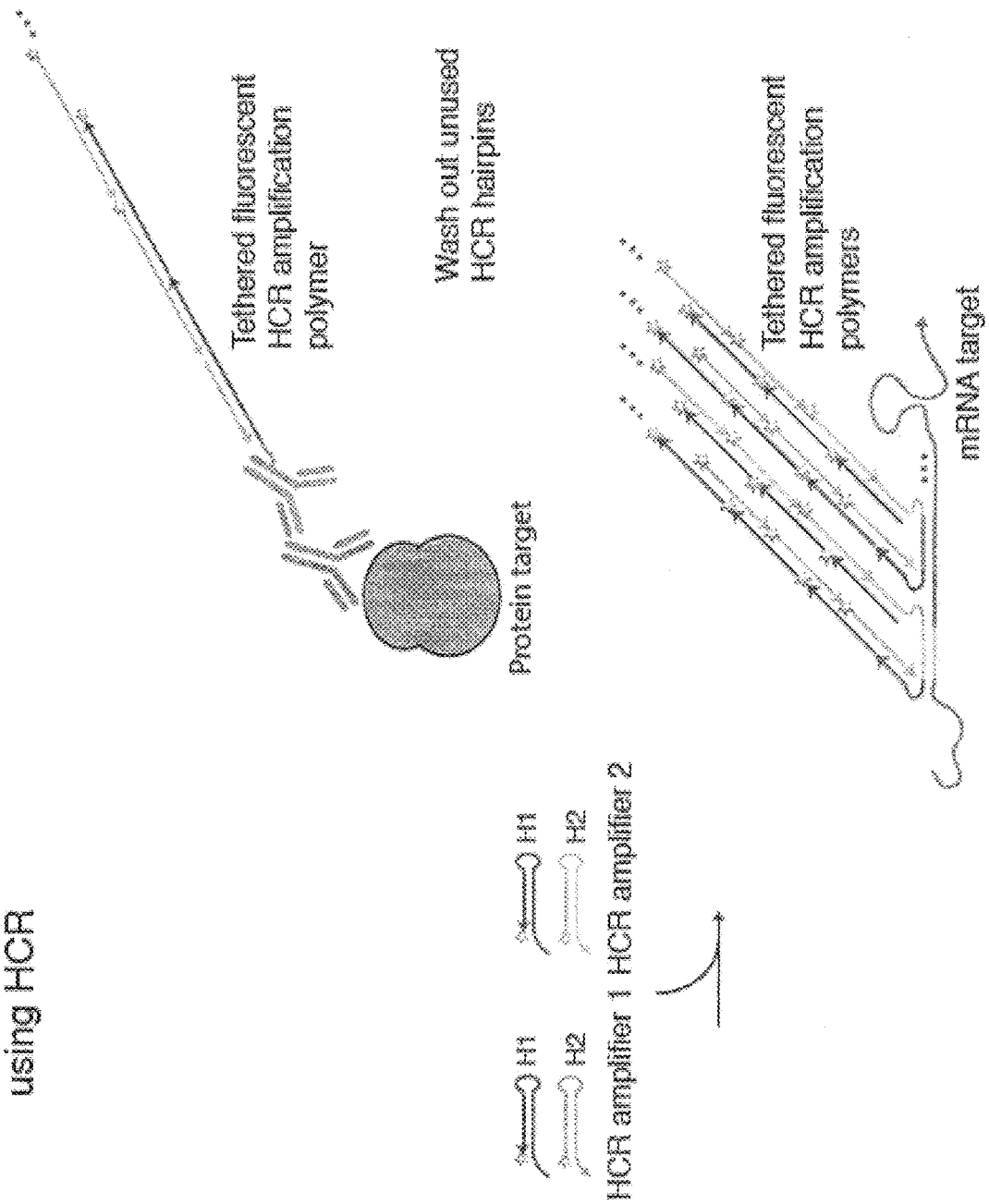
FIG. 7. Scheme for simultaneously mapping protein and mRNA expression via HCR-IHC and HCR in situ hybridization (HCR-ISH).

In situ hybridization (ISH) using HCR employs nucleic acid probes carrying HCR initiators to map mRNA targets within fixed samples (Choi et al. 2010; Choi et al. 2014). FIG. 7 provides an example of a scheme for simultaneous HCR-IHC and HCR-ISH in a single fixed specimen. HCR signal amplification is performed for all protein and mRNA targets simultaneously.

As shown in FIG. 7, Stage 1: Target protein detection uses unlabeled primary antibody; unbound primary antibodies washed form the sample. In stage 2: primary antibody detection using secondary antibody labeled with an HCR hairpin; unbound secondary antibodies washed from the sample. In stage 3: target mRNA detection using DNA probes carrying HCR initiators; unbound DNA probes washed from the sample. In stage 4: activation of the hairpin carried by the antibody probe using unstructured HCR initiator as a trigger oligo; unused trigger oligos washed from the sample. In stage 5: HCR signal amplification triggered by exposed HCR initiators carried by DNA probes selectively bound to mRNA targets (from Stage 3) or triggered by exposed HCR initiators carried by antibody probes (activated by trigger oligos in Stage 4); unbound metastable HCR hairpin monomers are washed from the sample. This example uses HCR-IHC Scheme F as the starting point, but any of Schemes A-H can be combined with HCR-ISH similarly.

Example of HCR-IHC/HCR-ISH

Example 5

Figure 8A:
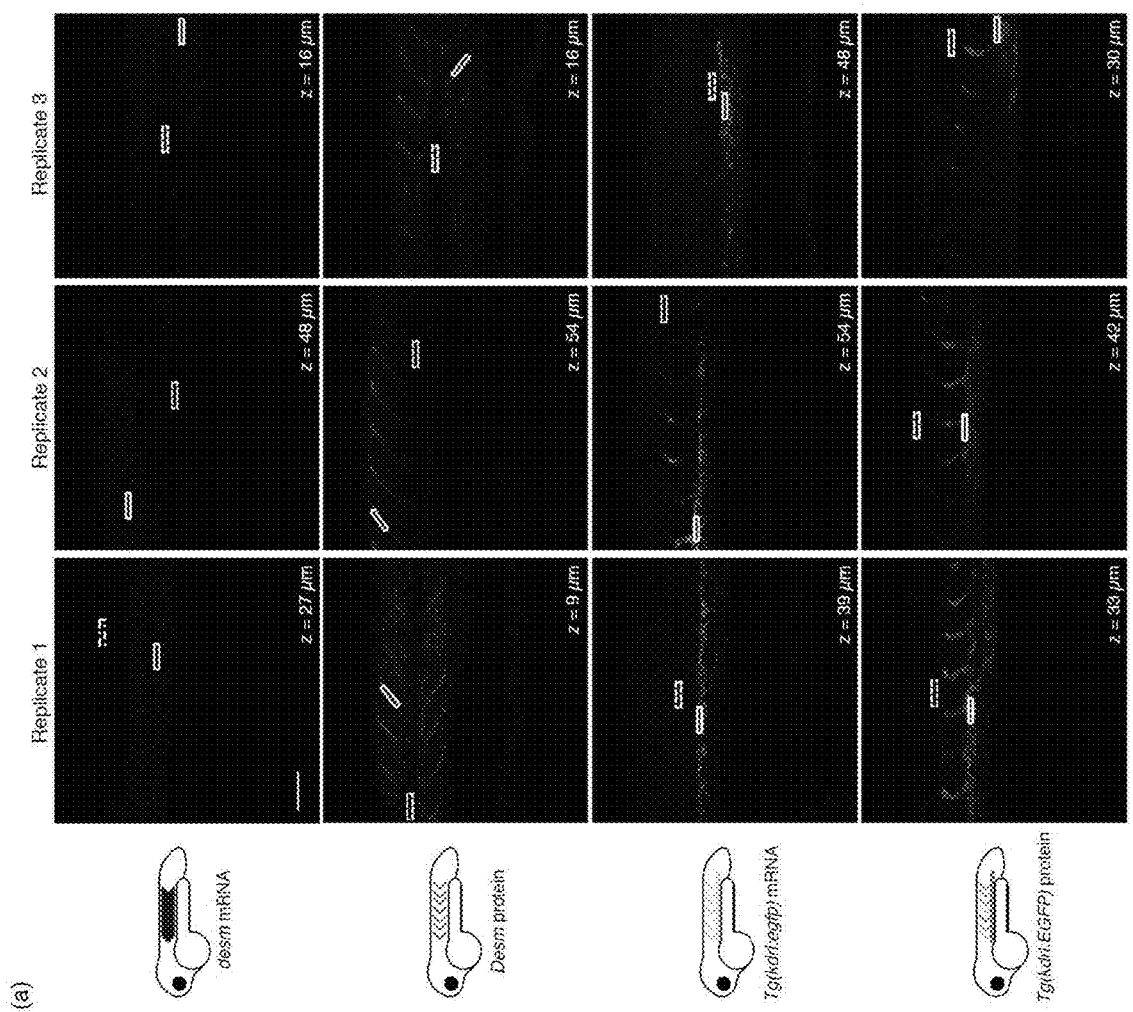
FIGS. 8A-8B. Multiplexed HCR-IHC/HCR-ISH in whole mount zebrafish embryos.
Figures 8A, 8B:
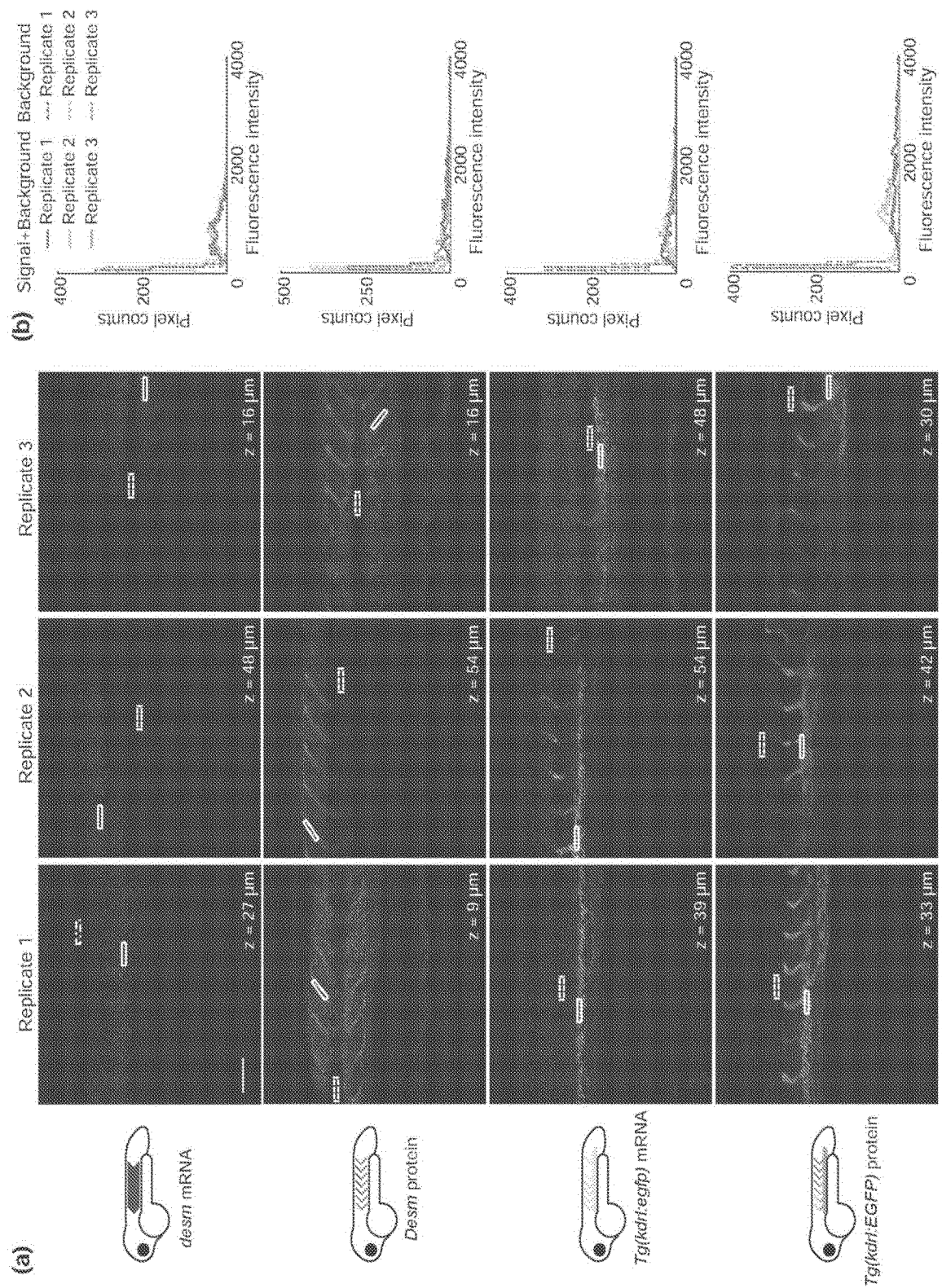
Figure 9:
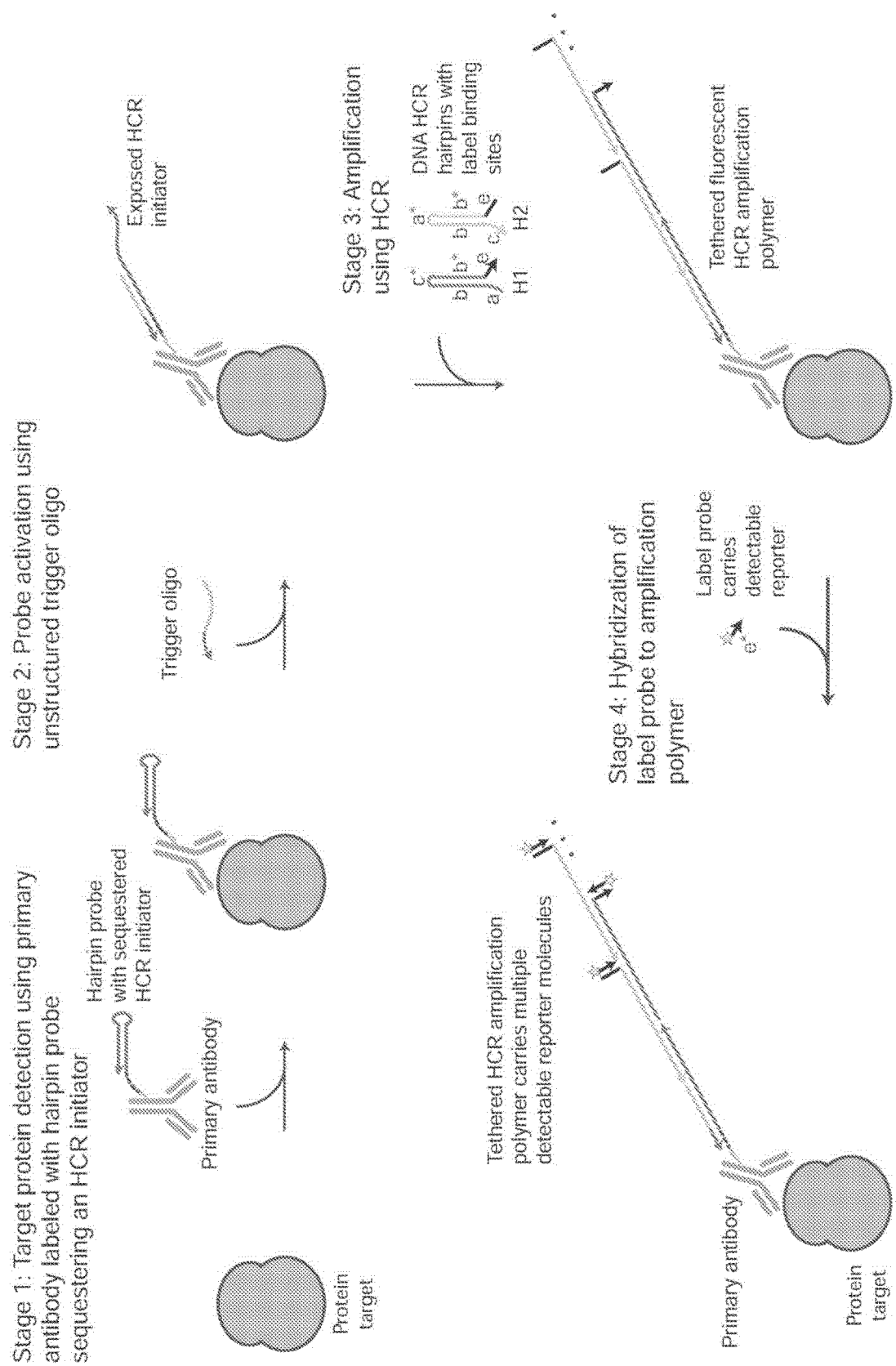

Simultaneous mapping of 2 proteins and 2 mRNAs is illustrated in the 4-channel image of FIG. 8A. High signal-to-background was achieved for all four targets. FIG. 8A depicts 4-channel confocal microscopy images showing mapping of 2 proteins and the corresponding 2 mRNAs. One representative optical section is shown for each of 3 replicate embryos. FIG. 8B provides pixel intensity histograms. Signal+Background estimated from voxels within solid boundary; Background estimated from voxels within dashed boundary. Embryos were fixed 27 hours post-fertilization. Scale bar: 50 μm. Signal-to-background (mean±standard deviation for N=3 embryos): 15±8 for desmin mRNA, 14±5 for Desmin protein, 19±9 for Tg(kdrl:egfp) mRNA, 17±6 for Tg(kdrl:eGFP) protein.

Methods of HCR Using Trigger Oligos

Example 6

HCR amplification is performed using a probe that comprises a target-binding region, which is linked to a structured nucleic acid region. The structured nucleic acid region sequesters an HCR initiator. The target-binding region binds selectively to the target, and then unbound probes are washed from the sample. Addition of a trigger oligo to the sample results in binding to the structured nucleic acid region, which results in a conformation change that exposes the HCR initiator. Exposure of the HCR initiator allows for amplification from the initiator using HCR. The resulting HCR amplification polymer contains a combination of fluorescent markers which can be detected and identified as corresponding to the presence of a particular target.

Example 7

HCR amplification is performed using a trigger oligo by providing at least one target-binding moiety that is labeled with a modified HCR hairpin; a target molecule; a trigger oligo; and a pair of metastable HCR hairpin monomers. The trigger oligo binds to the modified HCR hairpin and the pair of metastable HCR hairpin monomers do not bind directly to the modified HCR hairpin unless the trigger oligo has first bound to the modified HCR hairpin. After binding of the trigger oligo, HCR signal amplification is performed to produce an amplification polymer and a signal is detected from the polymer (where each of the HCR hairpin monomers that self-assemble to make the polymer include a reporter marker) to identify the target molecule.

Example 8

HCR amplification can be performed using a trigger oligo by providing (i) at least one target-binding moiety labeled with a structured probe sequestering an HCR initiator (ii) a target molecule, (iii) a trigger oligo, and (iv) at least a pair of polymerizing HCR hairpins. The trigger oligo binds to the structured probe. The pair of metastable HCR hairpin monomers do not bind to the sequestered HCR initiator. The trigger oligo binds to the structured probe to expose the HCR initiator, which triggers self-assembly of the fluorophore-labeled metastable HCR monomers to generate a detectable HCR amplification polymer. If each of the two metastable hairpin species carries a different fluorophore reporter, each amplification polymer will be detectable in 2 channels where the ratio of intensities in the two channels will be approximately constant independent of the length of each amplification polymer (because the number of H1 hairpin monomers in each amplification polymer is either one less, equal to, or one more than the number of H2 hairpin monomers in each amplification polymer).

What is claimed is:

1. A method comprising:
   providing a probe comprising a target-binding region linked to a structured nucleic acid region, wherein the structured nucleic acid region sequesters an HCR initiator;
   providing a trigger oligo that is not covalently linked to a domain that directly binds the target, wherein the trigger oligo directly interacts with the structured nucleic acid region, which changes conformation to expose the HCR initiator; and amplifying from the HCR initiator using HCR via a polymerization cascade that starts with the HCR initiator binding to an HCR hairpin that is not covalently linked to a domain that directly binds the target, wherein when the trigger oligo binds to an input domain, it exposes an output domain which is capable of triggering HCR, wherein the structured nucleic acid region comprises a hairpin probe, and wherein the hairpin probe comprises: the input domain comprising a toehold and stem section; and the output domain comprising a hairpin loop and a complement to the stem section, such that the output domain comprises the sequestered HCR initiator.

2. The method of claim 1, wherein HCR is performed using at least a first and second set of metastable HCR hairpin monomers.

3. The method of claim 2, wherein the first and second set of metastable HCR hairpin monomers each further comprise a reporter molecule.

4. The method of claim 3, wherein the reporter molecules are fluorescent molecules, non-fluorescent molecules, FRET molecules, or rare earth elements.

5. The method of claim 2, wherein the first and second set of metastable HCR hairpin monomers each further comprise a label-binding site that is configured to hybridize to a complement to the label binding site, wherein the complement to the label binding site further comprises a reporter molecule.

6. The method of claim 1, wherein a target molecule is a protein.

7. The method of claim 1, wherein a target molecule is a small molecule or nucleic acid.

8. The method of claim 1, wherein a target molecule is a complex of two or more proteins, nucleic acids, and/or small molecules.

9. The method of claim 1, wherein the structured nucleic acid region comprises DNA, RNA, LNA, PNA, 2'OMe-RNA, or a synthetic nucleic acid analog.

10. The method of claim 1, wherein the target-binding region comprises DNA, RNA, LNA, PNA, 2'OMe-RNA, a synthetic nucleic acid analog, amino acid, or synthetic amino acid analog.

11. The method of claim 1, wherein the target-binding region is an antibody.

12. The method of claim 11, wherein the antibody comprises a primary antibody.

13. The method of claim 1, further comprising washing away any unbound probe from a sample.

14. The method of claim 13, wherein a trigger oligo is added to the sample, after unbound probe has been washed from the sample.

15. The method of claim 1, wherein more than one target is assayed for at a time, wherein each probe comprises a target-binding region selective for each target to be assayed for.

16. The method of claim 1, wherein amplifying generates a detectable polymer that indicates a presence of a target molecule, wherein the target molecule is bound by the target-binding region.

17. A method comprising:
providing a probe comprising a target-binding region linked to a structured nucleic acid region, wherein the structured nucleic acid region sequesters an HCR initiator;
providing a trigger oligo containing an exposed domain that is unstructured in the absence of other nucleic acid molecules, wherein the exposed domain directly interacts with the structured nucleic acid region, which changes conformation to expose the HCR initiator; and
amplifying from the HCR initiator using HCR via a polymerization cascade that starts with the HCR initiator binding to an HCR hairpin that is not covalently linked to a domain that directly binds the target,
wherein when the trigger oligo binds to an input domain, it exposes an output domain which is capable of triggering HCR, wherein the structured nucleic acid region comprises a hairpin probe, and wherein the hairpin probe comprises: the input domain comprising a toehold and stem section; and the output domain comprising a hairpin loop and a complement to the stem section, such that the output domain comprises the sequestered HCR initiator.

18. A method comprising:
providing a probe comprising a target-binding region linked to a structured nucleic acid region, wherein the structured nucleic acid region sequesters an HCR initiator;
providing a trigger oligo that is not covalently linked to a domain that directly binds the target, wherein the trigger directly interacts with the structured nucleic acid region, which changes conformation to expose the HCR initiator; and
amplifying from the HCR initiator using HCR via a polymerization cascade that starts with the HCR initiator binding to an HCR hairpin that is not covalently linked to a domain that directly binds the target,
wherein the target-binding region is an antibody, and
wherein the antibody comprises a first antibody that binds to the target molecule, and a second antibody that binds to the first antibody, wherein the structured nucleic acid region is linked to the second antibody but is not linked to the first antibody.

19. A method comprising:
providing a probe comprising a target-binding region linked to a structured nucleic acid region, wherein the structured nucleic acid region sequesters an HCR initiator;
providing a trigger oligo containing an exposed domain that is unstructured in the absence of other nucleic acid molecules, wherein the exposed domain directly interacts with the structured nucleic acid region, which changes conformation to expose the HCR initiator; and
amplifying from the HCR initiator using HCR via a polymerization cascade that starts with the HCR initiator binding to an HCR hairpin that is not covalently linked to a domain that directly binds the target,
wherein the target-binding region is an antibody, and
wherein the antibody comprises a first antibody that binds to the target molecule, and a second antibody that binds to the first antibody, wherein the structured nucleic acid region is linked to the second antibody but is not linked to the first antibody.

\* \* \* \* \*

UNITED STATES PATENT AND TRADEMARK OFFICE
CERTIFICATE OF CORRECTION

PATENT NO. : 10,815,519 B2
APPLICATION NO. : 15/689786
DATED : October 27, 2020
INVENTOR(S) : Naeem S. Husain It is certified that error appears in the above-identified patent and that said Letters Patent is hereby corrected as shown below:

On the Title Page

Delete the title page and replace with the attached title page showing the corrected number of drawing sheets.

Column 2, Item (56), Line 1, under Other Publications, delete "Appendex" and insert --Appendix--.

On Page 2, Column 2, Item (56), Line 78, under Other Publications, delete "self assembly."" and insert --self-assembly."--.

On Page 3, Column 1, Item (56), Line 9, under Other Publications, delete "flurorescent" and insert --fluorescent--.

On Page 3, Column 2, Item (56), Line 7, under Other Publications, delete "Suraces," and insert --Surfaces,--.

On Page 3, Column 2, Item (56), Line 25, under Other Publications, delete "Corss-Linking" and insert --Cross-Linking--.

On Page 4, Column 1, Item (56), Line 29, under Other Publications, delete ""Phosphrothioate oligodeooxynucleotides:" and insert --"Phosphorothioate oligodeoxynucleotides:--.

On Page 4, Column 2, Item (56), Line 49, under Other Publications, delete "oligonuicleotide:" and insert --"oligonucleotide:--.

On Page 5, Column 1, Item (56), Line 64, under Other Publications, delete "Antiodies" and insert --Antibodies--.

On Page 5, Column 2, Item (56), Line 48, under Other Publications, delete "Mesenger" and insert --Messenger--.

Signed and Sealed this
Nineteenth Day of September, 2023

Katherine Kelly Vidal
*Director of the United States Patent and Trademark Office*

On Page 5, Column 2, Item (56), Line 49, under Other Publications, delete "ytoplasmic" and insert --cytoplasmic--.

On Page 6, Column 1, Item (56), Line 17, under Other Publications, delete "Hybridication,"" and insert --Hybridization,"--.

On Page 6, Column 2, Item (56), Line 60, under Other Publications, delete "lnterstrand" and insert --Interstrand--.

On Page 7, Column 2, Item (56), Line 36, under Other Publications, delete "purimidine" and insert --pyrimidine--.

On Page 7, Column 2, Item (56), Line 42, under Other Publications, delete "(bDNA))" and insert --(bDNA)--.

On Page 8, Column 1, Item (56), Line 23, under Other Publications, delete "creat" and insert --create--.

On Page 8, Column 1, Item (56), Line 41, under Other Publications, delete "lnterstrand" and insert --Interstrand--.

On Page 8, Column 2, Item (56), Line 1, under Other Publications, delete "nanstructures" and insert --nanostructures--.

On Page 8, Column 2, Item (56), Line 57, under Other Publications, delete "Oligodeoxyribonnucleotides." and insert --Oligodeoxyribonucleotides.--.

On Page 9, Column 2, Item (56), Line 20, under Other Publications, delete "(2014." and insert --(2014).--.

On Page 9, Column 2, Item (56), Line 41, under Other Publications, delete "Photocross-linking" and insert --Photocrosslinking--.

On Page 10, Column 1, Item (56), Line 60, under Other Publications, delete "Concatermers" and insert --Concatemers--.

In the Drawings

Delete drawing sheets 1-31, and in FIG. 1C, Line 1, delete "Antobody 2" and insert --Antibody 2-- as shown on the attached replacement drawings sheets 1-15.

(12) United States Patent
Husain et al.

(10) Patent No.: US 10,815,519 B2
(45) Date of Patent: Oct. 27, 2020

(54) IMMUNOHISTOCHEMISTRY VIA HYBRIDIZATION CHAIN REACTION

(71) Applicant: California Institute of Technology, Pasadena, CA (US)

(72) Inventors: Naeem S Husain, Los Angeles, CA (US); Harry Ming Tak Choi, Arcadia, CA (US); Long Cai, Pasadena, CA (US); Niles A Pierce, Pasadena, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 15/689,786

(22) Filed: Aug. 29, 2017

(65) Prior Publication Data
US 2018/0066303 A1    Mar. 8, 2018

Related U.S. Application Data

(60) Provisional application No. 62/381,474, filed on Aug. 30, 2016.

(51) Int. Cl.
*C12Q 1/6804* (2018.01)
*C12Q 1/682* (2018.01)
*G01N 33/543* (2006.01)
*C12Q 1/6825* (2018.01)
*G01N 33/536* (2006.01)

(52) U.S. Cl.
CPC ......... *C12Q 1/6804* (2013.01); *C12Q 1/682* (2013.01); *C12Q 1/6825* (2013.01); *G01N 33/536* (2013.01); *G01N 33/543* (2013.01); *G01N 33/54306* (2013.01); *G01N 2458/10* (2013.01)

(58) Field of Classification Search
CPC .... C12Q 1/6804; C12Q 1/682; C12Q 1/6825; G01N 33/54306; G01N 33/536; G01N 33/543; G01N 2458/10
See application file for complete search history.

(56) References Cited

U.S. PATENT DOCUMENTS

| | | |
|---|---|---|
| 4,714,680 A | 12/1987 | Civin |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,270,163 A | 12/1993 | Gold et al. |
| 5,312,728 A | 5/1994 | Lizardi et al. |

(Continued)

FOREIGN PATENT DOCUMENTS

| | | |
|---|---|---|
| EP | 0 273 085 | 7/1988 |
| EP | 1 479 766 | 11/2004 |

(Continued)

OTHER PUBLICATIONS

Appendex Feb. 12, 2020. Prepared by the Examiner on Feb. 12, 2020. (Year: 2020).*

(Continued)

*Primary Examiner* — Joseph G. Dauner
(74) *Attorney, Agent, or Firm* — Knobbe, Martens, Olson & Bear, LLP

(57) ABSTRACT

The present disclosure relates to methods involving HCR reactions that involve using trigger oligos to activate probes that initiate HCR.

19 Claims, 15 Drawing Sheets

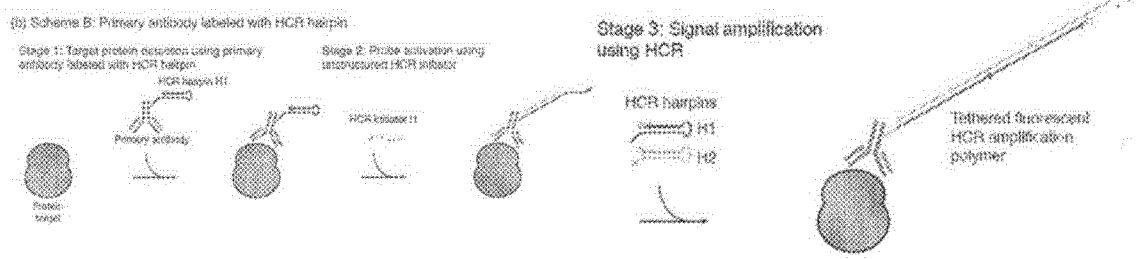

(d) Scheme D: Primary antibody labeled with hairpin probe that sequesters an HCR initiator

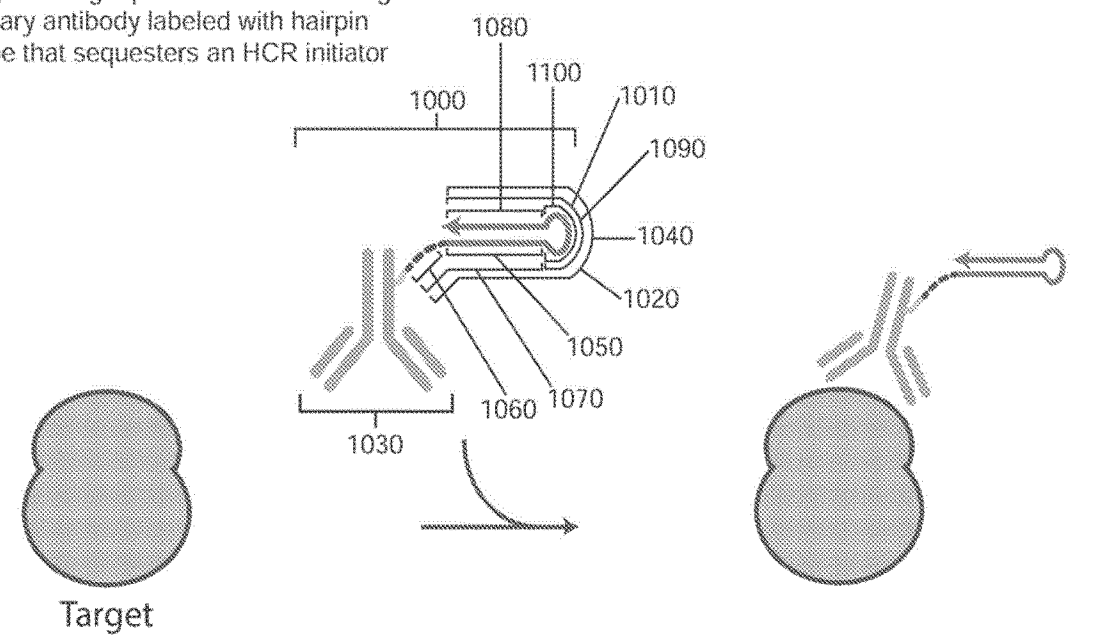

Stage 1: Target protein detection using primary antibody labeled with hairpin probe that sequesters an HCR initiator Target

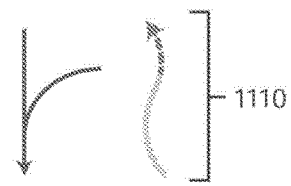

Stage 2: Probe activation using unstructured trigger oligo

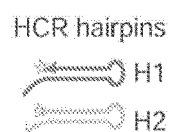

HCR hairpins
H1
H2

Tethered fluorescent HCR amplification polymer

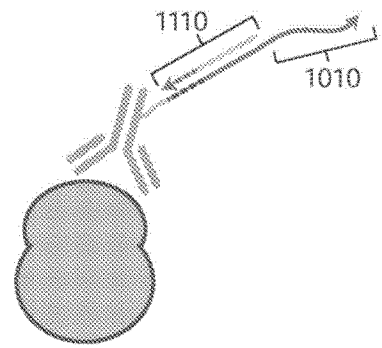

Stage 3: Signal amplification using HCR

FIG. 2D